(12) United States Patent
Wolf

(10) Patent No.: US 12,357,817 B2
(45) Date of Patent: Jul. 15, 2025

(54) NASAL NEUROMODULATION DEVICES AND METHODS

(71) Applicant: Aerin Medical Inc., Sunnyvale, CA (US)

(72) Inventor: Scott J. Wolf, Menlo Park, CA (US)

(73) Assignee: Aerin Medical Inc., Mountain View, CA (US)

( * ) Notice: Subject to any disclaimer, the term of this patent is extended or adjusted under 35 U.S.C. 154(b) by 0 days.

(21) Appl. No.: 17/658,051

(22) Filed: Apr. 5, 2022

(65) Prior Publication Data

US 2022/0313985 A1    Oct. 6, 2022

Related U.S. Application Data

(60) Provisional application No. 63/179,739, filed on Apr. 26, 2021, provisional application No. 63/171,391, filed on Apr. 6, 2021.

(51) Int. Cl.
*A61N 1/05* (2006.01)
*A61N 1/36* (2006.01)
*A61N 1/40* (2006.01)

(52) U.S. Cl.
CPC ....... *A61N 1/0546* (2013.01); *A61N 1/36075* (2013.01); *A61N 1/36189* (2013.01); *A61N 1/40* (2013.01)

(58) Field of Classification Search
CPC .................................................. A61N 1/0546
See application file for complete search history.

(56) References Cited

U.S. PATENT DOCUMENTS

| 874,178 A | 12/1907 | DeForest |
| 3,117,571 A | 1/1964 | Fry et al. |
| 3,538,919 A | 11/1970 | Meyer |

(Continued)

FOREIGN PATENT DOCUMENTS

| CN | 2225227 Y | 4/1996 |
| CN | 2621723 Y | 6/2004 |

(Continued)

OTHER PUBLICATIONS

Arora et al., "Cryodestruction of Vidian Nerve Branches," Indian J. Otolaryngology, vol. 32, No. 3, Sep. 1980, pp. 80-82.

(Continued)

*Primary Examiner* — Benjamin J Klein
*Assistant Examiner* — Thien Jason Tran
(74) *Attorney, Agent, or Firm* — Greenberg Traurig, LLP; David J. Dykeman; Roman Fayerber

(57) ABSTRACT

A method for treating nerves in a nasal cavity starts with identifying a patient having a condition occurring outside the nasal cavity. The method then involves activating a console attached to a radiofrequency stylus, advancing a distal tip of the radiofrequency stylus into a nostril of the patient, contacting nasal mucosa lining the nasal cavity with a treatment surface of the distal tip, and delivering radiofrequency energy from one set of bipolar electrodes on the treatment surface of the distal tip to a second set of bipolar electrodes on the treatment surface, to treat at least one nerve underlying the nasal mucosa. Treating the nerve (or nerves) involves modulating activity of the nerve to ameliorate the condition occurring outside the nasal cavity.

18 Claims, 37 Drawing Sheets

(56) References Cited

U.S. PATENT DOCUMENTS

| | | |
|---|---|---|
| 3,941,121 A | 3/1976 | Olinger et al. |
| 4,074,718 A | 2/1978 | Morrison |
| 4,271,848 A | 6/1981 | Turner et al. |
| 4,411,266 A | 10/1983 | Cosman |
| 4,887,605 A | 12/1989 | Angelsen et al. |
| 5,215,086 A | 6/1993 | Terry, Jr. et al. |
| 5,255,679 A | 10/1993 | Imran |
| 5,348,008 A | 9/1994 | Bornn et al. |
| 5,505,730 A | 4/1996 | Edwards |
| 5,507,725 A | 4/1996 | Savage et al. |
| 5,514,131 A | 5/1996 | Edwards et al. |
| 5,533,499 A | 7/1996 | Johnson |
| 5,542,916 A | 8/1996 | Hirsch et al. |
| 5,562,720 A | 10/1996 | Stern et al. |
| 5,575,788 A | 11/1996 | Baker et al. |
| 5,611,798 A | 3/1997 | Eggers |
| 5,624,439 A | 4/1997 | Edwards et al. |
| 5,674,191 A | 10/1997 | Edwards et al. |
| 5,697,536 A | 12/1997 | Eggers et al. |
| 5,707,349 A | 1/1998 | Edwards |
| 5,718,702 A | 2/1998 | Edwards |
| 5,728,094 A | 3/1998 | Edwards |
| 5,730,719 A | 3/1998 | Edwards |
| 5,733,280 A | 3/1998 | Avitall |
| 5,738,114 A | 4/1998 | Edwards |
| 5,743,870 A | 4/1998 | Edwards |
| 5,743,904 A | 4/1998 | Edwards |
| 5,746,224 A | 5/1998 | Edwards |
| 5,766,153 A | 6/1998 | Eggers et al. |
| 5,766,605 A | 6/1998 | Sanders et al. |
| 5,800,429 A | 9/1998 | Edwards |
| 5,807,306 A | 9/1998 | Shapland et al. |
| 5,816,095 A | 10/1998 | Nordell, II et al. |
| 5,817,049 A | 10/1998 | Edwards |
| 5,820,580 A | 10/1998 | Edwards et al. |
| 5,823,197 A | 10/1998 | Edwards |
| 5,827,277 A | 10/1998 | Edwards |
| 5,843,021 A | 12/1998 | Edwards et al. |
| 5,843,077 A | 12/1998 | Edwards |
| 5,846,235 A | 12/1998 | Pasricha et al. |
| 5,879,349 A | 3/1999 | Edwards |
| 5,891,134 A | 4/1999 | Goble et al. |
| 5,938,659 A | 8/1999 | Tu et al. |
| 5,944,715 A | 8/1999 | Goble |
| 6,033,397 A | 3/2000 | Laufer et al. |
| 6,045,549 A | 4/2000 | Smethers et al. |
| 6,096,033 A | 8/2000 | Tu et al. |
| 6,102,907 A | 8/2000 | Smethers et al. |
| 6,106,520 A | 8/2000 | Laufer et al. |
| 6,109,268 A | 8/2000 | Thapliyal et al. |
| 6,126,657 A | 10/2000 | Edwards et al. |
| 6,131,579 A | 10/2000 | Thorson et al. |
| 6,139,545 A | 10/2000 | Utley et al. |
| 6,139,546 A | 10/2000 | Koenig et al. |
| 6,152,143 A | 11/2000 | Edwards |
| 6,165,173 A | 12/2000 | Kamdar et al. |
| 6,179,803 B1 | 1/2001 | Edwards et al. |
| 6,210,355 B1 | 4/2001 | Edwards et al. |
| 6,228,079 B1 | 5/2001 | Koenig |
| 6,231,569 B1 | 5/2001 | Bek et al. |
| 6,238,394 B1 | 5/2001 | Garito et al. |
| 6,273,886 B1 | 8/2001 | Edwards et al. |
| 6,273,907 B1 | 8/2001 | Laufer |
| 6,293,941 B1 | 9/2001 | Strul et al. |
| 6,309,386 B1 | 10/2001 | Bek |
| 6,355,032 B1 | 3/2002 | Hovda et al. |
| 6,371,926 B1 | 4/2002 | Thorson et al. |
| 6,383,181 B1 | 5/2002 | Johnston et al. |
| 6,391,028 B1 | 5/2002 | Fanton et al. |
| 6,405,732 B1 | 6/2002 | Edwards et al. |
| 6,416,491 B1 | 7/2002 | Edwards et al. |
| 6,416,505 B1 | 7/2002 | Fleischman et al. |
| 6,425,151 B2 | 7/2002 | Barnett |
| 6,431,174 B1 | 8/2002 | Knudson et al. |
| 6,432,986 B2 | 8/2002 | Levin |
| 6,451,013 B1 | 9/2002 | Bays et al. |
| 6,491,940 B1 | 12/2002 | Levin |
| 6,502,574 B2 | 1/2003 | Stevens et al. |
| 6,517,534 B1 | 2/2003 | McGovern et al. |
| 6,517,535 B2 | 2/2003 | Edwards |
| 6,530,924 B1 | 3/2003 | Ellman et al. |
| 6,551,310 B1 | 4/2003 | Ganz et al. |
| 6,562,036 B1 | 5/2003 | Ellman et al. |
| 6,575,969 B1 | 6/2003 | Rittman et al. |
| 6,589,235 B2 | 7/2003 | Wong et al. |
| 6,640,120 B1 | 10/2003 | Swanson et al. |
| 6,658,279 B2 | 12/2003 | Swanson et al. |
| 6,659,106 B1 | 12/2003 | Hovda et al. |
| 6,669,689 B2 | 12/2003 | Lehmann et al. |
| 6,685,648 B2 | 2/2004 | Flaherty et al. |
| 6,735,475 B1 | 5/2004 | Whitehurst et al. |
| 6,896,674 B1 | 5/2005 | Woloszko et al. |
| 6,911,027 B1 | 6/2005 | Edwards et al. |
| 6,949,096 B2 | 9/2005 | Davison et al. |
| 6,978,781 B1 | 12/2005 | Jordan |
| 6,991,631 B2 | 1/2006 | Woloszko et al. |
| 7,055,523 B1 | 6/2006 | Brown |
| 7,097,641 B1 | 8/2006 | Arless et al. |
| 7,114,495 B2 | 10/2006 | Lockwood, Jr. |
| 7,131,969 B1 | 11/2006 | Hovda et al. |
| 7,322,993 B2 | 1/2008 | Metzger et al. |
| 7,361,168 B2 | 4/2008 | Makower et al. |
| 7,416,550 B2 | 8/2008 | Protsenko et al. |
| 7,442,191 B2 | 10/2008 | Hovda et al. |
| 7,444,184 B2 | 10/2008 | Boveja et al. |
| 7,544,204 B2 | 6/2009 | Krespi et al. |
| 7,561,919 B2 | 7/2009 | Shalev et al. |
| 7,572,251 B1 | 8/2009 | Davison et al. |
| 7,628,789 B2 | 12/2009 | Soltesz et al. |
| 7,636,597 B2 | 12/2009 | Gross et al. |
| 7,655,243 B2 | 2/2010 | Deem et al. |
| 7,678,069 B1 | 3/2010 | Baker et al. |
| 7,684,859 B2 | 3/2010 | Shalev et al. |
| 7,758,571 B2 | 7/2010 | Saadat |
| 7,780,730 B2 | 8/2010 | Saidi |
| 7,824,394 B2 | 11/2010 | Manstein |
| 7,850,683 B2 | 12/2010 | Elkins et al. |
| 7,860,569 B2 | 12/2010 | Solberg et al. |
| 7,877,147 B2 | 1/2011 | Shalev et al. |
| 7,997,278 B2 | 8/2011 | Utley et al. |
| 8,075,605 B2 | 12/2011 | Barbut et al. |
| 8,088,122 B2 | 1/2012 | Li et al. |
| 8,109,981 B2 | 2/2012 | Gertner et al. |
| 8,114,062 B2 | 2/2012 | Muni et al. |
| 8,128,617 B2 | 3/2012 | Bencini et al. |
| 8,137,345 B2 | 3/2012 | McNall, III et al. |
| 8,167,923 B2 | 5/2012 | Barbut et al. |
| 8,308,786 B2 | 11/2012 | Rozenberg et al. |
| 8,313,520 B2 | 11/2012 | Barbut et al. |
| 8,317,781 B2 | 11/2012 | Owens et al. |
| 8,317,782 B1 | 11/2012 | Ellman et al. |
| 8,388,600 B1 | 3/2013 | Eldredge |
| 8,394,075 B2 | 3/2013 | Ansarinia |
| 8,473,062 B2 | 6/2013 | Pless |
| 8,663,216 B2 | 3/2014 | Davison et al. |
| 8,666,498 B2 | 3/2014 | Newman |
| 8,676,324 B2 | 3/2014 | Simon et al. |
| 8,676,330 B2 | 3/2014 | Simon et al. |
| 8,682,449 B2 | 3/2014 | Simon |
| 8,715,169 B2 | 5/2014 | Chang et al. |
| 8,718,786 B2 | 5/2014 | Shalev |
| 8,740,765 B1 | 6/2014 | Fischell et al. |
| 8,874,227 B2 | 10/2014 | Simon et al. |
| 8,880,175 B2 | 11/2014 | Simon |
| 8,936,594 B2 | 1/2015 | Wolf et al. |
| 8,939,970 B2 | 1/2015 | Stone et al. |
| 8,958,881 B2 | 2/2015 | Lamensdorf et al. |
| 8,979,841 B2 | 3/2015 | Kunis et al. |
| 8,986,301 B2 | 3/2015 | Wolf et al. |
| 9,072,597 B2 | 7/2015 | Wolf et al. |
| 9,089,719 B2 | 7/2015 | Simon et al. |
| 9,125,677 B2 | 9/2015 | Sobol et al. |
| 9,179,964 B2 | 11/2015 | Wolf et al. |
| 9,179,967 B2 | 11/2015 | Wolf et al. |

(56) References Cited

U.S. PATENT DOCUMENTS

| | | |
|---|---|---|
| 9,233,245 B2 | 1/2016 | Lamensdorf et al. |
| 9,237,924 B2 | 1/2016 | Wolf et al. |
| 9,247,989 B2 | 2/2016 | Truckai |
| 9,302,096 B2 | 4/2016 | Levin |
| 9,381,349 B2 | 7/2016 | Levin |
| 9,409,013 B2 | 8/2016 | Mashiach et al. |
| 9,415,194 B2 | 8/2016 | Wolf et al. |
| 9,433,463 B2 | 9/2016 | Wolf et al. |
| 9,452,010 B2 | 9/2016 | Wolf et al. |
| 9,452,087 B2 | 9/2016 | Holm et al. |
| 9,468,763 B2 | 10/2016 | Simon et al. |
| 9,474,915 B2 | 10/2016 | Gonzales et al. |
| 9,486,278 B2 | 11/2016 | Wolf et al. |
| 9,498,635 B2 | 11/2016 | Dellamano et al. |
| 9,526,571 B2 | 12/2016 | Wolf et al. |
| D782,657 S | 3/2017 | Williams |
| 9,687,288 B2 | 6/2017 | Saadat |
| 9,687,296 B2 | 6/2017 | Wolf et al. |
| 9,713,700 B2 | 7/2017 | Chang et al. |
| 9,744,071 B2 | 8/2017 | Harikrishna et al. |
| 9,763,723 B2 | 9/2017 | Saadat |
| 9,763,743 B2 | 9/2017 | Lin et al. |
| 9,770,293 B2 | 9/2017 | Dresher |
| 9,788,886 B2 | 10/2017 | Wolf et al. |
| 9,801,752 B2 | 10/2017 | Wolf et al. |
| 9,833,276 B2 | 12/2017 | Newman |
| 9,888,957 B2 | 2/2018 | Wolf et al. |
| 9,913,682 B2 | 3/2018 | Wolf et al. |
| 9,943,361 B2 | 4/2018 | Wolf et al. |
| 9,974,968 B2 | 5/2018 | Reed et al. |
| 10,028,780 B2 | 7/2018 | Wolf et al. |
| 10,028,781 B2 | 7/2018 | Saadat |
| 10,076,441 B2 | 9/2018 | Rozenberg et al. |
| 10,159,538 B2 | 12/2018 | Lin et al. |
| 10,207,108 B2 | 2/2019 | Franke et al. |
| 10,220,207 B2 | 3/2019 | Simon et al. |
| 10,265,115 B2 | 4/2019 | Wolf et al. |
| 10,265,523 B2 | 4/2019 | Simon et al. |
| 10,286,211 B2 | 5/2019 | Simon et al. |
| 10,307,200 B2 | 6/2019 | Saadat |
| 10,322,279 B2 | 6/2019 | Papay |
| 10,335,221 B2 | 7/2019 | Wolf et al. |
| 10,363,419 B2 | 7/2019 | Simon et al. |
| 10,376,300 B2 | 8/2019 | Wolf et al. |
| 10,383,646 B2 | 8/2019 | Baker et al. |
| D860,315 S | 9/2019 | Chen |
| 10,398,489 B2 | 9/2019 | Wolf et al. |
| 10,456,185 B2 | 10/2019 | Wolf et al. |
| 10,456,186 B1 | 10/2019 | Wolf et al. |
| 10,470,814 B2 | 11/2019 | Wolf et al. |
| 10,470,837 B2 | 11/2019 | Lin et al. |
| 10,485,603 B2 | 11/2019 | Wolf et al. |
| 10,512,498 B2 | 12/2019 | Saadat |
| 10,561,527 B2 | 2/2020 | Rozenberg et al. |
| 10,603,059 B2 | 3/2020 | Dinger et al. |
| D880,694 S | 4/2020 | Ng et al. |
| D881,904 S | 4/2020 | Angeles et al. |
| 10,631,925 B2 | 4/2020 | Wolf et al. |
| 10,722,282 B2 | 7/2020 | Wolf et al. |
| D897,185 S | 9/2020 | Perkins, Jr. et al. |
| D897,186 S | 9/2020 | Perkins, Jr. et al. |
| 10,773,080 B2 | 9/2020 | Rigaux |
| 10,779,873 B2 | 9/2020 | Wolf et al. |
| 10,780,273 B2 | 9/2020 | Franke et al. |
| 10,806,921 B2 | 10/2020 | Townley et al. |
| D904,698 S | 12/2020 | Moeller et al. |
| D904,852 S | 12/2020 | Levand et al. |
| 10,864,035 B2 | 12/2020 | Hester et al. |
| 10,864,371 B2 | 12/2020 | Shimada et al. |
| D906,782 S | 1/2021 | Brinson et al. |
| D910,408 S | 2/2021 | Lin |
| D911,140 S | 2/2021 | Hyma et al. |
| D911,141 S | 2/2021 | Panosian et al. |
| 10,918,864 B2 | 2/2021 | Franke et al. |
| 10,932,853 B2 | 3/2021 | Wolf et al. |
| 10,939,965 B1 | 3/2021 | Saadat et al. |
| 10,940,310 B2 | 3/2021 | Loudin et al. |
| 10,967,173 B2 | 4/2021 | Ackemann et al. |
| 11,026,738 B2 | 6/2021 | Saadat et al. |
| 11,033,318 B2 | 6/2021 | Wolf et al. |
| D927,687 S | 8/2021 | Stoklund et al. |
| 11,116,566 B2 | 9/2021 | Dinger et al. |
| 11,241,271 B2 | 2/2022 | Wolf et al. |
| 11,253,312 B2 | 2/2022 | Fox et al. |
| 11,278,356 B2 | 3/2022 | Fahey et al. |
| 11,304,746 B2 | 4/2022 | Wolf et al. |
| 11,457,971 B2 | 10/2022 | Wolf et al. |
| 11,458,297 B2 | 10/2022 | Simon et al. |
| 11,458,325 B2 | 10/2022 | Simon et al. |
| 11,490,960 B2 | 11/2022 | van der Weide et al. |
| 11,511,109 B2 | 11/2022 | Simon et al. |
| 11,529,502 B2 | 12/2022 | Chang et al. |
| 11,576,559 B2 | 2/2023 | Saadat et al. |
| 11,602,260 B2 | 3/2023 | Saadat et al. |
| 11,612,756 B2 | 3/2023 | Reed et al. |
| 11,623,078 B2 | 4/2023 | Simon et al. |
| 11,633,151 B2 | 4/2023 | Pivonka et al. |
| 11,654,277 B2 | 5/2023 | Simon et al. |
| 11,679,263 B2 | 6/2023 | Hsu et al. |
| 11,684,771 B2 | 6/2023 | Ben-David et al. |
| 11,759,222 B2 | 9/2023 | Wolf et al. |
| 11,766,286 B2 | 9/2023 | Wolf et al. |
| 11,771,497 B2 | 10/2023 | Townley et al. |
| 11,786,292 B2 | 10/2023 | Fox et al. |
| 11,786,296 B2 | 10/2023 | Shameli et al. |
| 11,801,084 B2 | 10/2023 | Wolf et al. |
| 11,806,071 B2 | 11/2023 | Frazier |
| 11,806,072 B2 | 11/2023 | Hakimimehr |
| 11,832,876 B2 | 12/2023 | Wolf et al. |
| 11,864,725 B2 | 1/2024 | Chang et al. |
| 11,883,091 B2 | 1/2024 | Townley |
| 11,883,665 B2 | 1/2024 | Hsu et al. |
| 11,896,293 B2 | 2/2024 | Kreindel |
| 11,896,818 B2 | 2/2024 | Townley |
| 11,944,807 B2 | 4/2024 | Simon et al. |
| 11,944,815 B2 | 4/2024 | Simon et al. |
| 11,969,200 B2 | 4/2024 | Hester et al. |
| 11,986,232 B2 | 5/2024 | Fahey et al. |
| 11,992,681 B2 | 5/2024 | Mulrooney |
| 12,053,227 B2 | 8/2024 | Wolf et al. |
| 12,070,593 B2 | 8/2024 | Simon et al. |
| 12,082,863 B1 | 9/2024 | Atkins, Jr. et al. |
| 12,082,872 B2 | 9/2024 | Townley et al. |
| 12,108,979 B2 | 10/2024 | Townley |
| 12,121,281 B2 | 10/2024 | Shaari |
| 2002/0010460 A1 | 1/2002 | Joye et al. |
| 2002/0016588 A1 | 2/2002 | Wong et al. |
| 2002/0035361 A1 | 3/2002 | Houser |
| 2002/0049464 A1 | 4/2002 | Donofrio et al. |
| 2002/0087155 A1 | 7/2002 | Underwood et al. |
| 2002/0120259 A1 | 8/2002 | Lettice et al. |
| 2002/0128641 A1 | 9/2002 | Underwood et al. |
| 2003/0069620 A1 | 4/2003 | Li |
| 2003/0144659 A1 | 7/2003 | Edwards |
| 2003/0208194 A1 | 11/2003 | Hovda et al. |
| 2003/0208250 A1 | 11/2003 | Edwards |
| 2003/0225403 A1 | 12/2003 | Woloszko et al. |
| 2004/0030334 A1 | 2/2004 | Quick et al. |
| 2004/0193238 A1 | 9/2004 | Mosher et al. |
| 2004/0210214 A1 | 10/2004 | Knowlton |
| 2004/0215235 A1 | 10/2004 | Jackson et al. |
| 2004/0220644 A1 | 11/2004 | Shalev et al. |
| 2004/0230188 A1 | 11/2004 | Cioanta et al. |
| 2005/0020901 A1 | 1/2005 | Belson et al. |
| 2005/0119643 A1 | 6/2005 | Sobol et al. |
| 2005/0171522 A1 | 8/2005 | Christopherson |
| 2005/0171574 A1 | 8/2005 | Rubinsky et al. |
| 2005/0222565 A1 | 10/2005 | Manstein |
| 2005/0234439 A1 | 10/2005 | Underwood |
| 2005/0234443 A1 | 10/2005 | Rioux et al. |
| 2005/0240147 A1 | 10/2005 | Makower et al. |
| 2005/0288665 A1 | 12/2005 | Woloszko |
| 2006/0004323 A1 | 1/2006 | Chang et al. |
| 2006/0004423 A1 | 1/2006 | Boveja et al. |

(56) References Cited

U.S. PATENT DOCUMENTS

| | | |
|---|---|---|
| 2006/0009758 A1 | 1/2006 | Edwards et al. |
| 2006/0064086 A1 | 3/2006 | Odom |
| 2006/0095066 A1 | 5/2006 | Chang et al. |
| 2006/0190022 A1 | 8/2006 | Beyar et al. |
| 2006/0195169 A1 | 8/2006 | Gross et al. |
| 2006/0235377 A1 | 10/2006 | Earley et al. |
| 2006/0253117 A1 | 11/2006 | Hovda et al. |
| 2006/0265031 A1 | 11/2006 | Skwarek et al. |
| 2006/0276817 A1 | 12/2006 | Vassallo et al. |
| 2007/0043350 A1 | 2/2007 | Soltesz et al. |
| 2007/0049999 A1 | 3/2007 | Esch et al. |
| 2007/0066944 A1 | 3/2007 | Nyte |
| 2007/0073282 A1 | 3/2007 | McGarrigan et al. |
| 2007/0083193 A1 | 4/2007 | Werneth et al. |
| 2007/0093710 A1 | 4/2007 | Maschke |
| 2007/0179495 A1 | 8/2007 | Mitchell et al. |
| 2007/0208395 A1 | 9/2007 | Leclerc et al. |
| 2007/0219600 A1 | 9/2007 | Gertner et al. |
| 2007/0244529 A1 | 10/2007 | Choi et al. |
| 2007/0287994 A1 | 12/2007 | Patel |
| 2008/0000477 A1 | 1/2008 | Huster et al. |
| 2008/0004613 A1 | 1/2008 | Barbut et al. |
| 2008/0021369 A1 | 1/2008 | Deem et al. |
| 2008/0027423 A1 | 1/2008 | Choi et al. |
| 2008/0027480 A1 | 1/2008 | van der Burg et al. |
| 2008/0027505 A1 | 1/2008 | Levin et al. |
| 2008/0027520 A1 | 1/2008 | Choi et al. |
| 2008/0082090 A1 | 4/2008 | Manstein |
| 2008/0125626 A1 | 5/2008 | Chang et al. |
| 2008/0154237 A1 | 6/2008 | Chang et al. |
| 2008/0154343 A1 | 6/2008 | Li et al. |
| 2008/0183251 A1 | 7/2008 | Azar et al. |
| 2008/0255642 A1 | 10/2008 | Zarins et al. |
| 2008/0312644 A1 | 12/2008 | Fourkas et al. |
| 2009/0012577 A1 | 1/2009 | Rezai et al. |
| 2009/0018485 A1 | 1/2009 | Krespi et al. |
| 2009/0124958 A1 | 5/2009 | Li et al. |
| 2009/0143821 A1 | 6/2009 | Stupak |
| 2009/0163890 A1 | 6/2009 | Clifford et al. |
| 2009/0192505 A1 | 7/2009 | Askew et al. |
| 2009/0210026 A1 | 8/2009 | Solberg et al. |
| 2009/0292358 A1 | 11/2009 | Saidi |
| 2009/0299355 A1 | 12/2009 | Bencini et al. |
| 2009/0299418 A1 | 12/2009 | Shalev et al. |
| 2010/0049188 A1 | 2/2010 | Nelson et al. |
| 2010/0144996 A1 | 6/2010 | Kennedy et al. |
| 2010/0152730 A1 | 6/2010 | Makower et al. |
| 2010/0160906 A1 | 6/2010 | Jarrard |
| 2010/0174283 A1 | 7/2010 | McNall, III et al. |
| 2010/0174340 A1 | 7/2010 | Simon |
| 2010/0204560 A1 | 8/2010 | Salahieh et al. |
| 2010/0241112 A1 | 9/2010 | Watson |
| 2010/0260703 A1 | 10/2010 | Yankelson et al. |
| 2010/0262133 A1 | 10/2010 | Hoey et al. |
| 2011/0009737 A1 | 1/2011 | Manstein |
| 2011/0118726 A1 | 5/2011 | De La Rama et al. |
| 2011/0125149 A1 | 5/2011 | El-Galley et al. |
| 2011/0130689 A1 | 6/2011 | Cohen et al. |
| 2011/0166624 A1 | 7/2011 | Dietrich et al. |
| 2011/0180064 A1 | 7/2011 | Tanaka et al. |
| 2011/0282268 A1 | 11/2011 | Baker et al. |
| 2011/0288477 A1 | 11/2011 | Ressemann et al. |
| 2011/0301587 A1 | 12/2011 | Deem et al. |
| 2012/0029512 A1 | 2/2012 | Willard et al. |
| 2012/0039954 A1 | 2/2012 | Cupit et al. |
| 2012/0059255 A1 | 3/2012 | Paul et al. |
| 2012/0078377 A1 | 3/2012 | Gonzales et al. |
| 2012/0123411 A1 | 5/2012 | Ibrahim et al. |
| 2012/0179154 A1 | 7/2012 | Goldberg et al. |
| 2012/0197361 A1 | 8/2012 | Gonzales et al. |
| 2012/0209257 A1 | 8/2012 | Van Der Weide et al. |
| 2012/0265188 A1 | 10/2012 | Buchbinder et al. |
| 2012/0298105 A1 | 11/2012 | Osorio |
| 2012/0310233 A1 | 12/2012 | Dimmer et al. |
| 2012/0316473 A1 | 12/2012 | Bonutti et al. |
| 2012/0316557 A1 | 12/2012 | Sartor et al. |
| 2012/0323227 A1 | 12/2012 | Wolf et al. |
| 2012/0323232 A1 | 12/2012 | Wolf et al. |
| 2013/0085546 A1 | 4/2013 | Bolea et al. |
| 2013/0116679 A1 | 5/2013 | Van Der Weide et al. |
| 2013/0158536 A1 | 6/2013 | Bloom |
| 2013/0165990 A1 | 6/2013 | Mathur et al. |
| 2013/0218158 A1 | 8/2013 | Danek et al. |
| 2013/0274824 A1 | 10/2013 | Otto et al. |
| 2013/0281997 A1 | 10/2013 | Davie |
| 2014/0088463 A1 | 3/2014 | Wolf et al. |
| 2014/0114233 A1 | 4/2014 | Deem et al. |
| 2014/0243793 A1 | 8/2014 | Morriss et al. |
| 2014/0316396 A1 | 10/2014 | Wolf et al. |
| 2015/0141982 A1 | 5/2015 | Lee |
| 2015/0148791 A1 | 5/2015 | Birdsall et al. |
| 2015/0164571 A1 | 6/2015 | Saadat |
| 2015/0202003 A1 | 7/2015 | Wolf et al. |
| 2015/0265836 A1 | 9/2015 | Simon et al. |
| 2016/0045277 A1 | 2/2016 | Lin et al. |
| 2016/0121112 A1 | 5/2016 | Azar |
| 2016/0274661 A1 | 9/2016 | Maeda |
| 2016/0287315 A1* | 10/2016 | Wolf ..................... A61B 18/12 |
| 2016/0331459 A1 | 11/2016 | Townley |
| 2016/0354136 A1 | 12/2016 | Saadat |
| 2017/0105793 A1 | 4/2017 | Cao |
| 2017/0231651 A1 | 8/2017 | Dinger et al. |
| 2017/0252089 A1 | 9/2017 | Hester |
| 2017/0252100 A1 | 9/2017 | Wolf et al. |
| 2017/0360495 A1 | 12/2017 | Wolf et al. |
| 2018/0000535 A1 | 1/2018 | Wolf et al. |
| 2018/0103940 A1 | 4/2018 | Shin et al. |
| 2018/0103992 A1 | 4/2018 | Guyuron |
| 2018/0132947 A1 | 5/2018 | Dayan et al. |
| 2018/0177542 A1 | 6/2018 | Wolf et al. |
| 2018/0177546 A1* | 6/2018 | Dinger ..................... A61N 1/06 |
| 2018/0185085 A1 | 7/2018 | Wolf et al. |
| 2018/0228533 A1 | 8/2018 | Wolf et al. |
| 2018/0228551 A1 | 8/2018 | Moe |
| 2018/0263678 A1 | 9/2018 | Saadat |
| 2018/0317997 A1 | 11/2018 | Dinger et al. |
| 2018/0333195 A1 | 11/2018 | Greep et al. |
| 2018/0344378 A1 | 12/2018 | Wolf et al. |
| 2019/0076185 A1 | 3/2019 | Dinger et al. |
| 2019/0151005 A1 | 5/2019 | Wolf et al. |
| 2019/0175242 A1 | 6/2019 | Wolf et al. |
| 2019/0201069 A1 | 7/2019 | Wolf et al. |
| 2019/0231409 A1 | 8/2019 | Wolf et al. |
| 2019/0282289 A1 | 9/2019 | Wolf et al. |
| 2019/0290865 A1 | 9/2019 | Fahey et al. |
| 2019/0336196 A1 | 11/2019 | Wolf et al. |
| 2019/0343577 A1 | 11/2019 | Wolf et al. |
| 2019/0357927 A1 | 11/2019 | Palushi |
| 2020/0053487 A1 | 2/2020 | Simon et al. |
| 2020/0100829 A1 | 4/2020 | Wolf et al. |
| 2020/0129223 A1 | 4/2020 | Angeles et al. |
| 2020/0155830 A1 | 5/2020 | Baldwin et al. |
| 2020/0155831 A1 | 5/2020 | Wardle et al. |
| 2020/0170699 A1 | 6/2020 | Wolf et al. |
| 2020/0205884 A1 | 7/2020 | Wolf et al. |
| 2020/0375648 A1 | 12/2020 | Wolf et al. |
| 2020/0391024 A1 | 12/2020 | Wardle |
| 2020/0405383 A1 | 12/2020 | Townley |
| 2021/0030464 A1 | 2/2021 | Na |
| 2021/0038277 A1 | 2/2021 | Shaari |
| 2021/0169566 A1* | 6/2021 | Townley ................. A61B 34/25 |
| 2021/0236175 A1 | 8/2021 | Frazier et al. |
| 2021/0275241 A1* | 9/2021 | Fahey ................. A61B 18/0218 |
| 2021/0315638 A1 | 10/2021 | Townley et al. |
| 2021/0369320 A1 | 12/2021 | Fahey et al. |
| 2021/0379374 A1 | 12/2021 | Hamner et al. |
| 2022/0022951 A1 | 1/2022 | Townley |
| 2022/0061922 A1 | 3/2022 | Fang et al. |
| 2022/0071802 A1 | 3/2022 | Christopherson |
| 2022/0079656 A1 | 3/2022 | Townley |
| 2022/0104862 A1 | 4/2022 | Townley et al. |
| 2022/0104866 A1 | 4/2022 | Townley et al. |
| 2022/0104869 A1 | 4/2022 | Townley et al. |
| 2022/0104870 A1 | 4/2022 | Townley et al. |

(56) References Cited

U.S. PATENT DOCUMENTS

| | | |
|---|---|---|
| 2022/0142699 A1 | 5/2022 | Wolf et al. |
| 2022/0151689 A1 | 5/2022 | Yih et al. |
| 2022/0160537 A1 | 5/2022 | Mulrooney |
| 2022/0193410 A1 | 6/2022 | Galor |
| 2022/0233832 A1 | 7/2022 | Fahey et al. |
| 2022/0257272 A1 | 8/2022 | Wolf et al. |
| 2022/0257298 A1 | 8/2022 | Fox et al. |
| 2022/0313484 A1 | 10/2022 | Fahey et al. |
| 2022/0313985 A1 | 10/2022 | Wolf |
| 2022/0361941 A1 | 11/2022 | Townley |
| 2022/0409269 A1 | 12/2022 | Palushi et al. |
| 2023/0062359 A1 | 3/2023 | Wolf et al. |
| 2023/0133359 A1 | 5/2023 | Townley |
| 2023/0200637 A1 | 6/2023 | Hakimimehr et al. |
| 2023/0248411 A1 | 8/2023 | Fox et al. |
| 2023/0277236 A1 | 9/2023 | Townley et al. |
| 2023/0293222 A1 | 9/2023 | Wolf et al. |
| 2023/0364413 A1 | 11/2023 | Romaniw et al. |
| 2023/0372003 A1 | 11/2023 | Townley |
| 2023/0372004 A1 | 11/2023 | Townley |
| 2024/0024016 A1 | 1/2024 | Wolf et al. |
| 2024/0024664 A1 | 1/2024 | Patel |
| 2024/0050143 A1 | 2/2024 | Wolf et al. |
| 2024/0050148 A1 | 2/2024 | Wolf et al. |
| 2024/0091537 A1 | 3/2024 | Boggs et al. |
| 2024/0122641 A1 | 4/2024 | Frazier et al. |
| 2024/0138895 A1 | 5/2024 | Hakimimehr |
| 2024/0198103 A1 | 6/2024 | Hsu et al. |
| 2024/0216682 A1 | 7/2024 | Shah et al. |
| 2024/0299212 A1 | 9/2024 | Bakhsheshi et al. |
| 2024/0315755 A1 | 9/2024 | Wolf et al. |
| 2024/0366286 A1 | 11/2024 | Wolf et al. |

FOREIGN PATENT DOCUMENTS

| | | |
|---|---|---|
| CN | 101325919 A | 12/2008 |
| CN | 103055417 A | 4/2013 |
| DE | 102007006467 B3 | 3/2008 |
| WO | 1999007299 A1 | 2/1999 |
| WO | 1999030655 A1 | 6/1999 |
| WO | 1999032041 A1 | 7/1999 |
| WO | 2001043653 A1 | 6/2001 |
| WO | 2003024349 A1 | 3/2003 |
| WO | 2004044947 A3 | 5/2004 |
| WO | 2004045242 A3 | 5/2004 |
| WO | 2005002467 A3 | 1/2005 |
| WO | 2007037895 A1 | 4/2007 |
| WO | 2007058780 A9 | 5/2007 |
| WO | 2007106856 A3 | 9/2007 |
| WO | 2007134005 A1 | 11/2007 |
| WO | 2008051918 A3 | 5/2008 |
| WO | 2008063179 A1 | 5/2008 |
| WO | 2008076986 A1 | 6/2008 |
| WO | 2009048580 A1 | 4/2009 |
| WO | 2010077980 A1 | 7/2010 |
| WO | 2012174161 A2 | 12/2012 |
| WO | 2013028998 A2 | 2/2013 |
| WO | 2013165697 A1 | 11/2013 |
| WO | 2014022436 A1 | 2/2014 |
| WO | 2015013252 A1 | 1/2015 |
| WO | 2015047863 A1 | 4/2015 |
| WO | 2015048806 A2 | 4/2015 |
| WO | 2015109023 A1 | 7/2015 |
| WO | 2015153696 A1 | 10/2015 |
| WO | 2016014436 A1 | 1/2016 |
| WO | 2016043382 A1 | 3/2016 |
| WO | 2016183337 A2 | 11/2016 |
| WO | 2017120357 A1 | 7/2017 |
| WO | 2021087365 A1 | 5/2021 |
| WO | 2022074461 A3 | 4/2022 |
| WO | 2022225112 A1 | 10/2022 |
| WO | 2023095958 A1 | 1/2023 |
| WO | 2023141677 A1 | 8/2023 |
| WO | 2023225265 A1 | 11/2023 |
| WO | 2024025054 A1 | 2/2024 |

OTHER PUBLICATIONS

Back et al., "Submucosal Bipolar Radiofrequency Thermal Ablation of Inferior Turbinates: A Long-Tenn Follow-up with Subjective and Objective Assessment," Laryngoscope, vol. 112, No. 10, Oct. 2002, pp. 1806-1812.

Banhiran et al., "Quality of life in patients with chronic rhinitis after radiofrequency inferior turbinate reduction," J. Med Assoc Thai, vol. 93, No. 8, 2010, pp. 950-957.

Bronzino, Medical Devices and Systems, The Biomedical Engineering Handbook (3rd ed. 2006), Chapter 63, Electrosurgical Devices, pp. 63-1-63-9.

Chen et al., "Preliminary study on radiofrequency thermocoagulation of the posterior inferior nerve, anterior ethmoidal nerve, and inferior turbinate under nasal endoscopy for the treatment of perennial allergic rhinitis," China Journal of Endoscopy, vol. 11, No. 3, Mar. 2005, pp. 239-240 and p. 243 (English Translation).

Chen et al., "Radiofrequency treatment of nasal posterior-under nerve, ethmoidal nerve and infraturbinal for perennial allergic rhinitis under nasal endoscope," China Journal of Endoscopy, vol. 11, No. 3, Mar. 2005, pp. 239-240 and p. 243 (English Translation).

Coste et al., "Radiofrequency Is a Safe and Effective Treatment of Turbinate Hypertrophy," Laryngoscope, vol. 111, No. 5, May 2001, pp. 894-899.

Fang et al., "Nasal Endoscopy Combined with Multiple Radiofrequency for Perennial Allergic Rhinitis," J. First Mil Med Univ, vol. 25, No. 7, 2005, pp. 876-877 (English Translation).

Haemmerich, "Biophysics of Radiofrequency Ablation," Critical Reviews in Biomedical Engineering, vol. 38, No. 1, 2010, pp. 53-63.

Haikou, "Diagnostic Criteria and Efficacy Evaluation Criteria of Allergic Rhinitis," Otorhinolaryngol, vol. 33, No. 3, Jun. 1998, pp. 134-135.

Hong et al., "Radiofrequency Ablation: Mechanism of Action and Devices," J. Vasc. Interv. Radiol., vol. 21, No. 8S, 2010, pp. S179-S186.

Hytönen et al., "Radiofrequency Thermal Ablation for Patients with Nasal Symptoms: A Systematic Review of Effectiveness and Complications," Eur. Arch. Otorhinolaryngol, vol. 266, 2009, pp. 1257-1266.

Ilgner et al., "Feasibility of coblation versus laser resection in recurrent nasal polyps," Proc. of SPIE, vol. 5686, Apr. 25, 2005, pp. 322-327.

Kong et al, "Low-temperature plasma ablation of inferior turbinate for the treatment of perennial allergic rhinitis", J Clin. Otorhinolaryngol., vol. 19, No. 5, Mar. 2005, pp. 214-215 (English Translation).

Kong et al., "Clinical Observation on Radiofrequency Ablation Treatment in Perennial Allergic Rhinitis," J Clin. Otorhinolaryngol., vol. 19, No. 5, Mar. 2005, pp. 214-215 (English Translation).

Konno, "Historical, Pathophysiological, and Therapeutic Aspects of Vidian Neurectomy," Curr. Allergy Asthma Rep., vol. 10, 2010, pp. 105-112.

Koyyalagunta et al., Radiofrequency and Cryoablation for Cancer Pain, Techniques in Regional Anesthesia & Pain Management, vol. 14, No. 1, Jan. 2010, pp. 3-9.

Lee et al., "Surgical Management of Turbinate Hypertrophy in the Office: Three Mucosal Sparing Techniques," Operative Techniques in Ottolaryngology—Head and Neck Surgery, vol. 12, No. 2, Jun. 2001, pp. 107-111.

Levine, "Lasers in Endonasal Surgery," Otolaryngolog. Clinics of N. Am, June, vol. 30, No. 3, Jun. 1, 1997, pp. 451-455.

Liang et al., "Radiofrequency Treatment of Ethmoidal Nerve with Allergic Rhinitis Under Nasal Endoscopy," J. Clint Otorhinolaryngol., vol. 13, No. 8, Aug. 1999, pp. 341-342 (English Translation).

Philippson, "Principles of Electrical Resistance of Living Tissue," Bull. Cl. Sci. Acad. R. Belg., Ser. 5, vol. 7, No. 7, Jul. 1921, pp. 387-403.

Sackenheim, "Radio Frequency Ablation the Key to Cancer Treatment," J. Diagnostic Medical Sonography, vol. 19, No. 2, 2003, pp. 88-92.

(56) References Cited

OTHER PUBLICATIONS

Windsor et al., "Sphenopalatine Ganglion Blockage: A Review and Proposed Modification of the Transnasal Technique," Pain Physician, vol. 7, 2004, pp. 283-286.
Wolf, "How a Serial Entrepreneur Identifies and Evaluates Product Ideas and Brings Them to Market," Mastering Medical Device Podcast, Episode Transcript, 21 pages. https://www.masteringmedicaldevice.com/episodes/wolf.
Buckley et al., "High-resolution spatial mapping of shear properties in cartilage," J Biomech., Mar. 3, 2010;43(4):796-800, Epub Nov. 5, 2009.
Buckley et al., "Mapping the depth dependence of shear properties in articular cartilage," J Biomech., 41(11):2430-2437, Epub Jul. 10, 2008.
Cole, "Biophysics of nasal airflow: a review," Am J Rhinol., 14(4):245-249, Jul.-Aug. 2000.
Cole, "The four components of the nasal valve," Am J Rhinol., 17(2):107-110, Mar.-Apr. 2003.
Fang et al., "Nasal Endoscopic Surgery Combined with Multisite Radiofrequency Technology for Treating Perennial Allergic Rhinitis," J First Mil Med Univ, vol. 25 No. 7, pp. 876-877, 2005.
Griffin et al., "Effects of enzymatic treatments on the depth-dependent viscoelastic shear properties of articular cartilage," J Orthop Res., 32(12):1652-1657, Epub Sep. 5, 2014.
Kjaergaard et al., "Relation of nasal air flow to nasal cavity dimensions," Arch Otolaryngol Head Neck Surg., 135(6):565-570, Jun. 2009.
Liu et al., "Impact of radiofrequency thermocoagulation of bilateral vidian and anterior ethmoidal nerve cluster regions on nasal mucociliary transport function in perennial allergic rhinitis and vasomotor rhinitis," China Journal of Endoscopy, vol. 14, No. 11, 12 pages, Nov. 2008.
Silverberg et al., "Structure-function relations and rigidity percolation in the shear properties of articular cartilage," Biophys J., 107(7):1721-1730, Oct. 7, 2014.
Stewart et al., "Development and validation of the Nasal Obstruction Symptom Evaluation (NOSE) scale," Otolaryngol Head Neck Surg., 130(2):157-163, Feb. 2004.
Stupak, "A Perspective on the Nasal Valve," Dept. of Otorhinolaryngology, Albert Einstein College of Medicine, Nov. 6, 2009.
Stupak, "Endonasal repositioning of the upper lateral cartilage and the internal nasal valve," Ann Otol Rhinol Laryngol., 120(2):88-94, Feb. 2011.
International Search Report and Written Opinion for PCT/US2012/042316, mailed Aug. 24, 2012, 15 pages.
International Search Report and Written Opinion for PCT/US2014/054726, mailed Dec. 23, 2014, 5 pages.
International Search Report and Written Opinion for PCT/US2015/023742, mailed Jun. 29, 2015, 5 pages.
Singapore Search Report for Application Serial No. 201309238-2, mailed Apr. 17, 2014, 27 pages.
Supplementary European Search Report for Application No. 15772528, mailed Sep. 26, 2017, 7 pages.
Search Report in European Application No. 18204723.3 dated Feb. 18, 2019, 8 pages.
Extended European Search Report for Application No. 19199126.4, mailed Dec. 9, 2019, 6 pages.
Extended European Search Report for App. No. 19159707.9, mailed Nov. 9, 2019, 7 pages.
Extended European Search Report for App. No. 21172995.9, dated Jul. 9, 2021, 8 pages.
Extended European Search Report for App. No. 23177809.3, mailed Sep. 25, 2023.

\* cited by examiner

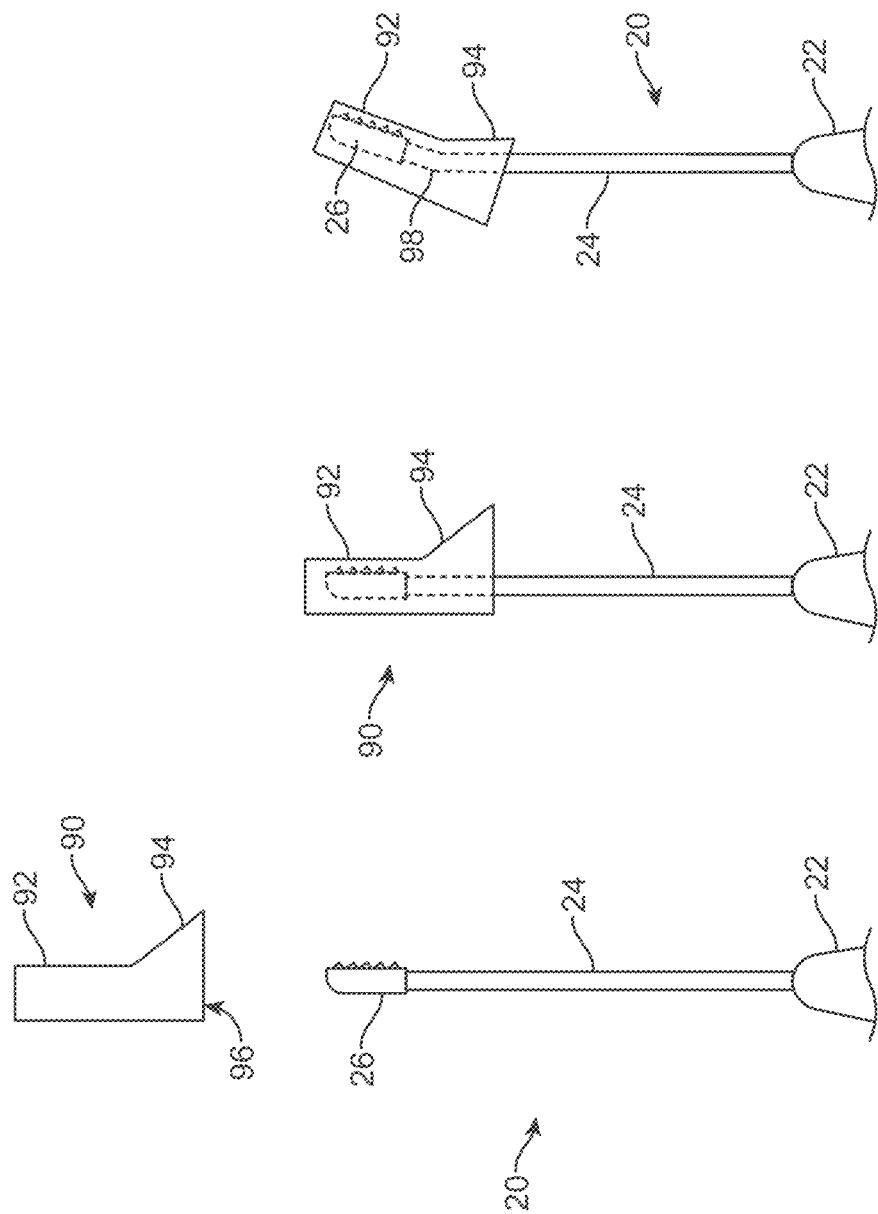

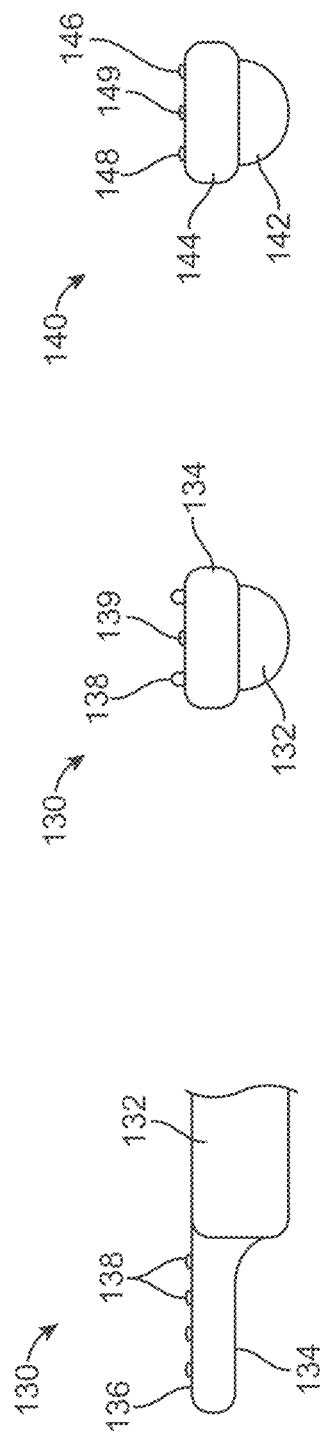

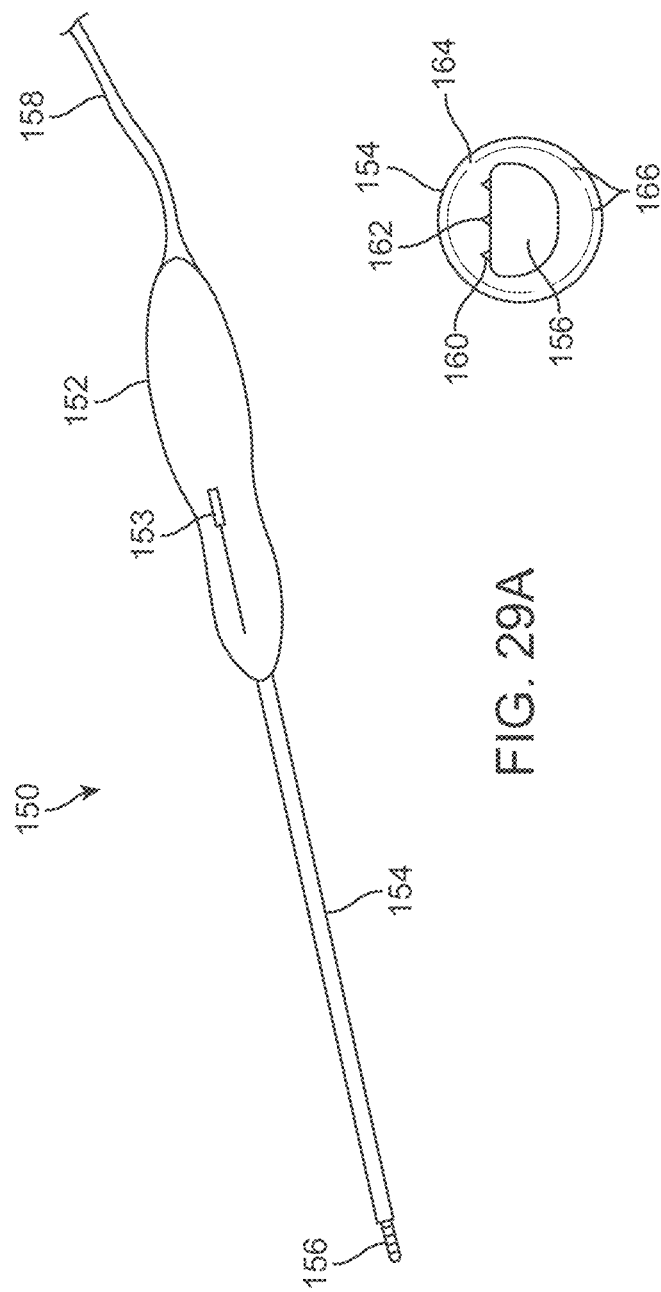

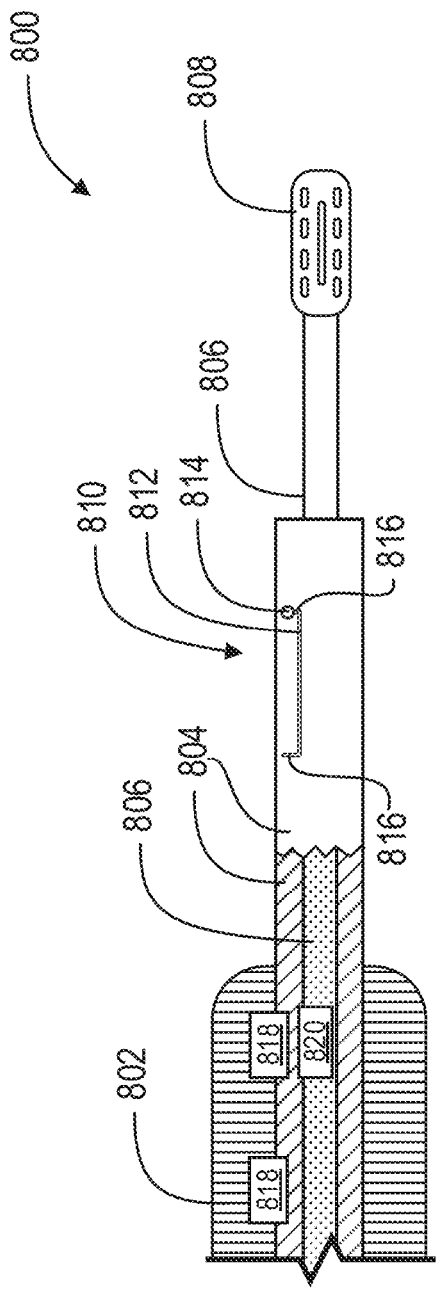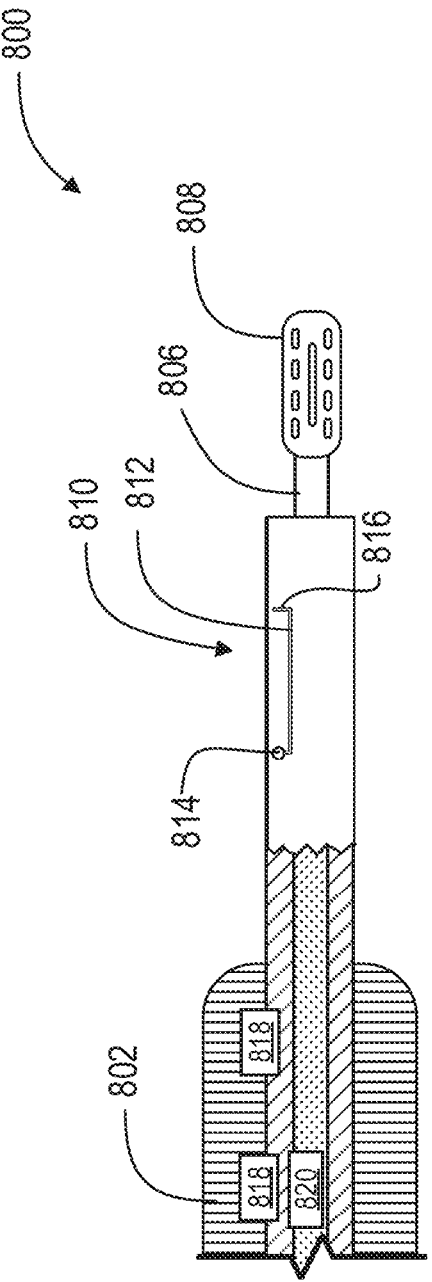

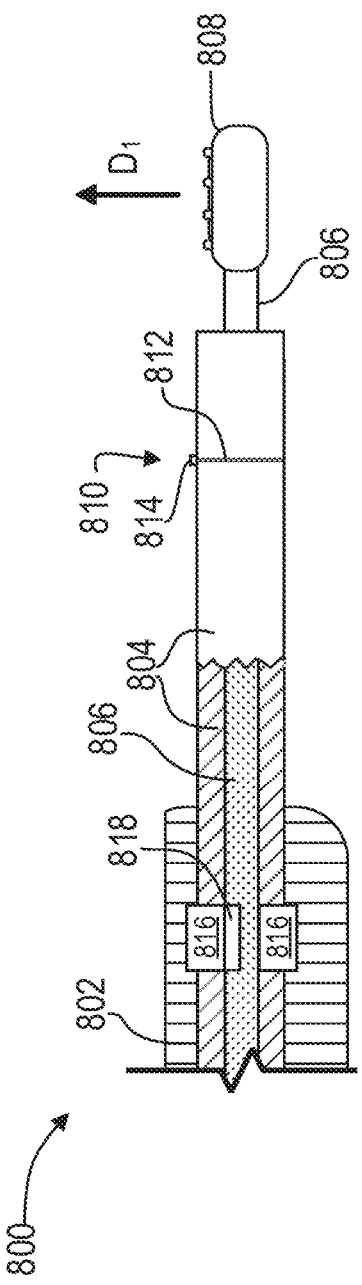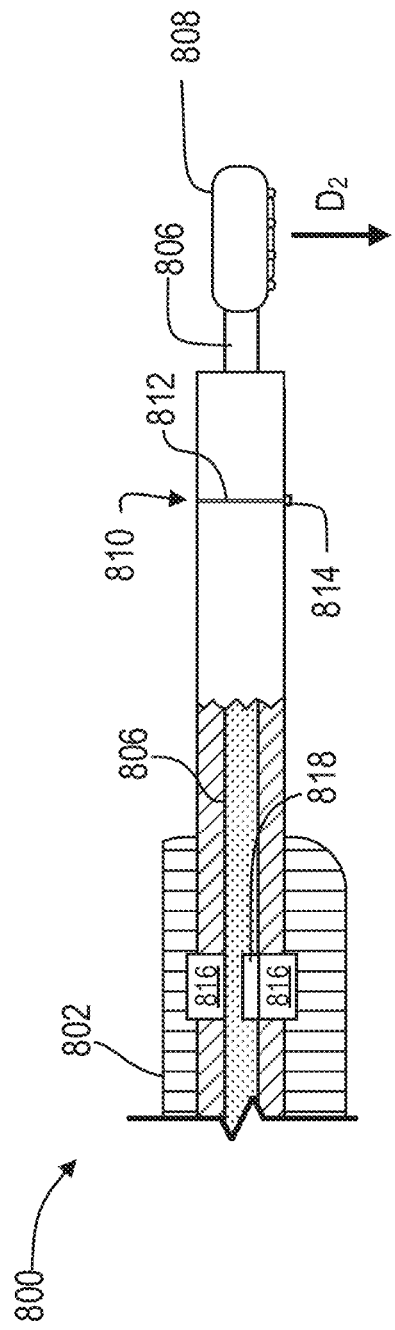
FIG. 36A
FIG. 36B

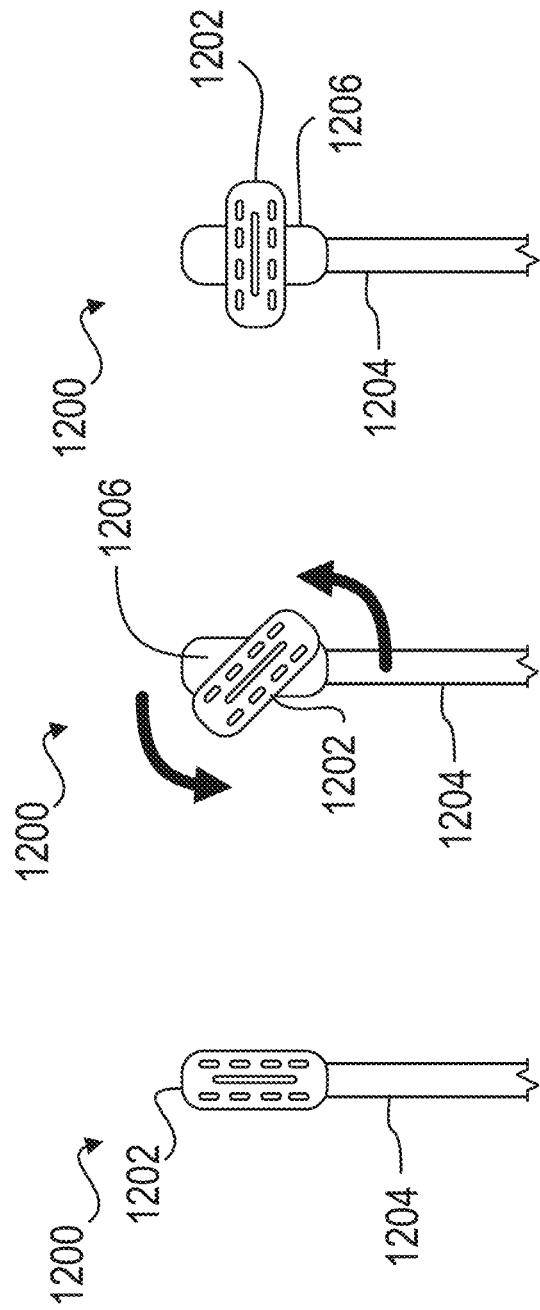

NASAL NEUROMODULATION DEVICES AND METHODS

FIELD

The present application is related to medical devices and methods. More specifically, the application is related to devices and methods for treating nerves in the nasal cavity.

BACKGROUND

Allergic rhinitis (AR) and bronchial asthma affect 20% to 40% of the world's population. These two conditions significantly impair patients' quality of life and increase the social and economic burdens of individuals and societies. The joint incidence of rhinitis and asthma and their mutual influence on each other have been documented in many studies, and the concept of "one airway, one disease" was proposed in 1997. Numerous studies confirmed that rhinitis precedes asthma in 6%-20% of cases. A provocative bronchial challenge with allergens that is responsible for AR in susceptible asthma patients can elicit asthma, and these responses have closely linked bronchial asthma with AR. Clinical data have demonstrated that effective treatment of AR can reduce the severity or frequency of allergic asthma flare-ups.

Although medical therapy is successful for many patients with AR, some patients fail to respond to medical treatments. One surgical intervention for patients with severe persistent AR is called bilateral endoscopic vidian neurectomy (EVN), where the vidian nerve on both sides of the nasal cavity is cut. Vidian neurectomy may also have beneficial effects on other conditions. Unfortunately, however, EVN requires general anesthesia and cutting of bone to access the vidian nerve. The necessity of cutting bone is illustrated in FIG. 1, which shows bone cut away to expose the vidian nerve. Additionally, EVN is known to produce unwanted side effects in some patients, such as dry eye, which is quite prevalent after the procedure, and less frequently orbital bleeding or nasal cavity adhesions.

Migraine headaches are another common, debilitating medical condition with only imperfect treatments. There is some evidence that ablating nerve tissue at or near the sphenopalatine ganglion may help prevent or reduce the occurrence of migraines and/or other headaches. Again, although vidian neurectomy might be an effective treatment, the procedure is relatively invasive and carries several potential adverse side effects. Although treatments of the sphenopalatine ganglion have been attempted for treating migraines, they typically involve an implantable device or piercing through the nose from outside the patient.

Other conditions may also benefit from deactivation or modulation of nasal nerves, including the sphenopalatine ganglion and/or any of the nerves branching from it.

Therefore, it would be beneficial to have less invasive techniques for treating nerves in the nasal cavity to ameliorate asthma, migraine, other forms of headache, or other medical conditions deriving from the nasal cavity or affected by nasal nerve activity. Ideally, such less invasive techniques would not involve implants and would not require surgery performed in an operating room.

BRIEF SUMMARY

This application describes various aspects and embodiments of a device, system and method for treating nerve tissue in the nasal airway (or "nasal cavity") for addressing asthma, migraine, other headaches, or any other suitable medical condition(s). Treatment of nasal nerves is sometimes referred to in this application as "nasal neuromodulation" or "nasal neurectomy," and these terms may be used interchangeably. Generally, nasal neuromodulation may involve treating one or more nerves without completely stopping their function, while nasal neurectomy implies that all nerve function for the treated nerve(s) is cut off. At the same time, however, nasal neuromodulation may involve completely stopping the function of one or more nerves, while allowing one or more other nerves in the same area to maintain their function. Thus, as mentioned, "nasal neuromodulation" and "nasal neurectomy" may have similar meanings in various contexts. Therefore, the use of either of these terms should not be interpreted as limiting the scope of the described embodiments.

The nasal neuromodulation system described herein includes: (1) a console with an energy generator; and (2) a stylus coupled to the console via a cable. In most embodiments described in this application, the energy generator delivers bipolar radiofrequency (RF) energy. In alternative embodiments, the system may be configured to deliver another type of energy, such as but not limited to heat, laser, microwave, cryogenic cooling (removal of energy), DC current or ultrasound. The energy delivery system is designed to treat nasal nerve tissue but may also be used to perform a number of different types of nasal airway tissue treatments. For example, in one embodiment, the system may be used to reshape, reconfigure and/or change another property of tissue (such as but not limited to cartilage) in or near a nasal valve area within the nose, to reduce nasal airway obstruction or congestion and thus enhance nasal breathing. In another embodiment, the system may be used to treat soft tissue in a more posterior portion of the nasal airway to treat chronic rhinitis, allergic rhinitis, post-nasal drip and/or chronic cough. Tissues treated in such a procedure may include submucosal tissue, mucosal tissue, goblet cells and/or the like.

The devices and methods described in this application may be used to treat any suitable nasal cavity nerves to treat any targeted condition or multiple conditions. In some cases, one or more nasal nerves are treated to address a medical condition manifesting itself outside of the nasal cavity. In other cases, nasal nerves are treated to address a condition in the nasal cavity. And in some cases, nasal nerve modulation may be used to treat a condition inside the nasal cavity and a condition outside the nasal cavity.

In various embodiments, any nasal cavity nerve, or combinations of nasal cavity nerves, may be treated, such as but not limited to any of the nerves shown in FIG. 1 and including posterior nasal nerves, vidian nerve, vidian nerve branches, occipital nerve, trigeminal nerve, trigeminal nerve branches, the sphenopalatine ganglion, and any nerve(s) branching off the sphenopalatine ganglion. One or more nerves may be targeted to treat any of a number of different conditions or combinations of conditions, such as but not limited to chronic or allergic rhinitis, vasomotor rhinitis, bronchial asthma (referred to herein as "asthma"), chronic obstructive pulmonary disease (COPD), airway inflammation, nasal obstruction and/or congestion, eye inflammation and allergic conjunctivitis, allergies, migraine, other headaches (e.g., cluster headaches, nasal contact point headaches, etc.), tinnitus, dizziness, vertigo, dry eye, excessive tearing, empty nose syndrome, pain (e.g., facial nerve pain, trigeminal neuralgia, complex regional pain syndrome, etc.), anxiety, mood disorders, middle ear conditions such as otitis media, herpes zoster, paroxysmal hemicranias, cancer of the head or neck, reduction of chemical mediators that lead to any of the above-listed conditions, and/or the like. This application will often refer to treatment of nasal nerves to ameliorate asthma and/or migraine headaches, but these are only two examples of conditions that the devices and methods described herein may be used to address. For brevity, the list of possible conditions that may be treated will not be repeated when describing each embodiment.

In one aspect of the present disclosure, a system for treating nasal airway tissue to ameliorate one or more symptoms of rhinitis, asthma and/or other conditions includes a console and a stylus. The console includes a housing, a radiofrequency energy generator in the housing, a computer processor in the housing, and an outlet on the housing. The stylus includes a handle, a cable connected to a first end of the handle, including a connector at an opposite end for connecting to the outlet, a shaft extending from a second end of the handle, and a distal tip extending from a distal end of the shaft. The distal tip includes a treatment surface, two rows of bipolar radiofrequency electrodes on the treatment surface, and a temperature sensing member on the treatment surface.

In some embodiments, the shaft of the stylus is malleable. In some embodiments, each of the two rows of bipolar electrodes comprises four electrodes. In some embodiments, the treatment surface is convex. The system may optionally also include an additional stylus having a shaft with a different length than that of the shaft of the stylus. In some embodiments, the shaft of the stylus has a length of 3.75 inches. In some embodiments, the handle of the stylus has a depression aligned with the treatment surface of the distal tip. Some embodiments may further include a power cord coupled with the console and a foot pedal coupled with the console for activating the stylus. The system may also include an injection needle for injecting anesthetic fluid into the nasal airway tissue.

In another aspect of the present disclosure, a kit for treating nasal airway tissue to ameliorate one or more symptoms of rhinitis, asthma and/or other conditions includes a console, a stylus and at least one additional component. The console may include a housing, a radiofrequency energy generator in the housing, a computer processor in the housing, and an outlet on the housing. The stylus may include a handle, a power cord connected to a first end of the handle, the power cord including a connector at an opposite end for connecting to the outlet, a shaft extending from a second end of the handle, and a distal tip extending from a distal end of the shaft. The distal tip includes a treatment surface, two rows of bipolar radiofrequency electrodes on the treatment surface, and a temperature sensing member on the treatment surface. The additional component(s) may be a packet of conductive gel, a curved anesthesia needle, a shaft bending tool and/or instructions for use.

In some embodiments, the shaft of the stylus is malleable and has a width of 4 millimeters to 5 millimeters. In some embodiments, the two rows of bipolar radiofrequency electrodes comprises four electrodes, and wherein the electrodes are protruding, non-piercing electrodes. In some embodiments, the treatment surface is convex. In some embodiments, the shaft of the stylus has a length of 3.75 inches, and the kit includes an additional stylus having a shaft with a length of less than 3 inches. Optionally, the kit may also include a power cord coupled with the console, a foot pedal attachable to the console for activating the console to supply radiofrequency energy to the stylus, and an on/off button on the stylus for activating the console to supply the radiofrequency energy to the stylus. In some embodiments, the kit includes a foot pedal attachable to the console for activating the console to supply radiofrequency energy to the stylus, and the console is configured to receive a reset signal from the foot pedal to reset the console after an error message. In some embodiments, the shaft bending tool is configured to bend the shaft at only one location along the shaft and prevents bending of the shaft beyond a predefined maximum bending angle.

In another aspect of the present disclosure, a method for treating a nasal airway to ameliorate one or more symptoms of rhinitis, asthma and/or other conditions in a patient involves activating a radiofrequency console attached to a stylus, bending a shaft of the stylus in at least one location to a desired angle, advancing a distal tip of the radiofrequency stylus into a nostril of the patient, applying pressure against nasal mucosa lining the nasal airway with a treatment surface of the distal tip, and delivering radiofrequency energy from one set of bipolar electrodes on the treatment surface of the distal tip to a second set of bipolar electrodes on the treatment surface, to treat tissue underlying the nasal mucosa, where the tissue comprises at least one nasal nerve. The method also involves contacting the distal tip with an additional tissue in another location within the nasal airway, delivering radiofrequency energy to the additional tissue, and removing the distal tip of the stylus from the nostril.

Optionally, the method may also involve moving the distal tip to multiple additional locations within the nasal airway and delivering radiofrequency energy to nasal airway tissue at the multiple additional locations. In some embodiments, the console automatically stops delivering radiofrequency energy to the stylus after a maximum total number of treatments has been reached for the patient, and wherein the maximum total number of treatments is in a range from 16 to 24 treatments. In some embodiments, the radiofrequency energy is delivered for 12 seconds. Optionally, the method may also involve sensing a temperature of the nasal mucosa with a temperature sensing member located on the treatment surface of the distal tip. The method may also involve automatically shutting off delivery of radiofrequency energy from the console to the stylus if the sensed temperature is above a predefined acceptable maximum temperature.

In some embodiments, the at least one nasal nerve includes a posterior nasal nerve. In some embodiments, bending the shaft involves bending the shaft at a first location within one inch of the distal tip. Optionally, the shaft may be bent at a second location between one half and one third of a total length of the shaft, measured from a connection point of the shaft with a handle of the stylus. In other embodiments, the shaft may be bent at additional or alternative locations along the shaft. In some embodiments, the method involves injecting an anesthetic fluid into the nasal mucosa before advancing the distal tip of the stylus into the nostril, to enhance conduction of the delivered radiofrequency energy through the mucosal tissue. In some embodiments, delivering the radiofrequency energy ablates the at least one nasal nerve. In various embodiments, the additional tissue may include an inferior turbinate, a middle turbinate, a superior turbinate, a nasal septum, and/or a septal swell body. In some embodiments, bending the shaft is performed before activating the radiofrequency console.

In another aspect of the present disclosure, a device for treating nasal airway tissue to ameliorate one or more symptoms of rhinitis includes a handle, a power cord connected to a first end of the handle and including a connector at an opposite end for connecting to an outlet of a radiofrequency console, a shaft extending from a second end of the handle, a distal tip extending from a distal end of the shaft, and an expandable treatment member. The distal tip includes a treatment surface, two rows of bipolar radiofrequency electrodes on the treatment surface, and a temperature sensing member on the treatment surface. The expandable treatment member is configured to be advanced out of a distal end of the shaft and includes at least one pair of bipolar radiofrequency electrodes.

In some embodiments, the shaft of the stylus is malleable and has a width of 4 millimeters to 5 millimeters. In some embodiments, the expandable treatment member is an expandable wire component disposed in a lumen of the shaft of the stylus when not in use and advanced out of the lumen, over the distal tip of the stylus, to allow the expandable treatment member to expand for use in treatment. In other embodiments, the expandable treatment member is an expandable wire component disposed in a lumen of the shaft of the stylus when not in use and advanced out of the lumen, through an opening in the distal tip of the stylus, to allow the expandable treatment member to expand for use in treatment. In yet other embodiments, the expandable treatment member is cryotherapy balloon disposed in a lumen of the shaft of the stylus when not in use and advanced out of the lumen, over the distal tip of the stylus, to allow the cryotherapy balloon to be inflated for use in treatment.

In one aspect of the present disclosure, a device for treating airway tissue may include: a handle; an outer shaft fixedly attached to the handle; an inner shaft disposed in the outer shaft; and a treatment element attached to a distal end of the inner shaft and configured to deliver energy to the airway tissue to modify at least one property of the tissue. The inner shaft is free to move in at least one direction within the outer shaft to change an orientation of the treatment element from a first configuration to a second configuration. In some embodiments, for example, the inner shaft is free to translate, relative to the outer shaft, and thus the first configuration is a retracted configuration, and the second configuration is an extended configuration. Alternatively or additionally, the inner shaft may be free to rotate in a plane perpendicular to a length of the inner shaft, relative to the outer shaft. Thus, the treatment element faces in a first direction in the first configuration and a second direction in the second configuration. Again, in some embodiments, the inner shaft is free to rotate and translate, relative to the outer shaft.

In some embodiments, the treatment element is adjustable relative to the inner shaft, to change an orientation of the treatment element. For example, the treatment element may be configured to rotate in a plane parallel to a length of the inner shaft. Optionally, the device may further include a position sensor for determining whether the treatment element is in the first configuration or the second configuration. In some embodiments, the device may be configured to operate using a first set of parameters when the treatment element is in the first configuration and a second set of treatment parameters when the treatment element is in the second configuration.

The outer shaft may include a lumen, and the inner shaft may be disposed in the lumen. The device may further include a fixation mechanism configured to lock the device in the first configuration or the second configuration. In some embodiments, the device is configured for treating nasal airway tissue, and the treatment element is sized to fit through a nostril of a nose.

In another aspect of the present disclosure, a method for treating an airway may involve: obtaining an airway treatment device; actuating a fixation mechanism of the treatment device; transitioning the device from a first configuration to a second configuration; positioning a treatment element within the airway proximate an airway tissue to be treated; and applying energy to the airway tissue with the treatment element. Using this method, the airway tissue at least partially maintains a modified property after the treatment element is removed and the airway tissue heals.

In one embodiment, actuating the fixation mechanism involves moving a peg out of a landing. In some embodiments, transitioning the device from the first configuration to the second configuration may involve moving an inner shaft of the treatment device relative to an outer shaft of the treatment device. For example, the inner shaft may be rotated and/or translated, relative to the outer shaft, according to various embodiments. In some embodiments, transitioning the device from the first configuration to the second configuration may involve adjusting a position of the treatment element relative to a shaft of the treatment device. For example, adjusting the position of the treatment element may involve rotating the treatment element in a plane parallel to a longitudinal axis of the shaft.

In some embodiments, the airway tissue treated with the method is nasal airway tissue. In such embodiments, positioning the treatment element may involve advancing the treatment element through a nostril.

In another aspect of the present disclosure, an airway treatment system may include a treatment device configured to deliver energy to tissue within an airway to modify at least one property of the tissue and a control system coupled to the treatment device. The control system may be configured to determine whether the treatment device is in a first configuration or a second configuration and modify one or more treatment parameters of the treatment device, based on whether the treatment device is in the first configuration or the second configuration.

In some embodiments, the treatment device further includes a supporting feature removably coupled to an attachment mechanism. The supporting feature may include, but is not limited to, a clamp portion, an electrode array, an incision forming device, a second treatment device, a positioning device, or a sensor array. In some embodiments, the treatment device may include a sensor configured to determine a configuration of the treatment device. The control system may then be configured to determine whether the treatment device is in the first configuration or the second configuration based on an output of the sensor.

In some embodiments, the device may include a fixation mechanism. In some embodiments, the device may include a treatment element having multiple selectable treatment portions. In such embodiments, the first configuration may involve an inner shaft of the plurality of selectable treatment portions being selected, and the second configuration may involve an outer shaft of the plurality of selectable treatment portions being selected.

In another aspect of the present invention, a method for treating migraine headaches in a patient may involve: activating a console attached to a radiofrequency stylus; advancing a distal tip of the radiofrequency stylus into a nasal cavity of the patient; contacting nasal mucosa lining the nasal cavity with a treatment surface of the distal tip; and delivering radiofrequency energy from one set of bipolar electrodes on the treatment surface of the distal tip to a second set of bipolar electrodes on the treatment surface, to treat at least one nerve underlying the nasal mucosa. Treating the at least one nerve involves modulating activity of the at least one nerve to treat the migraine headaches. The method may involve any of the features and steps described above. In some embodiments, the method may further involve pushing the treatment surface against the nasal mucosa lining to treat a contact point in the nasal cavity.

These and other aspect and embodiments are described in further detail below, in references to the attached drawing figures.

BRIEF DESCRIPTION OF THE DRAWINGS

FIG. 25A-25C illustrate a method of using a different shaft bending tool to bend a stylus, according to an alternative embodiment;

FIGS. 27A and 27B are side and front views, respectively, of a distal end of a nasal airway tissue treatment stylus, according to an alternative embodiment;

FIG. 28 is a front view of a distal end of a nasal airway tissue treatment stylus, according to an alternative embodiment;

FIGS. 29A and 29B are perspective and front views, respectively, of an alternative embodiment of a nasal airway tissue treatment stylus that includes an expandable wire electrode component;

FIGS. 35A and 35B are partial cutaway, side views of a multi-position airway treatment device having an adjustable length, according to one embodiment;

FIGS. 36A and 36B are partial cutaway, side views of a multi-position treatment device having a rotatable treatment element, according to one embodiment;

FIGS. 39A-39C are bottom views of a distal portion of a treatment device having a rotatable treatment element, according to one embodiment;

DETAILED DESCRIPTION

Figure 1:
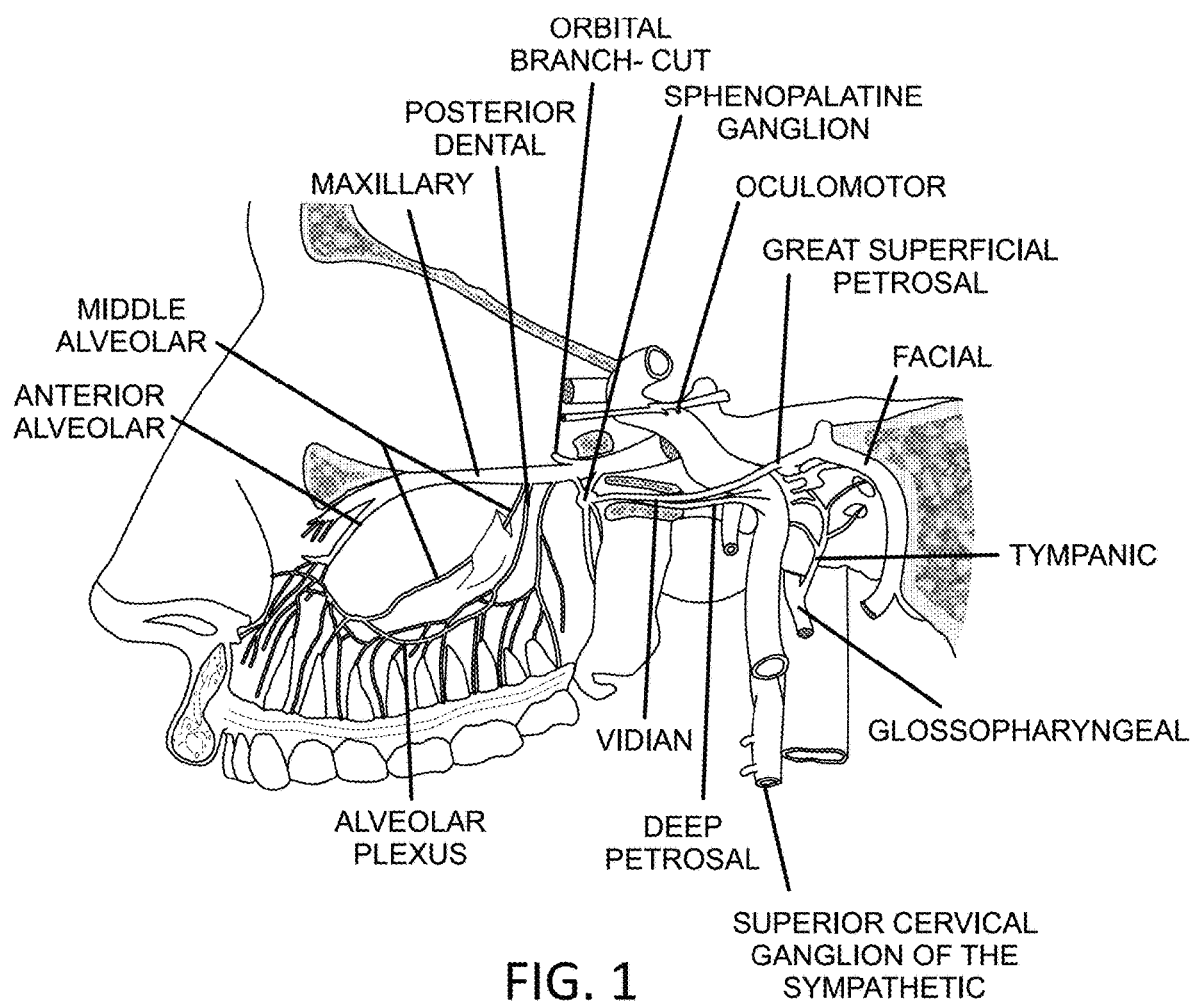
FIG. 1 is a sagittal view of a human nasal cavity, illustrating the lateral wall and nasal nerves.

Referring to FIG. 1, a sagittal cross-section of a human nasal cavity is shown. In this cross-sectional view, bone has been removed to illustrate the path of multiple different nerves, such as the vidian nerve and the sphenopalatine ganglion. According to various embodiments and examples described herein, any nerve or combination of nerves may be treated, such as but not limited to the vidian nerve, vidian nerve branches, the sphenopalatine ganglion and/or any nerve branching from the sphenopalatine ganglion, such as the posterior nasal nerve (descending from the sphenopalatine ganglion in FIG. 1 but not labeled). In an actual patient, the posterior nasal nerve and other nasal nerves lie under the nasal mucosa that lines the walls of the nasal cavity and thus are not visible on the surface, as they are in FIG. 1. This anatomical drawing is provided for illustration purposes only.

Any of the system and device embodiments described below may be used to treat any nerve or nerves in the nasal cavity and/or any additional anatomical structures in the nasal cavity, to treat any condition inside or outside of the nasal cavity. To address underlying nerves or to address other tissues, various areas and structures, such as but not limited to the following, may be treated: lateral walls of the nasal cavity, nasal septum, septal swell bodies, inferior turbinates, middle turbinates, superior turbinates, inferior meatus, middle meatus, and superior meatus. Typically, the devices described herein will contact mucosa overlying one or more of these various areas or structures, and energy will be delivered through the mucosa to address nerves and/or other underlying, submucosal tissues.

As mentioned above, the systems, devices and methods described herein may be used for treating any nerve or combination of nerves to address any suitable condition or multiple conditions. Treatment is performed in the nasal cavity but may address conditions originating outside the nasal cavity, inside the nasal cavity or both. Some of the conditions that may be treated by the embodiments described herein include, but are not limited to, rhinitis, asthma, COPD, airway inflammation, nasal obstruction and/or congestion, eye inflammation and allergic conjunctivitis, allergies, migraine headaches, other headaches (e.g., cluster headaches, nasal contact point headaches, etc.), tinnitus, dizziness, vertigo, dry eye, excessive tearing, empty nose syndrome, pain (e.g., facial nerve pain, trigeminal neuralgia, complex regional pain syndrome, etc.), anxiety, mood disorders, middle ear conditions such as otitis media, herpes zoster, paroxysmal hemicranias, cancer of the head or neck, and reduction of chemical mediators that lead to any of the above-listed conditions.

Figure 2:
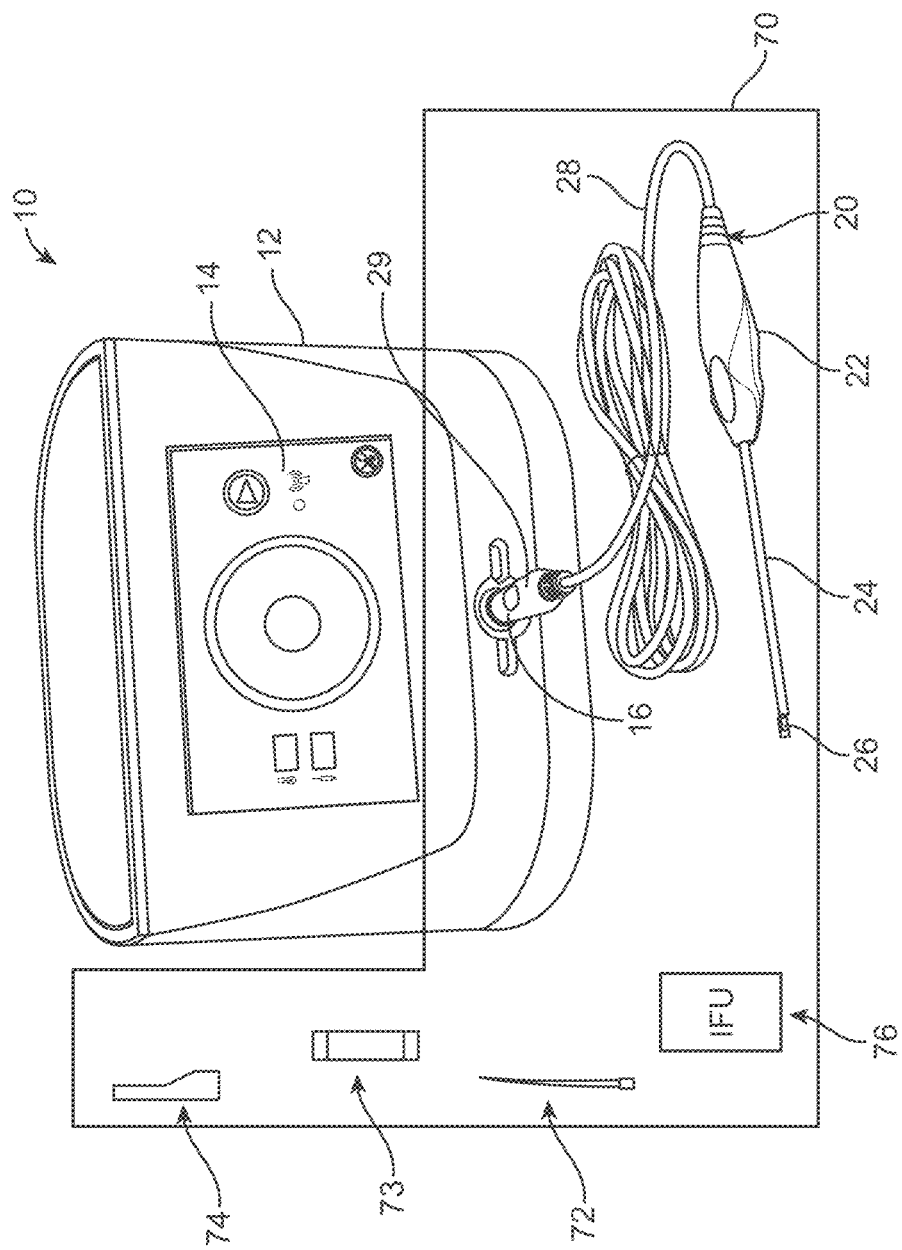
FIG. 2 is a front perspective view of an RF electrosurgical system for treating nasal airway tissue, according to one embodiment.

Referring to FIG. 2, in one embodiment, a nasal airway tissue treatment system 10 includes two primary components: a console 12 and a radiofrequency stylus 20 (or simply "stylus"). The console 12 includes a display 14, an RF generator and electronics (inside the console 12 and thus not visible), and an outlet 16 into which the stylus 20 is plugged. The stylus 20 includes a handle 22, a shaft 24, a distal tip 26 (also referred to as a "treatment element"), a cable 28 and a connector 29 for connecting the stylus 20 with the outlet 16. Many features of the console 12 and the system 10 in general are described further below.

The console 12 is a reusable device, which is designed and intended for use with multiple patients. The stylus 20, on the other hand, is a single-patient, single-use, disposable device. In some embodiments, the stylus 20 may be provided as part of a stylus kit 70, which may include a curved anesthesia needle 72, a packet of conductive gel 73, a shaft bending tool 74 and/or instructions for use 76 (or "IFU"). All of these kit components are optional, and any embodiment of the stylus kit 70 may include fewer items or additional items, without departing from the scope of the invention. In some embodiments, the stylus 20 may be provided by itself for use with the console 12. The stylus 20 may be used for multiple treatments on the same patient at the same time—for example multiple treatment areas in a nostril and/or treatment of both nostrils—and then is disposed of after use on that patient. In an alternative embodiment, the stylus 20 may be sterilizable and reusable.

Figure 5:
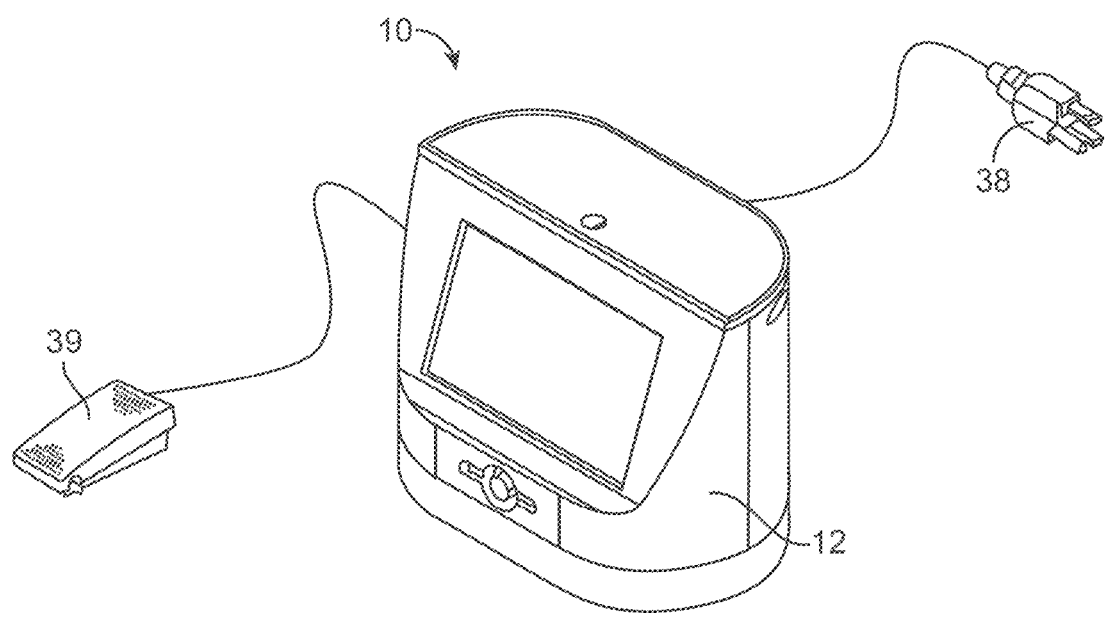
FIG. 5 is a perspective view of the console of FIG. 2, shown connected to an on/off foot pedal and a power cord, according to one embodiment.

In some embodiments, the nasal airway tissue treatment system 10 may be provided with one or more additional components or accessories. For example, and as shown in FIG. 5, the system 10 typically includes a power cord 38 and a foot switch 39, both of which attach to the console 12. As another example, the stylus 20 illustrated in FIG. 2 has a relatively long shaft 24, configured for use in the posterior portion of the nasal cavity to treat nerves to treat rhinitis, asthma and/or other conditions. In one embodiment, one or more additional styluses may be provided with the system 10, for performing other procedures. For example, a second stylus with a shorter shaft for addressing tissue in the nasal valve, closer to the front of the nose, may be provided. The curved anesthesia needle 72 for injecting anesthetic into the nasal mucosa is another optional component. The curved needle 72 is designed to be stiffer than a spinal needle and is curved to allow a physician to easily access and inject anesthesia into an area near the back of the nasal cavity. The curved needle 72 can also be reinforced to prevent bending or bowing during injection. The system 10 may also be provided with one or more conductive gel packets 73, for application to the distal tip 26 of the stylus, to enhance contact of the distal tip 26 with nasal mucosa. The bending tool 74 will be described further below and may be used by the physician to bend the shaft 24 of the stylus 20 in one or more locations. Any other suitable accessories or components may be added to the treatment system 10, according to alternative embodiments.

Figure 3:
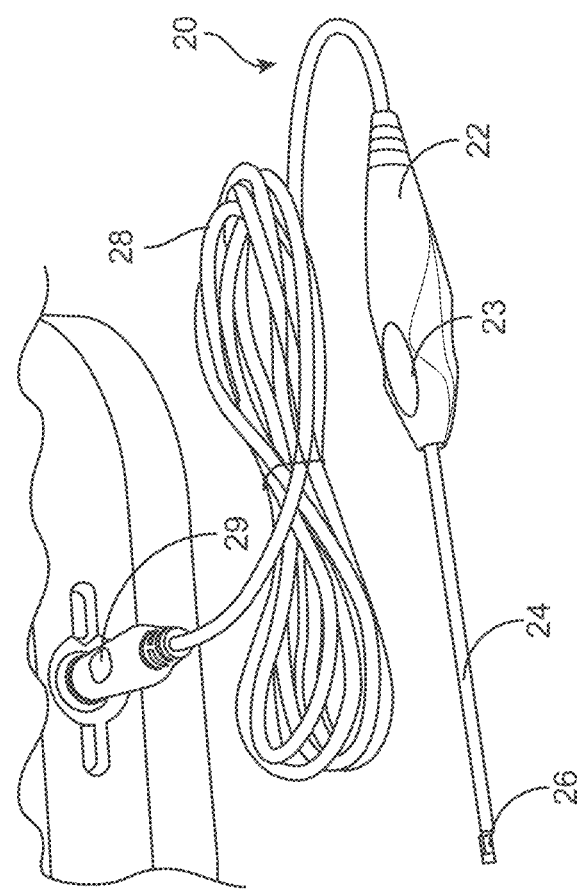
FIG. 3 is a close-up perspective view of the stylus, cable and connector of the system of FIG. 2.

FIG. 3 is a more detailed view of the RF stylus 20. In this embodiment, the handle 22 includes an oval depression 23, which faces in the same direction as the treatment surface of the distal tip 26. The oval depression 23 allows the physician user to know the orientation of the treatment surface at all times and may also be used as a finger or thumb rest. In some embodiments, an on/off button may be positioned where oval depression 23 is illustrated on handle 22. This on/off button may be used to activate the stylus and thus provide RF energy to the electrodes at the distal tip 26. In some embodiments, the physician may use the handle on/off button as an alternative to a foot pedal for this purpose. The stylus shaft 24 may have any length suitable for reaching the posterior portion of the nasal cavity where the posterior nasal nerves reside. In one embodiment, for example, the shaft 24 is approximately 3.75 inches long, from its connection to the distal tip 26 at one end to its connection with the handle 22 at the opposite end. In alternative embodiments, the shaft 24 may have different lengths, for example between about 3 inches and about 4 inches in embodiments designed for addressing a posterior portion of the nasal cavity, and between about 1 inch and about 3 inches in embodiments designed for addressing an anterior portion of the nasal cavity, such as the nasal valve. The shaft 24 may also have any suitable width (or "diameter"). For example, in some embodiments, the shaft may have a width of about 4 mm to about 5 mm. The shaft 24 will be described in further detail below.

Figure 4A:
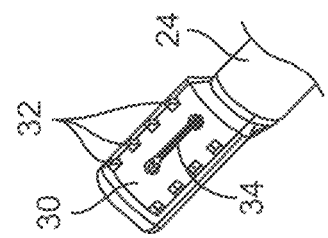
FIGS. 4A and 4B are side and top perspective views, respectively, of a distal tip (or "treatment element") of the stylus of FIGS. 2 and 3.
Figure 4B:
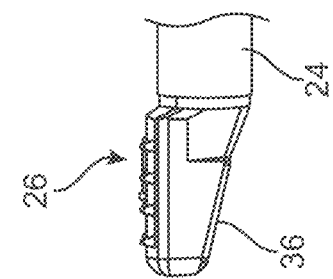

Referring now to FIGS. 4A and 4B, the distal tip 26 is shown in detail. The distal tip 26 includes a treatment surface 30 (or "tip face"), two rows of four bipolar RF electrodes 32, and a thermocouple 34 between the electrodes 32. As illustrated in FIG. 4A, the bottom surface 36 of the distal tip 26 may be tapered or slanted, to give the distal end of the distal tip 26 a narrower profile to facilitate insertion and advancement of the distal tip 26 into the nostril and to the posterior portion of the nasal cavity. The treatment surface 30 is made of a non-conductive material (e.g., plastic) and may have a slightly convex shape, as illustrated, or may alternatively be flat, concave, or more convex than the shown in FIG. 4B. The slightly convex shape may help ensure contact of the electrodes 32 and the thermocouple 34 with mucosal tissue during use. In alternative embodiments, the thermocouple 34 may be removed or replaced by a different type (or shape or number) of temperature sensor(s). The thermocouple 34 is used to measure temperature of the mucosa and provide the measurements to a processor in the console 12, which can in turn automatically adjust whether and how much RF energy is delivered to the stylus 20. In some embodiments, the distal tip 26 or a portion thereof may be translucent, to facilitate visualization of target tissue and/or nasal mucosa.

FIGS. 27A and 27B are side and front views, respectively, of a distal portion of an alternative embodiment of a nasal airway tissue treatment stylus 130. In this embodiment, the height or thickness of the distal tip 134 is thinner than in the previously described embodiment and thinner than the shaft 132 of the stylus 130. The distal tip 134 includes a treatment surface 136, four pairs of bipolar RF electrodes 138, and a thermocouple 139. The thinner distal tip 134 may facilitate passage of the tip 134 through a nostril and around nasal cavity anatomy for positioning at a treatment site in a posterior portion of the nasal cavity. In all other respects, the distal tip 134 may include any of the features of the embodiment described above.

FIG. 28 is a front view of yet another embodiment of a nasal airway tissue treatment device 140. This embodiment also includes a shaft 142 and a distal tip 144, which in turn includes a treatment surface 146, four pairs of bipolar RF electrodes 148 and a thermocouple 149. In this embodiment, however, the electrodes and thermocouple are flat, rather that rounded or pointed. They protrude only slightly from the treatment surface 146. This further helps reduce the overall height or thickness of the distal tip 144 and thus makes it easier to advance the tip 144 through the nostril and nasal cavity. In some embodiments, the electrodes and thermocouple may even be completely flush with the treatment surface.

FIG. 5 illustrates the console 12 of the nasal airway tissue treatment system 10, along with a power cord 38 and a foot switch 39, both of which plug into the back of the console 10. The foot switch 39 is used by the physician to activate the stylus 20 during a procedure. In alternative embodiments, the handle 22 of the stylus 20 may include an on/off button or switch, in addition to or as an alternative to the foot switch 39.

Figure 6:
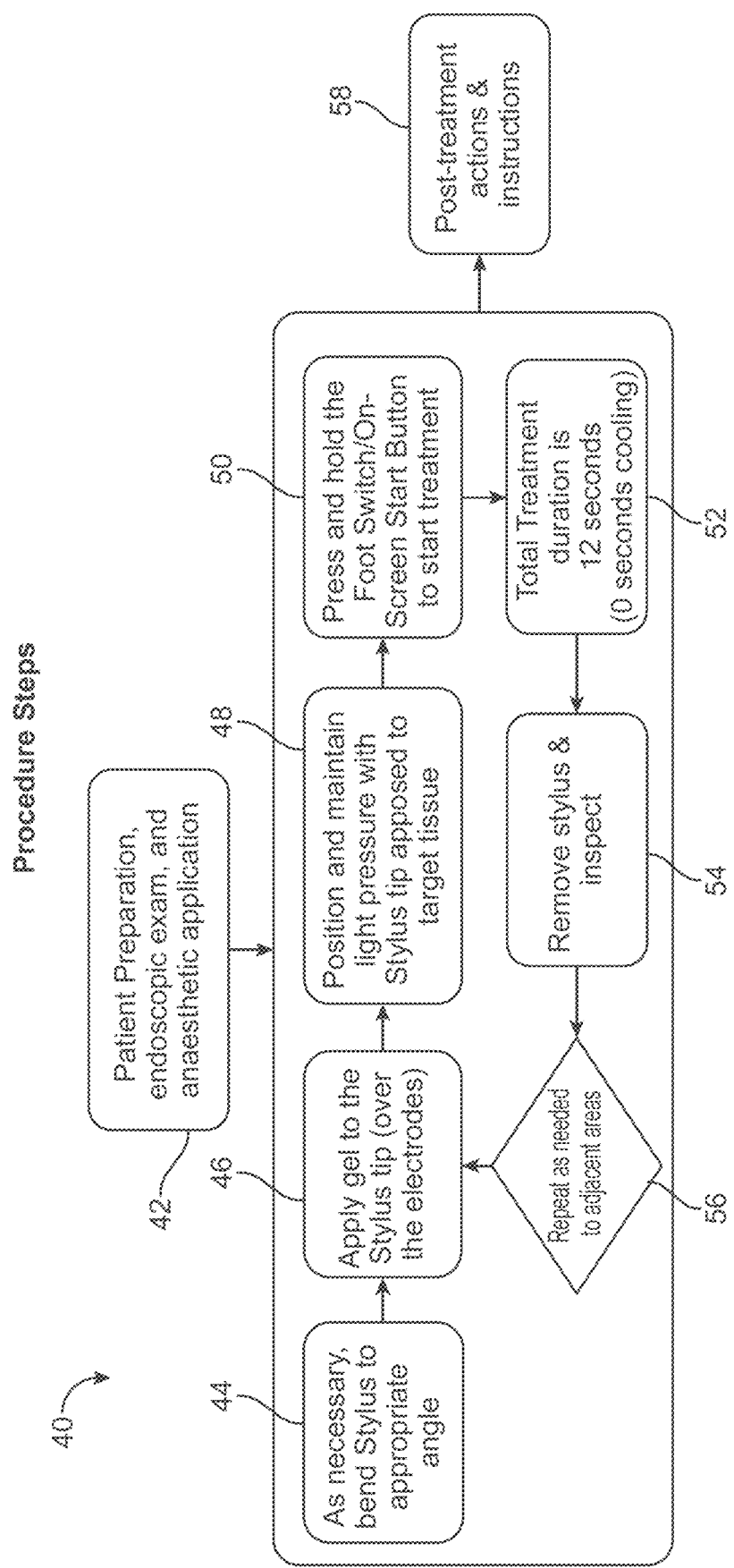
FIG. 6 is a flow chart illustrating a method for treating nasal airway tissue using a system such as that shown in FIGS. 2-5, according to one embodiment.

FIG. 6 illustrates one embodiment of a method 40 for using the treatment system 10 to treat nerve tissue (and/or other tissues) in the nasal cavity to treat asthma and/or any other suitable condition. In this embodiment, the method 40 includes the steps of: preparing the patient 42, such as with local anesthesia and an endoscopic examination of the nasal cavity; bending the stylus 44, if desired (explained further below); applying conductive gel to the stylus distal tip 46, over the electrodes; advancing the distal tip of the stylus into the nostril and contacting it with the treatment area 48, then maintaining light pressure with the distal tip against the treatment tissue; pressing and holding down the foot switch 50 to start the treatment; continuing to hold down the foot switch for twelve seconds 52 (the treatment time in this embodiment); removing and inspecting the distal tip 54; and repeating 56 steps 46, 48, 50 and 52 as necessary, to treat additional treatment areas. In one embodiment, for example, it is recommended that at least three, twelve-second treatments are performed along the course of the posterior nasal nerve. Any other number of treatments may be performed, however, in alternative embodiments.

Additionally, each treatment may last a different period of time than 12 seconds, such as between 10 seconds and 60 seconds in various embodiments. When a treatment on a patient is complete, a final step may be to provide post-treatment actions and instructions to the patient 58.

The method may be repeated for as many treatment areas as desired. In some embodiments, the stylus 20, the console 12 or both may be configured to allow only a certain number of treatments for any given stylus 20. This may help prevent reuse of the stylus 20 on multiple patients or overtreatment of any one patient. For example, in one embodiment, the stylus 20 may only be able to deliver sixteen 12-second treatments. In other embodiments, the stylus 20 may be capable of delivering ten to thirty 12-second treatments, for example. In yet other embodiments, the stylus 20 may be capable of delivering any number of treatments, but the console 12 is able to identify each stylus 20 and count or identify how many treatments have been applied with that stylus 20. The console 12 may be configured to shut down or simply not deliver RF energy to a stylus 20 that has reached its maximum number of allowed treatments. In other embodiments, a single stylus 20 may be used with the console 12 to deliver as many treatments on one patient as desired, but once the treatment on that patient is completed, the stylus 20 is rendered inoperable for use with any additional patient(s). Inoperability may be conferred by a computer chip in the handle 22 of the stylus 20, or alternatively the console 12 may destroy or alter a portion of the stylus 20 when the stylus 20 is unplugged from the console 12 or at some other point at the end of a treatment.

In some embodiments, the nasal airway tissue treatment stylus 20 may be used for treating several different types of target tissue in one patient. Before treating posterior nasal nerve tissue, after treating that tissue, or both, one or more additional tissues may be treated. Such tissues include mucosa, nerves and/or other tissue of any one of the nasal turbinates, nasal swell bodies, the nasal septum, and mucus producing cells anywhere in the nasal cavity. Therefore, the treatment method illustrated in FIG. 6 may be added to by treating any one or more of these additional tissues. Physicians may often treat the inferior and/or middle turbinate before or after proceeding with the steps in FIG. 6 to treat posterior nasal nerve tissue.

Figure 7:
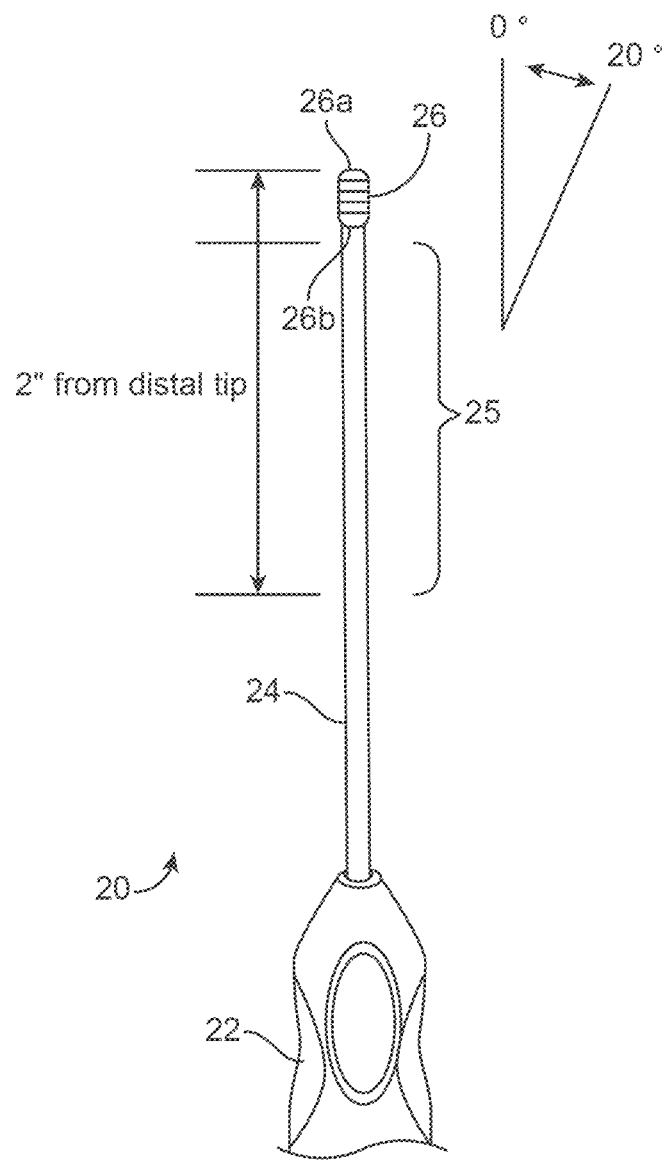
FIG. 7 is a top view of the stylus of FIGS. 2-4B, illustrating a method for bending the shaft of the stylus, according to one embodiment.

Referring next to FIG. 7, a portion of the stylus 20 is shown, illustrating features of the shaft 24. In this embodiment, the shaft 24 is malleable, so that it can be bent by a physician user and retain the bent shape during use. This may be especially advantageous, for example, in helping the physician advance the distal tip 26 of the device around anatomical structures to a posterior target area in the nasal cavity. As illustrated in FIG. 7, the distal tip 26 has a distal edge 26a and a proximal edge 26b. Just proximal to the proximal edge 26b of the distal tip 26 is a bend section 25 of the shaft 24. The bend section 25 is approximately 2 inches in length in this embodiment, and it is the section of the shaft that is recommended for bending. Physician users may be instructed, for example with instructions for use provided with the system 10, to bend the shaft 24 only within the bend section 25 and not too close to the distal tip 26. This may help prevent weakness at the areas where the shaft 24 is connected to the distal tip 26 and the handle 22. In the embodiment shown, the entire shaft 24 is made of a malleable material, but in alternative embodiments only a portion of the shaft 24 might be malleable, such as the bend section 25.

The shaft 24 may be manually bent by the physician to the appropriate bend angle. While bending, the physician should support the stylus 20 by the shaft 24, not by the handle 22 or the distal tip 26. The bend should be formed in the orientation the electrodes 32 are facing. The shaft 24 may be bent to any suitable angle. In one embodiment, however, it is recommended that the shaft 24 only be bent to a maximum of approximately 20 degrees away from the longitudinal axis of the stylus 20. Again, this limit on bending may help maintain the structural integrity of the stylus 20. Bending the shaft 24 at all is entirely optional, and some or even all physicians might decide not to bend the shaft 24 at all. In alternative embodiments, the shaft 24 might be rigid and not malleable. In general, all parts of the stylus 20, other than the electrodes 32 and the thermocouple 34, may be made of non-conductive materials, such as any suitable plastic or polymer.

Figure 24C:
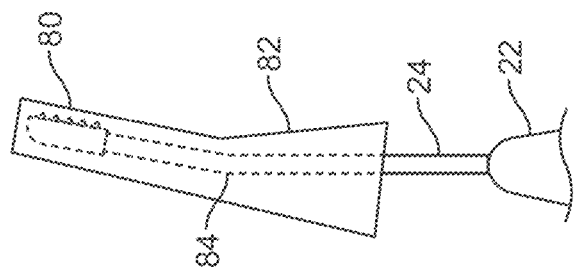
FIG. 24A-24C illustrate a method of using a shaft bending tool to bend a stylus, according to one embodiment.
Figure 24B:
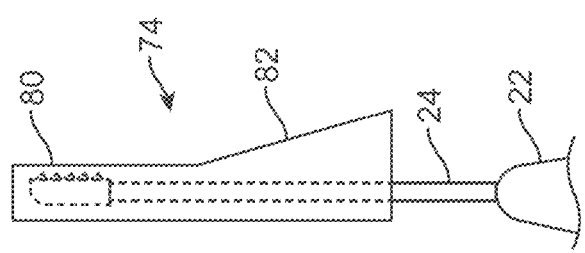
Figure 24A:
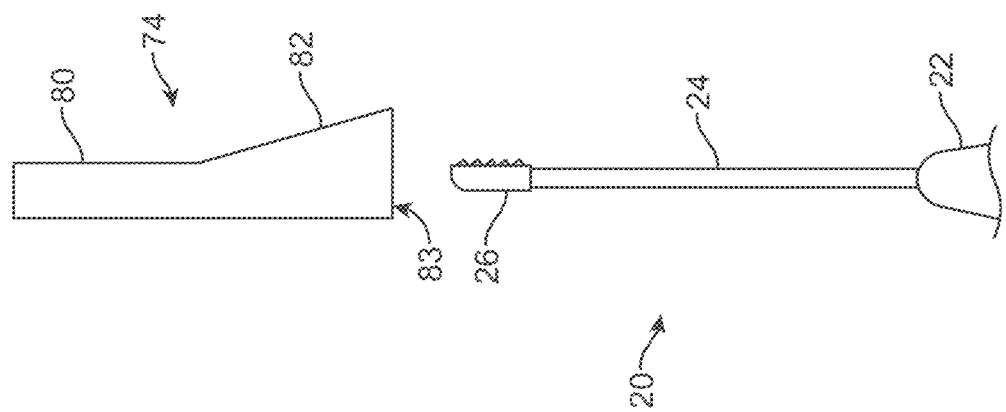

Referring to FIGS. 24A-24C, in some embodiments a bending tool 74 may be provided for bending the shaft 24 of the stylus 20. In this embodiment, the bending tool 74 includes a narrow distal portion 80, a wide proximal portion 82, and an opening 85 into which the distal tip 26 and a portion of the shaft 24 enter. As illustrated in FIG. 24B, the bending tool 74 may first be slid down onto the stylus 20. The bending tool 74 may then be tilted, as shown in FIG. 24C, to form a bend 84 in the shaft 24. The bending tool 74 may have any suitable length, to bend the shaft 24 in a desired location. For example, in some embodiments the bending tool 74 is designed to bend the shaft 24 somewhere between one third and one half of the length of the shaft measured from the handle 22. Alternative embodiments of the bending tool 74 may have any other suitable size, shape and configuration for bending a shaft 24 of a stylus 20.

FIGS. 25A-25C illustrate the use of another embodiment of a shaft bending tool 90. In this embodiment, the shaft bending tool 90 includes a narrow distal end 92, a wide proximal end 94, and an opening 96, as with the previous embodiment. In this embodiment, however, the shaft bending tool 90 is significantly shorter than the previously illustrated embodiment. As illustrated in FIG. 25C, this shorter bending tool 90 creates a bend 98 in the shaft 24 that is much closer to the distal tip 26. Physicians may want to bend the shaft 24 of the stylus 20 in different locations. Thus, in some embodiments more than one size or shape of bending tool 74, 90 may be provided. A physician may select one bending tool 74, 90 to make one bend, or she may use two (or more) different bending tools 74, 90 to make multiple bends in the shaft 24.

Figure 26:
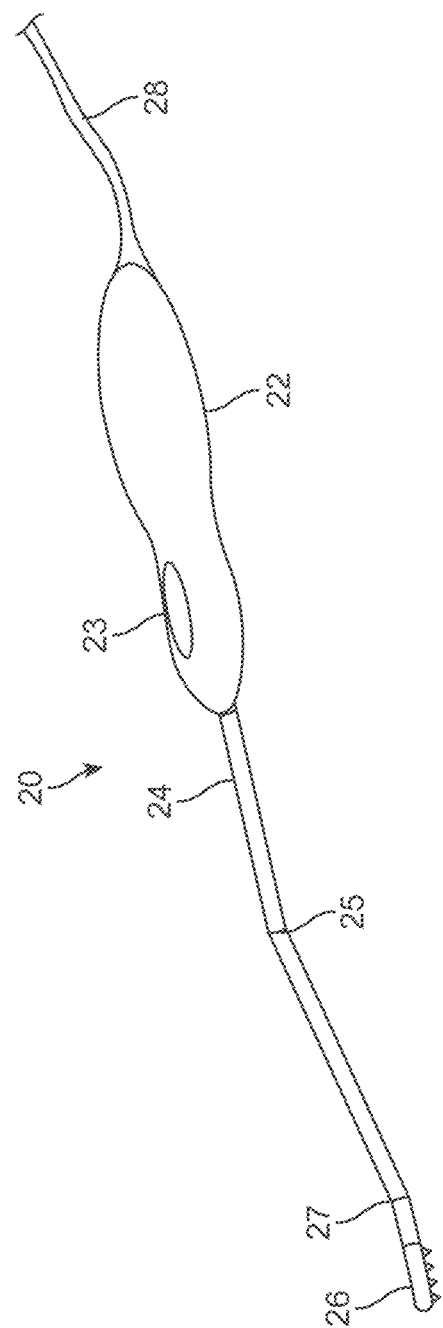
FIG. 26 is a perspective view of a nasal airway tissue treatment stylus with two bends in the shaft and bend markers on the shaft, according to one embodiment.

Referring to FIG. 26, as just mentioned, in some cases a physician may bend the shaft 24 of the stylus 20 at two different locations, forming for example a proximal bend and a distal bend. In some embodiments, the shaft 24 may include one or more proximal bend markers 25 and one or more distal bend markers 27. Bend markers 25, 27 may be located at any location along the length of the shaft 24 and may be made with paint, etched into the surface, or by any other means. In the illustrated embodiment, two bends are made to give the shaft 24 a bayonet shape, as desired by some physicians to navigate around anatomical structures in the nasal cavity while still positioning the treatment surface of the distal tip 26 in full contact with nasal mucosa on the lateral wall of the nasal cavity. It bears repeating that in various alternative embodiments, the shaft 24 may include any number of bend markers 25, 27 at any locations and/or the shaft 24 may be bent (with or without markers) at any suitable location or at multiple locations.

In various embodiments, the shaft 24 may be either more or less malleable, depending on the desired stiffness versus bendability of the shaft 24. In some embodiments, only certain portions of the shaft, which are designed to be bent, are malleable, while others are stiff. Or certain portions may be more malleable than others. More malleable sections may have a thinner wall than less malleable sections and/or the shaft 24 may be made of different materials in different sections. The latter is likely to complicate manufacturing and increase expense, however, so in at least some embodiments the shaft 24 is made of one piece of material, such as a metal hypotube. In such cases, differences in malleability may be achieved via differences in wall thickness.

Figure 8:
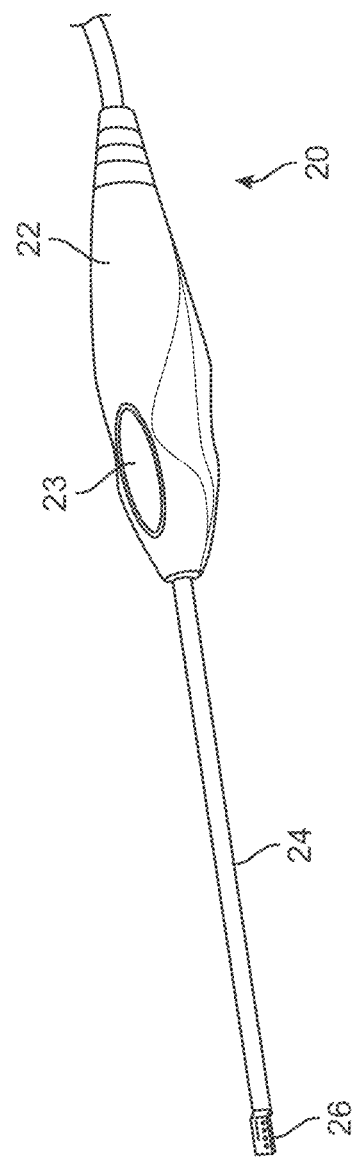
FIG. 8 is a perspective view of the stylus of FIGS. 2-4B and 7, illustrating an indicator on the handle showing the direction of treatment, according to one embodiment.

FIG. 8 is another illustration of the stylus 20, showing how the oval depression 23 on the top of the handle 22 aligns with the treatment surface 30 of the distal tip 26. This allows the physician to always know what direction the treatment surface 30 is facing. The oval depression 23 is configured to provide an ergonomic location for placement of the physician's thumb, but depressions of different shapes may be used in different embodiments. Other alternative embodiments may use any other suitable directional indicator on the handle 22 and/or a proximal portion of the shaft 24, to show direction of the distal tip 26.

Figure 9:
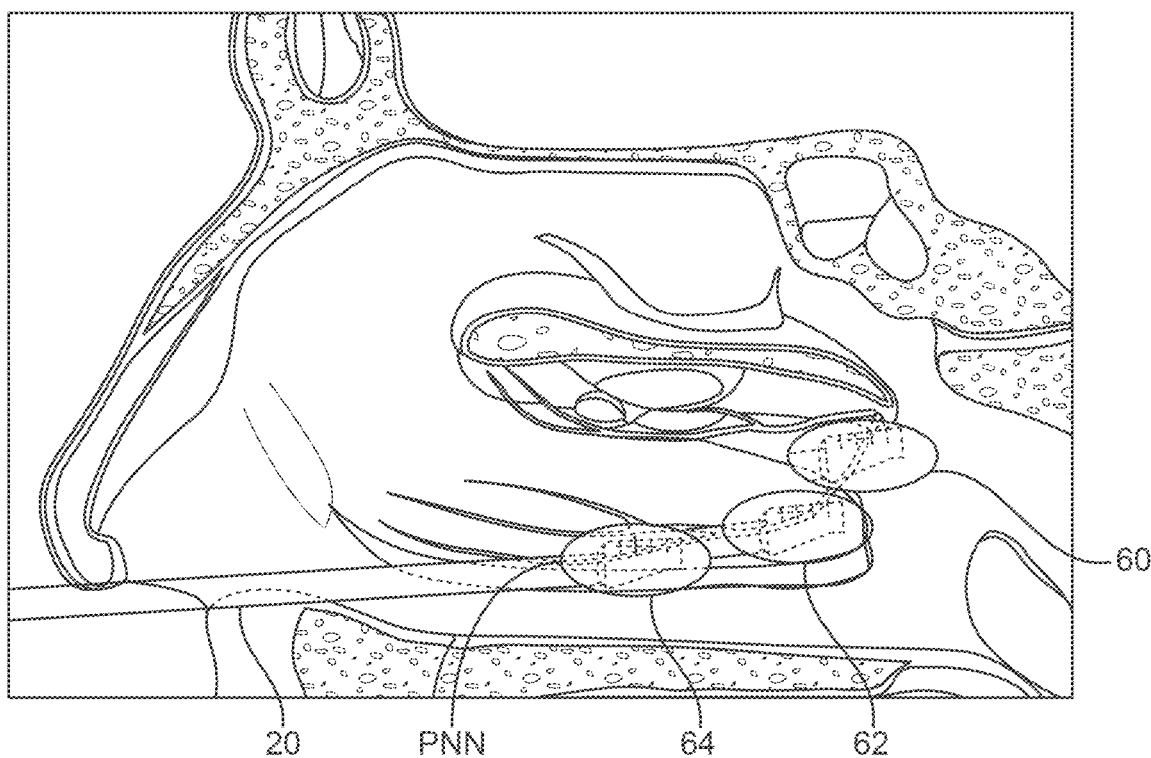
FIG. 9 is a sagittal view of a human nasal cavity, illustrating a method for treating the posterior nasal nerve with the stylus described herein, according to one embodiment.

FIG. 9 is the same sagittal view of the nasal cavity as in FIG. 1, with the additional illustration of three treatment areas for treating the nasal cavity with the stylus 20. In this embodiment, the stylus 20 has been used to deliver RF energy to a first target location 60, a second target location 62 and a third target location 64, all of which fall along the path of the posterior nasal nerve PNN. Additional treatments may optionally be provided in the same general area and/or in different areas of the nasal cavity. For example, some physicians may use the stylus 20 to treat a nasal septum, a septal swell body, an inferior turbinate and/or other soft tissue(s) in the nose, all as part of the same treatment on one patient. FIG. 9 is thus provided for illustrative purposes only.

Figure 10A:
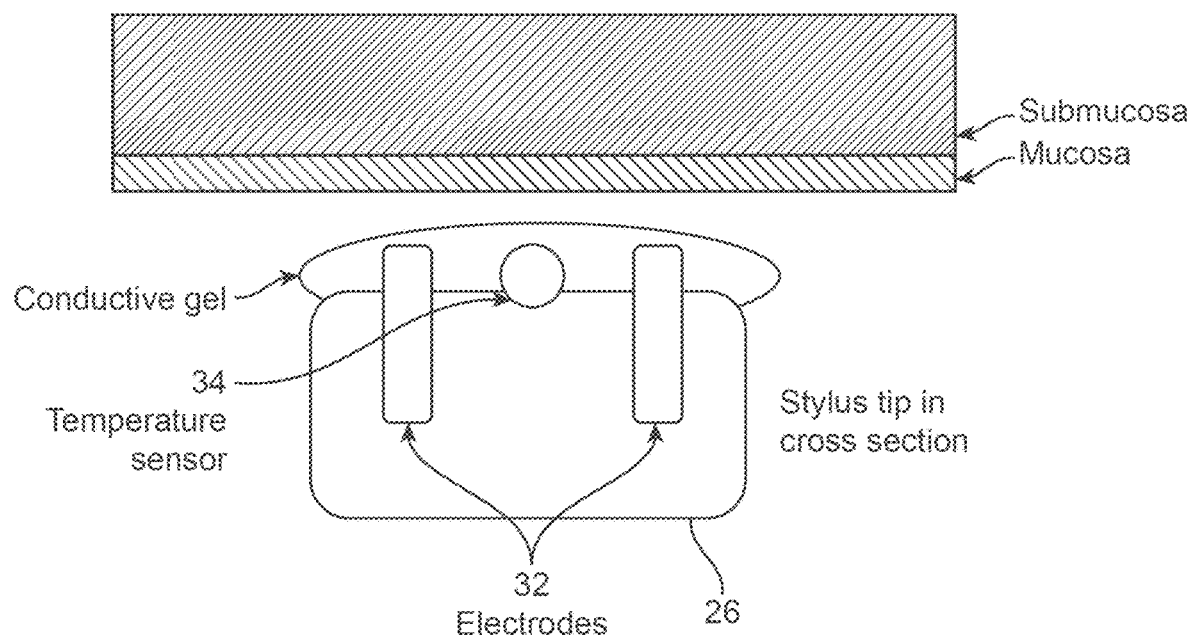
FIGS. 10A and 10B illustrate a method for addressing, contacting and treating nasal tissue, according to one embodiment.
Figure 10B:
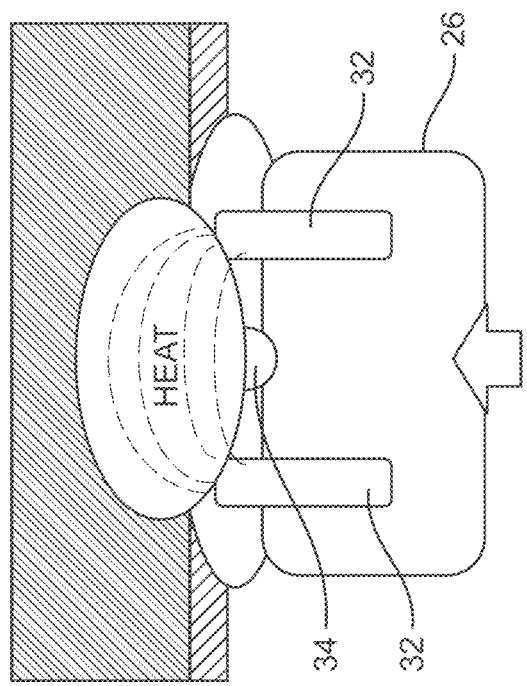

Referring to FIGS. 10A and 10B, two steps of the method for using the nasal tissue treatment system 10 are illustrated diagrammatically. In FIG. 10A, the distal tip 26 of the stylus 20 is shown in an end-on, cross-sectional view, showing two electrodes 32 and the temperature sensor 34. The distal tip 26 has conductive gel on its treatment surface 30 and is in position within the nostril, near the mucosa. Next, as illustrated in FIG. 10B, the physician contacts the mucosa with the distal tip 26, applies gentle pressure against the mucosa, and presses the foot pedal to activate the stylus 20 and deliver RF energy from one set of electrodes 32, through the mucosa, to target tissue(s) in the submucosa, and back to a second set of electrodes 32. This process generates heat and treats the target submucosal tissues, such as the posterior nasal nerve and/or other nerves. Again, the treatment may be timed by the console 12, which may automatically stop the delivery of RF energy after a preset time, such as 12 seconds in one embodiment. The thermocouple 34 measures the temperature of the mucosa it is contacting, and the system 10 uses this measurement to automatically shut off the system 10 if a temperature is too high or otherwise outside of a preset range of acceptable temperatures.

Figure 11:
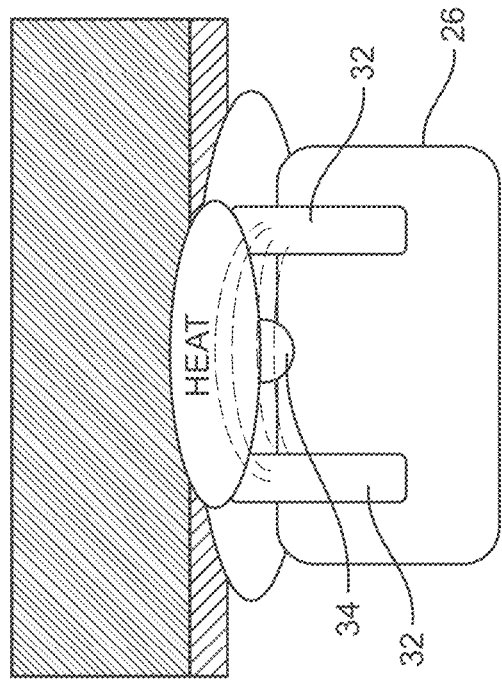
FIG. 11 illustrates an improper treatment contact with nasal mucosa.

FIG. 11 illustrates the distal tip 26 in a similar position as shown in FIG. 10B, but in this case the physician is not applying gentle pressure to the mucosa with the distal tip 26. As illustrated, it is possible that without application of pressure, the applied RF energy will not penetrate the submucosa to reach the desired target tissue. In some embodiments, the stylus 20 is designed to determine whether adequate pressure is being applied and to only activate the electrodes 32 when the pressure is applied.

According to various embodiments, the console 12 of the treatment system 10 may include default settings and custom settings. Default settings may include, for example, a power output of 4 Watts, a treatment temperature of 60 degrees Celsius, and a treatment time of 12 seconds. Custom settings may allow a physician to customize settings. For example, such settings could provide for power of 3-5 Watts with an increment interval of 1 Watt, a treatment temperature of 50-70 degrees Celsius with an increment interval of 5 degrees Celsius, and a treatment time of 10-12 seconds with an increment interval of 2 seconds. These are merely examples, however, and should not be interpreted as limiting.

Anesthesia protocols for anesthetizing the patient's nasal cavity are largely up to the physician, and many different protocols are known to otolaryngologists. In some embodiments, it may be required or strongly recommended to inject anesthetic into the mucosa and/or submucosa in the target area(s), in order to help direct the RF current delivered by the stylus 20. This may be helpful in some embodiments, because fluid such as anesthetic is generally conductive for RF.

Figure 12:
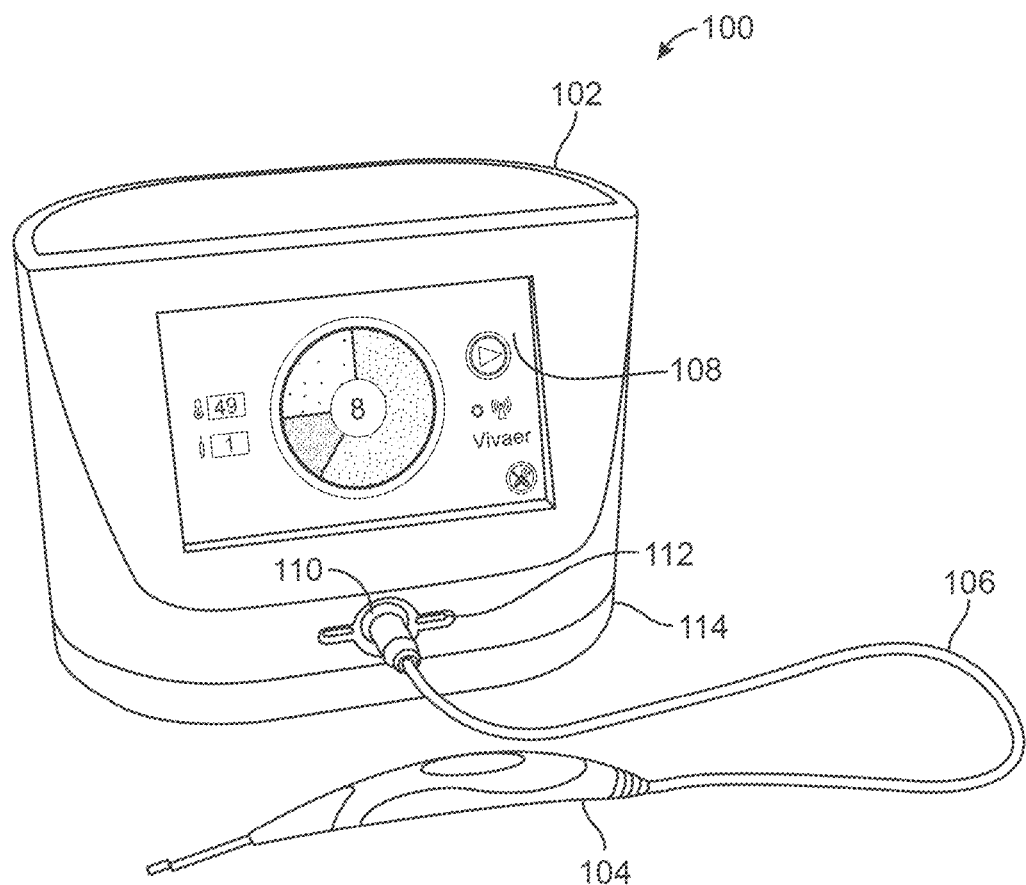
FIG. 12 is a perspective view of an electrosurgical system, according to an alternative embodiment.

Referring to FIG. 12, another example of an RF electrosurgical system 100 is illustrated. In this embodiment, the stylus 104 has a shorter shaft, such as might be used in treating tissues in the nasal valve area. Thus, the treatment times and protocols, as well as the displays on the display screen 108 of the console 102, are designed for nasal valve treatment. These features may be adjusted/altered for treatment of nasal nerve(s) to treat rhinitis, asthma and/or other conditions. As mentioned above, in alternative embodiments the electrosurgical system 100 may be modified to provide and deliver any other suitable type of energy, rather than RF. In this example, the RF electrosurgical system 100 includes a console 102, an RF delivery stylus 104, and a cable 106 connecting the stylus 104 to the console 102. The console 102 houses an RF generator, a processor and various electronics, none of which is visible in FIG. 1. The word "console," in this disclosure, is meant to encompass the terms "generator," "box" and any other commonly used terms to describe an electrosurgical system console or generator. The parts of the console 102 that are visible in FIG. 1 include a touch screen display 108, a stylus connection port 110, an "RF ON" indicator light 112, and a bottom ring 114. The touch screen display 108 serves as the main user interface for interacting with the console 102 and will be described further below. The stylus connection port 110 allows a connection end (or "connector") of the stylus 104 to be plugged into it. The stylus connection port 110 is configured to accept only the connection end of the stylus 104 and will not accept or work with counterfeit or other devices. In some embodiments, electronics inside the console 102 may include a stylus identification safety feature that identifies the stylus 104 when it is plugged into the stylus connection port 110. Such a safety feature may, for example, automatically shut down (or disable powering on) the console 102, if a user tries to plug in a device other than the stylus 104.

The RF ON indicator light 112 indicates when RF energy is being delivered through the stylus connection port 110 to the stylus 104. The bottom ring 114, in this embodiment, lights up when the console 102 is powered on. This lighted ring 114 is an optional feature. Both the RF ON indicator light 112 and the lighted bottom ring 114 may have any color or colors of light. In one embodiment, for example, the RF ON indicator light 112 is blue, and the bottom ring 114 lights up with a white light. This is merely one example, however, and any suitable lighting configuration and combination of colors may be used in alternative embodiments.

Figure 13:
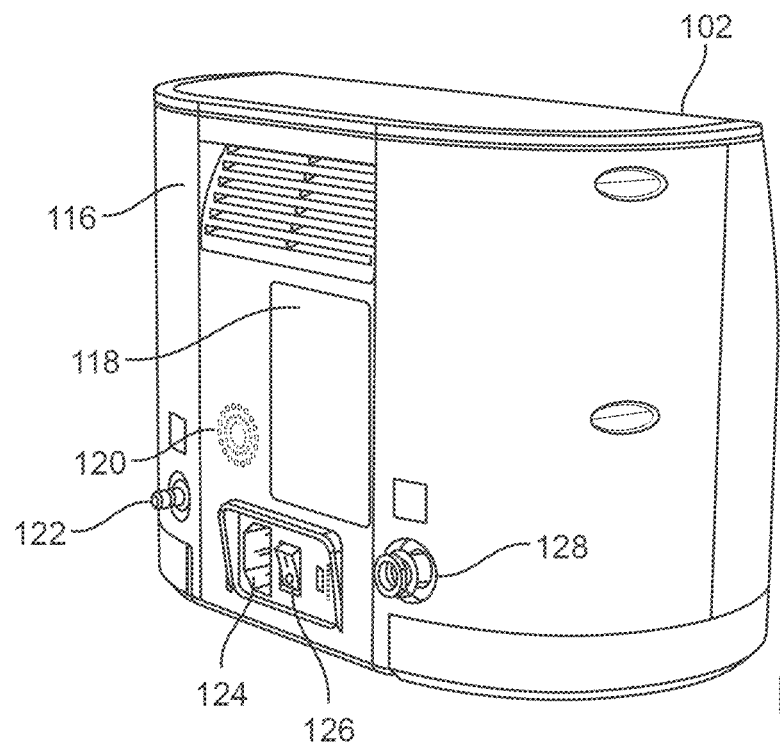
FIG. 13 is a rear perspective view of the console of the electrosurgical system of FIG. 12.

FIG. 13 shows the back of the console 102. In this embodiment, the console 102 includes an air vent 116, a product label area 118, a speaker 120, an equipotential ground connection port 122, a main power connection port 124, a main power switch 126 and foot switch connection port 128. The equipotential ground connection port 122 is provided at the back of the device.

Figure 14A:
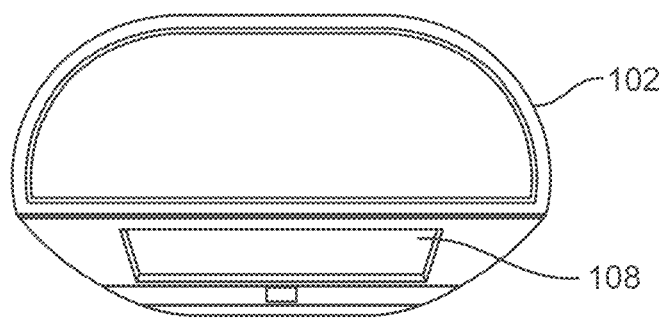
FIGS. 14A-14C are top, front and side views, respectively, of the console shown in FIGS. 12 and 13.
Figure 14B:
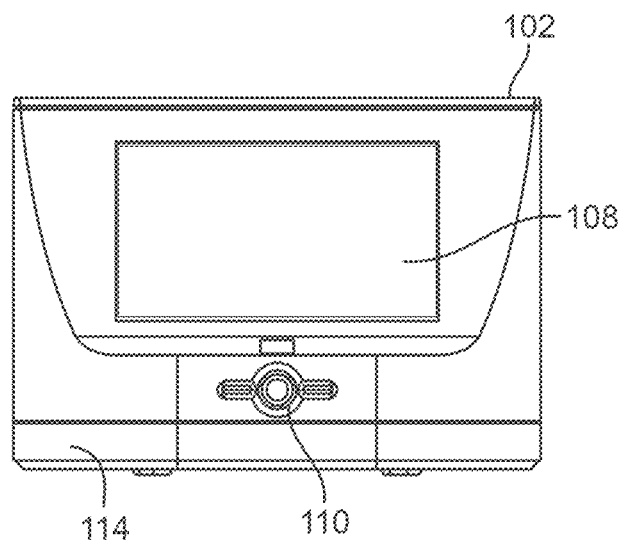
Figure 14C:
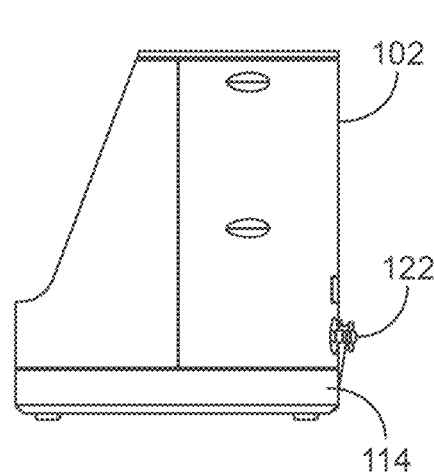

FIGS. 14A-14C are top, front and side views, respectively, of the console 102 shown in FIGS. 12 and 13.

Figure 15:
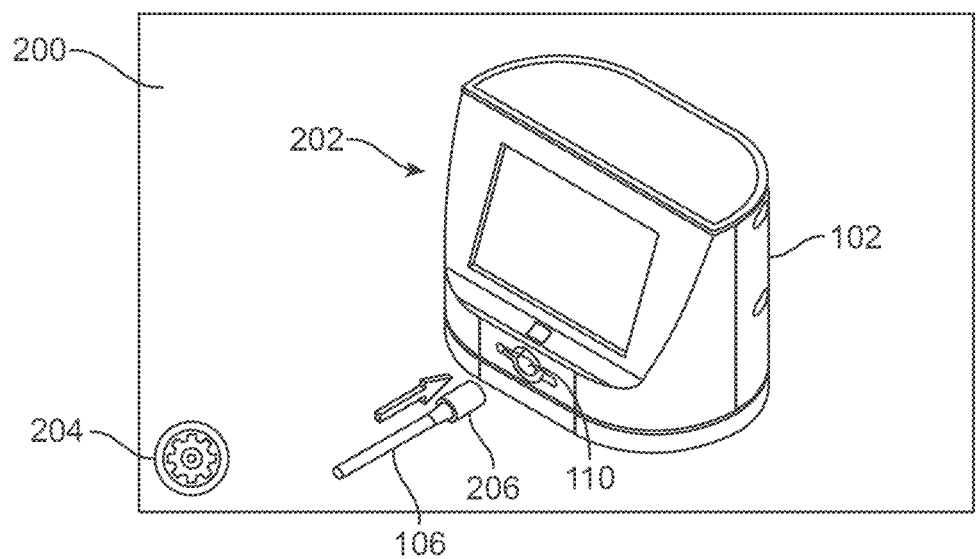
FIG. 15 is a screen shot of a standby screen display that may be displayed on an electrosurgical console, according to one embodiment.

Referring now to FIG. 15, a screen shot of one example of a standby image 200 that may be shown on the display screen 108 of the console 102 is illustrated. The standby image 200 may be displayed after the console 102 is powered on. In some embodiments, the console 102 may perform a power-on self-test before showing the standby image 200. The standby image includes a console image 202, a settings button 204 and an animated insert stylus image 206. The animated insert stylus image 206 shows the connector end of the stylus cable 106 moving toward the console stylus connection port 110. Thus, the display 200 graphically informs the user that the console 102 is ready for use, awaiting insertion of the connection end of the stylus cable 106 into the connection port 110.

Figure 16:
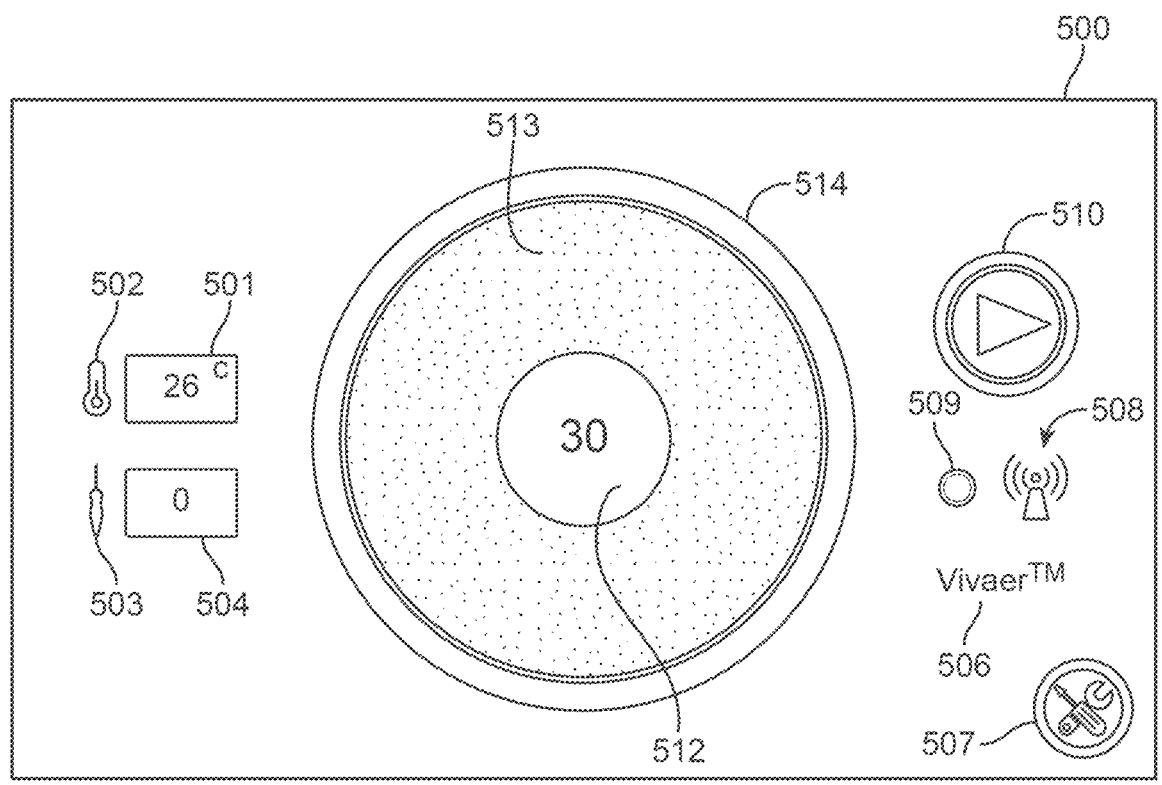
FIG. 16 is a screen shot of a default main screen display on an electrosurgical console, as it appears before the electrosurgery treatment has started, according to one embodiment.

Referring now to FIG. 16, once the physician or other user has attached the stylus 104 to the console 102, the standby image of FIG. 4 may be replaced by a default main screen image 500. This main screen image 500 is what the user sees before the procedure has started. Under normal operating conditions, the user can select either default treatment settings or manual treatment settings. The default treatment settings are pre-loaded into the processor of the console 102 and do not require any additional settings inputs from the user. In some embodiments, it may be possible for the user to select from several sets of default settings. Operation under the default settings mode is described in relation to FIGS. 16-18, and operation under the custom settings mode is described in relation to FIG. 19.

Figure 17:
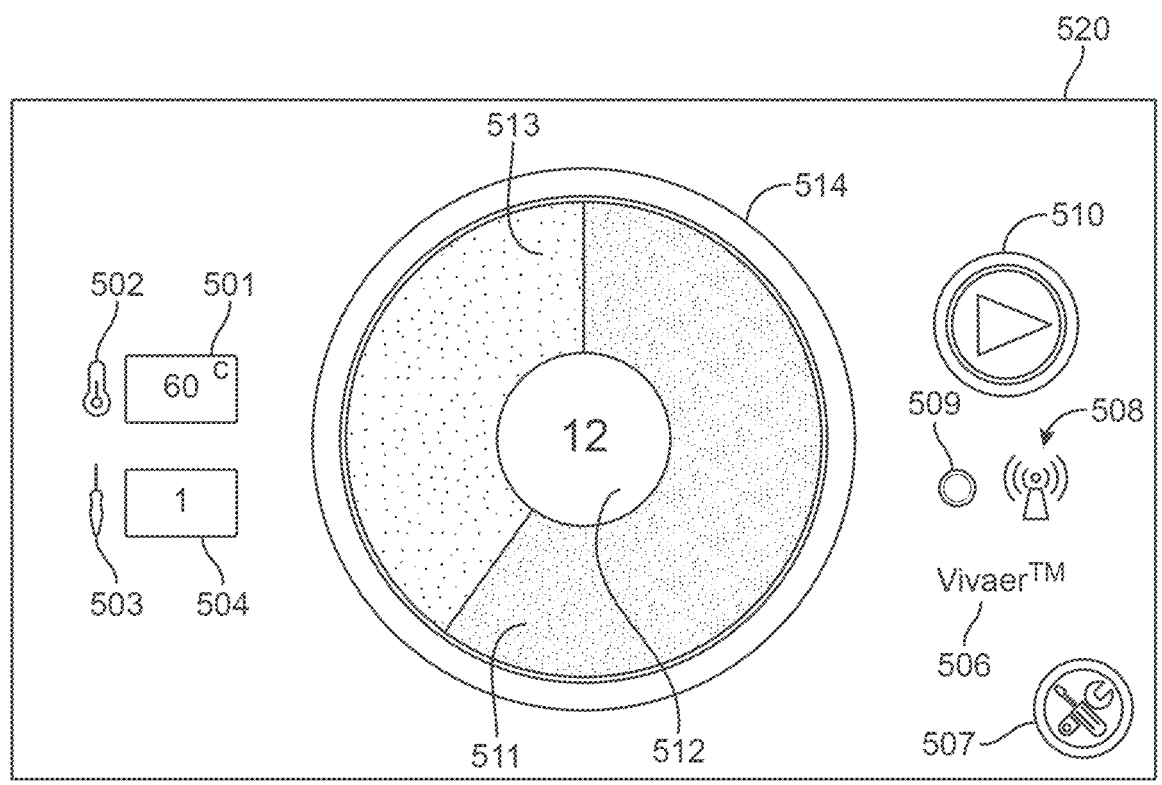
FIG. 17 is a screen shot of a default main screen display on an electrosurgical console, as it appears during an RF delivery stage of an electrosurgery treatment, according to one embodiment.

FIG. 17 shows the default image 500 displayed on the display screen 108 of the console 102, once a valid stylus 104 is connected. In this embodiment, the default image includes a stylus temperature indicator 501, a temperature icon 502, a stylus icon 503, treatment number indicator 504, a stylus type connected indicator 506, a start/stop button 510, an RF ON indicator light 509, an RF icon 508, a custom treatment button 507 and a central, circular, graphical treatment progress display 514.

The graphical treatment progress display 514 has several portions, according to the embodiment shown in FIG. 16. First, there is a total treatment timer 512, which is displayed as a central circle with a counting down number, representing seconds (or alternatively minutes, or minutes and seconds) remaining in the current procedure. Here, for example, the treatment has not started yet, and the total treatment timer 512 shows a time of 30 seconds, thus indicating that at least the next tissue treatment will last 30 seconds total. Immediately surrounding the central circle total treatment timer 512 is a treatment time indication ring 513, which acts as an indicator of elapsed and remaining time in the procedure. In the default image 500 of FIG. 16, the treatment has not started, so the entire outer ring 513 is one initial color. The initial color of the ring 513 indicates time remaining in the treatment, which in this case takes up the entire ring 513.

Other indicators on the screen shot image 500 also show that the treatment has not yet started. For example, the RF ON indicator light 509 is not illuminated yet, because the console 102 is not yet delivering RF energy to the stylus 104. The treatment number indicator 504 shows that zero treatments have been performed with the stylus 104 that is currently plugged into the console 102. And the temperature indicator 501 shows a stylus temperature of 26 degrees Celsius. To begin a treatment, the physician user will touch the start/stop button 510 on the touchscreen 108.

Referring now to FIG. 17, a later screen shot 520 of the default settings screen is illustrated. At this stage, RF energy is being delivered from the console 102 to the stylus 104, as indicated by the RF ON indicator light 509. The total treatment timer 512 of the graphical treatment progress display 514 shows that 12 seconds remain in the treatment. The outer ring 513 now includes a darker RF energy delivery time portion 511, and the lighter remaining portion of the ring 513 indicates the portion of the total treatment time that is still remaining. As the RF energy delivery stage of the treatment begins and progresses, the darker RF energy delivery time portion 511 takes up more and more of the outer ring 513, moving in a clockwise direction. In other words, the RF energy deliver indicator 511 starts at zero, at the twelve o'clock position on the ring 513, and moves around the ring in a clockwise direction.

Other indicators that the treatment is in progress include the temperature indicator 501 showing a temperature of 60 degrees Celsius and the treatment number indicator 504 showing that this is the first treatment being performed with the stylus 104 currently plugged into the console 102.

In some embodiments, the console 102 may be activated, and RF energy delivered to the stylus 104 in either of two ways—the start/stop button 510 may be touched, or a foot pedal coupled with the console 102 may be depressed. The RF ON indicator 509 lights up when the console 102 is delivering RF power. The stylus type connected indicator 506 indicates what type of stylus 104 is connected to the console 102, which in the example shown is a Vivaer™ stylus (Aerin Medical, Inc., www.aerinmedical.com). This indicator 506 may be useful in embodiments where the console 102 is configured for use with multiple different types of styluses. The stylus temperature indicator 501 shows the actual temperature of the distal, treatment end of the stylus 104. The treatment number indicator 504 displays the number of the treatment currently being completed with the stylus 104 that is attached to the console 102. Finally, the custom treatment button 507 allows the user to customize one or more treatment parameters. Touching this button 507 will lead the user to a new display screen with different options. In alternative embodiments, the various icons and/or indicators on the default display 520 may be changed or moved. In some embodiments, one or more of the icons and/or indicators may be eliminated.

Figure 18:
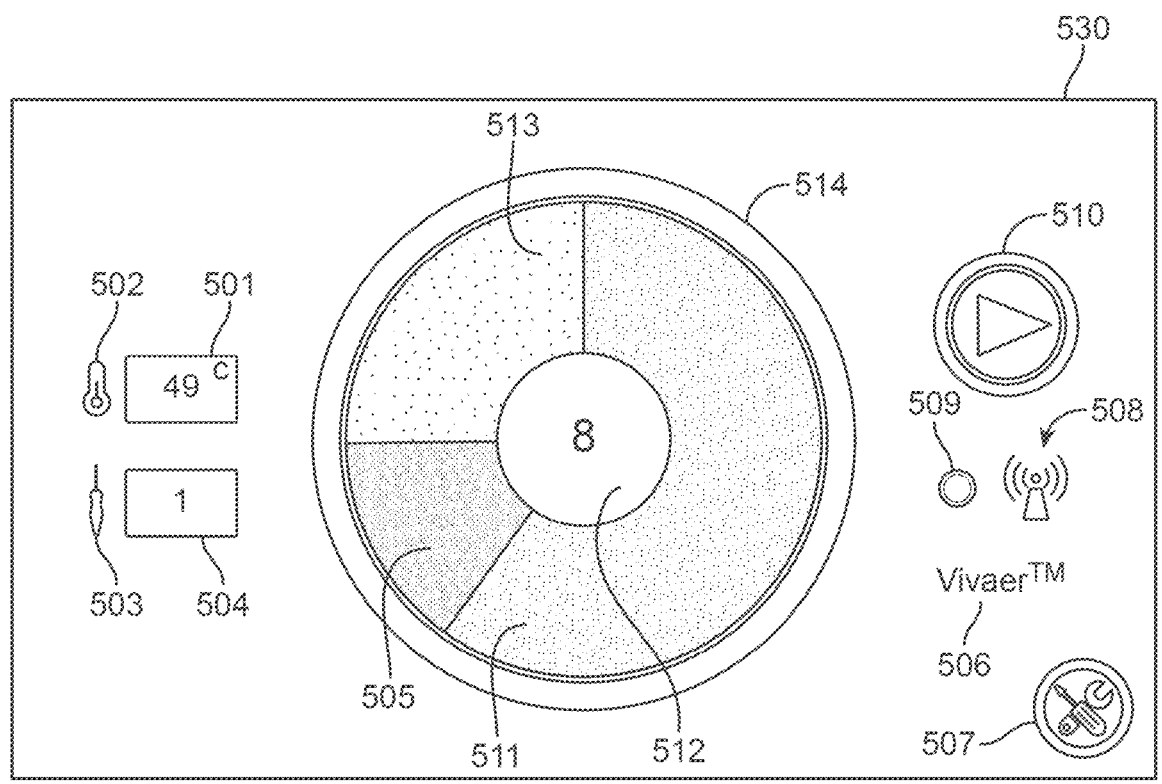
FIG. 18 is a screen shot of a default main screen display on an electrosurgical console, as it appears during a cooling stage of an electrosurgery treatment, according to one embodiment.

Referring now to FIG. 18, a third screen shot 530 of the default setting screen is illustrated. At a given amount of time into the procedure, the console 102 stops delivering RF energy to the stylus 104, and a cool down phase begins. The cool down phase is shown on the ring 513 as a differently colored or shaded segment 505, as compared to the RF ON segment 511, and it may be called a cool down timer indicator 505. The cool down timer indicator 505 moves around the ring in a clockwise direction until the procedure is complete. Any amount of time remaining in the procedure is indicated by the total treatment time remaining portion of the ring 513.

In the screen shot of the main screen image 530 shown in FIG. 18, the current stage of treatment is illustrated as follows: The central circle total treatment timer 512 shows there are eight seconds remaining in the treatment. The RF ON indicator segment 511 and the cool down timer segment 505 show that the RF delivery portion of the treatment is complete, because the cool down timer segment 505 has started. Since the total treatment time remaining portion of the ring 513 is still visible, this shows the user that the cool down phase is still in process. In a real life scenario, the cool down timer portion 505 would also be moving clockwise, thus easily telling the user what phase the treatment was in. In this case, the total treatment time portion of the ring 513 shows that approximately one fourth of the entire treatment time still remains. The temperature of 49 degrees Celsius in the temperature window also tells the user that the console 102 is in the cooling phase, since the temperature of the stylus 104 has decreased from 60 degrees. Finally, the RF ON indicator light 509 is not illuminated.

In various embodiments, any colors, shades, shapes, graphics and/or the like may be used for the various segments 511, 505 of the outer ring 513. In one embodiment, for example, the RF ON timer indicator 511 is navy blue, the cool down timer indicator 505 is gray, and the total treatment time remaining portion 513 is light blue. Any other colors may be used, however, in alternative embodiments. In another alternative embodiment, the entire ring 513 may be one color, and a line that acts as a timer may move clockwise around the ring 513, similar to a long hand on a clock. In a variation on such an embodiment, the color of the ring 513 behind the moving line may change. Thus, the ring 513 and the segments 511, 505 may have any suitable size, color scheme or configuration.

Additionally, the default (or custom) settings of the console 102 may have any suitable ranges and combinations for the various parameters of the console 102. For example, one timing default setting may have a total treatment time of 30 seconds, an RF ON time of 18 seconds, and a cooling time of 12 seconds. This is but one example, however, and any number of other time settings may alternatively be used. A default temperature may also be set for RF delivery, for example 60 degrees Celsius as the maximum temperature. Again, any suitable default settings may be set in various embodiments.

Figure 19:
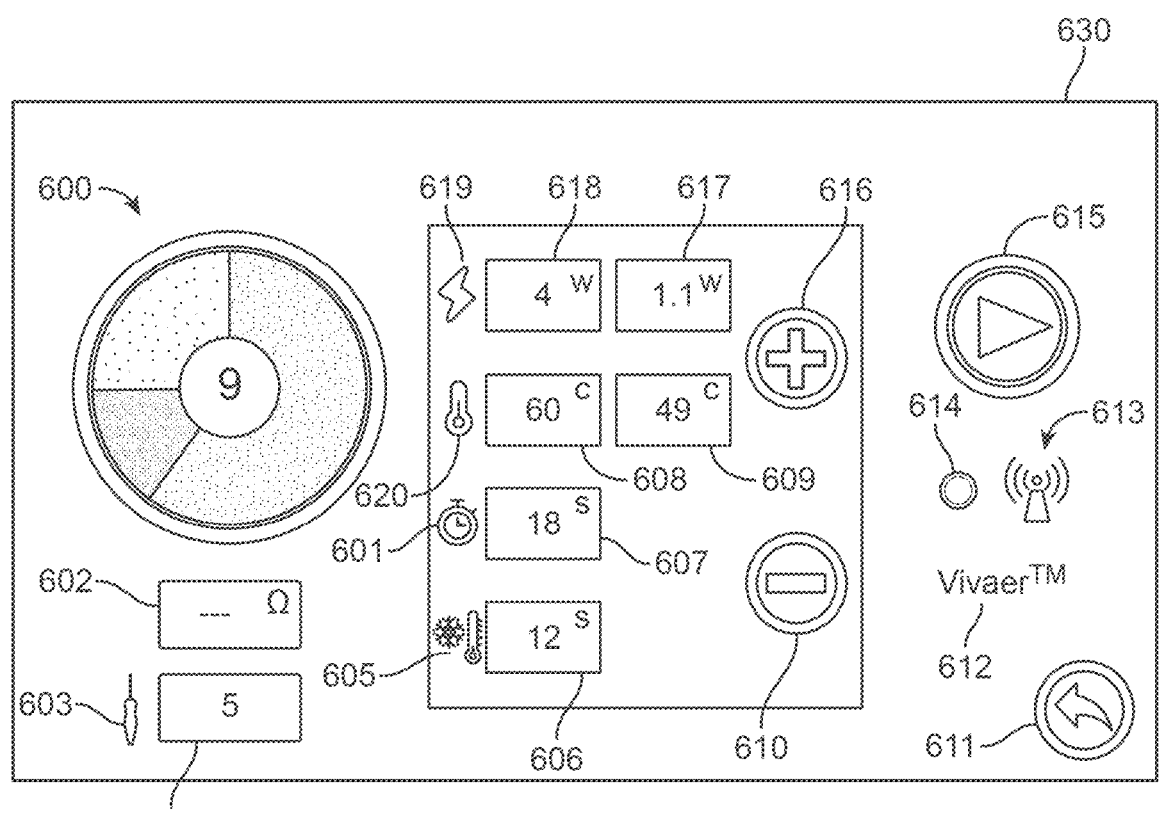
FIG. 19 is a screen shot of a custom treatment settings screen display on an electrosurgical console, as it appears during a cooling stage of an electrosurgery treatment, according to one embodiment.

Referring now to FIG. 19, as just described, the physician or other user can choose to access a custom treatment screen 630 by touching the custom treatment button 507 on the initial default screen 500 (FIG. 16). In the embodiment shown, the custom treatment screen 630 includes a graphical treatment progress display 600, which is smaller but otherwise the same as the graphical treatment progress display 514 of the default screen 500. The custom treatment screen 630 also includes a timer icon 601, an impedance display 602, a stylus icon 603, a number of treatments indicator 604, a cooling icon 605, a set cooling time window 606, a set RF ON time window 607, a set temperature window 608, an actual temperature indicator 609, a down button 610, a back button 611, a stylus type indicator 612, an RF icon 613, an RF ON indicator 614, a start/stop button 615, an up button 616, an actual power delivery indicator 617, a set power window 618, an RF power icon 619 and a temperature icon 620. As with the previously described default screen 500, the icons and/or indicators of the custom treatment screen 630 may be moved, changed and/or eliminated, according to various alternative embodiments.

Through the custom treatment screen 630, the user can adjust the power (power window 618), temperature (temperature window 608), treatment time (RF on time window 607) and/or cool down time (cooling time window 606), by touching any one of the set windows and then touching the up button 616 and/or the down button 610 to adjust a given value. To set power, for example, the user may touch the power window 618 and then adjust the temperature by pressing the up button 616 or the down button 610. The console 102 may be configured to only allow adjustments within ranges. For example, the power on the console 102 may be selected at 3 W, 4 W or 5 W in one embodiment. Maximum stylus temperature may be selected in a range of 50 degrees Celsius to 70 degrees Celsius in one embodiment. RF energy delivery time (RF ON time) may be selected for between 6 seconds and 18 seconds, in 2-second increments, and cooling time may be selected for between 0 seconds and 12, in 3-second increments, in one embodiment. Any other suitable ranges and combinations of ranges may be used, in alternative embodiments, and those provided here are merely examples.

For the information of the user, the impedance display 602 and stylus usage count 604 are also displayed. The back button 611 can be touched to return to the default screen 500 (FIG. 16). During treatment, the actual RF power 617 and temperature reading 609 are also shown. In alternative embodiments of the custom treatment display screen 630, one or more icons, indicators, buttons and/or windows may be moved, changed or eliminated.

Figure 20:
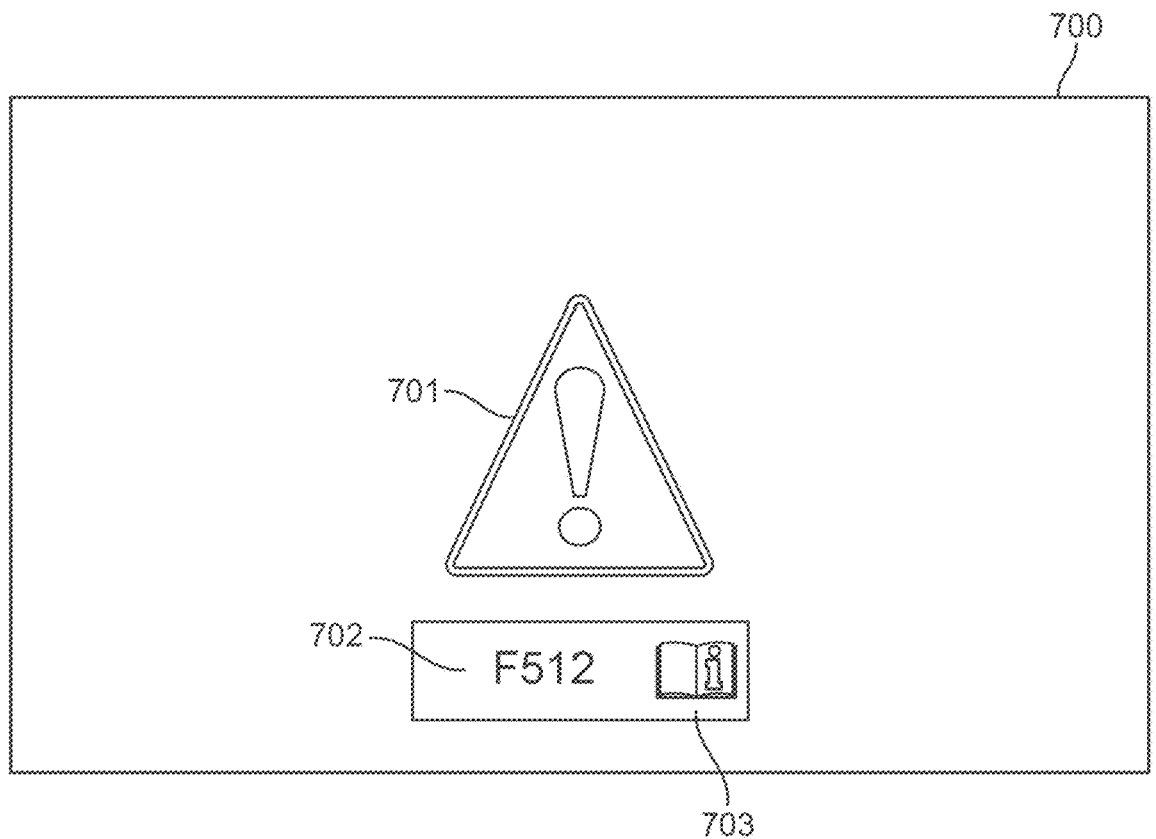
FIG. 20 is a screen shot of a fault screen display on an electrosurgical console, according to one embodiment.

Referring now to FIG. 20, in some embodiments, the console 102 may be programmed to display a fault screen 700 when a fatal error of the system 100 occurs. The fault screen 700 may include, for example, a fault error symbol 701 that indicates a serious error has occurred, rendering the console 102 unusable. The fault screen may also include an error code 702, indicating what kind of error has occurred, and a refer to IFU (instructions for use) symbol 703. The fault error symbol 701 may be any color or combination of colors, such as a red triangle with a black exclamation point. In some embodiments, after the fault screen 700 appears, the console 102 may only be used after the user turns the console 102 off and turns it back on again.

Figure 21:
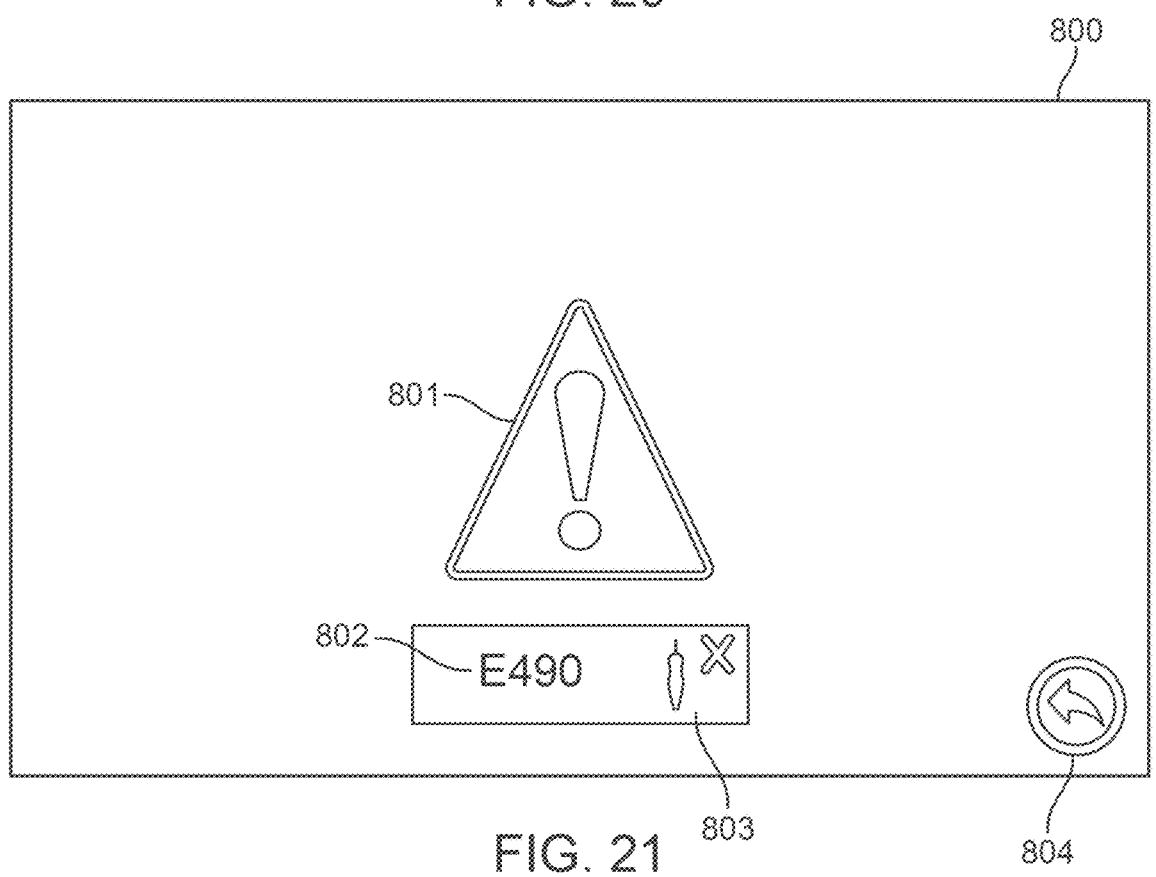
FIG. 21 is a screen shot of an error screen display on an electrosurgical console, according to one embodiment.

Referring now to FIG. 21, in some embodiments, the console 102 may be programmed to display an error screen 800 when a non-fatal error of the system 100 occurs. The error screen 800 may include, for example, a caution symbol 801 that indicates an error has occurred. The error screen may also include an error code 802, indicating what kind of error has occurred, an error symbol 803, and a back button 804. The caution symbol 801 may be any color or combination of colors, such as a yellow triangle with a black exclamation point. In this embodiment, the user may touch the back button 804 to return to the previous screen being used when the error occurred, and the user may fix the error at that screen.

Figure 22:
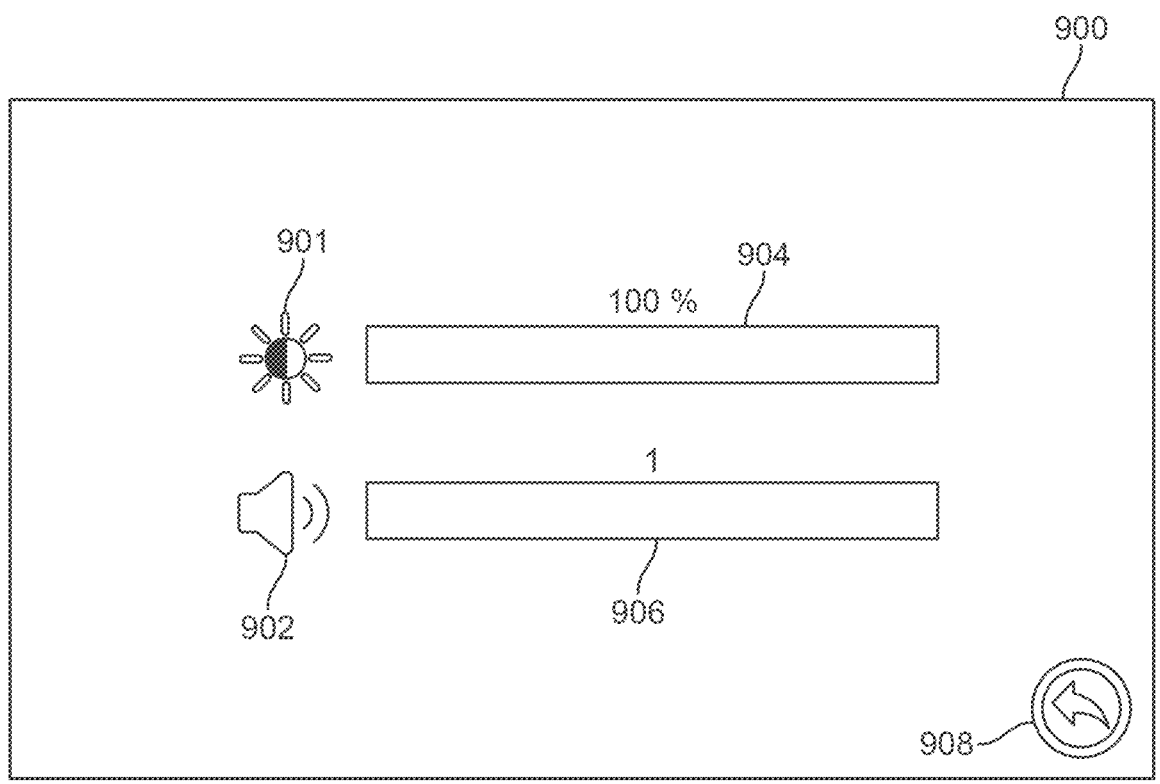
FIG. 22 is a screen shot of a settings screen display on an electrosurgical console, according to one embodiment.
Figure 23:
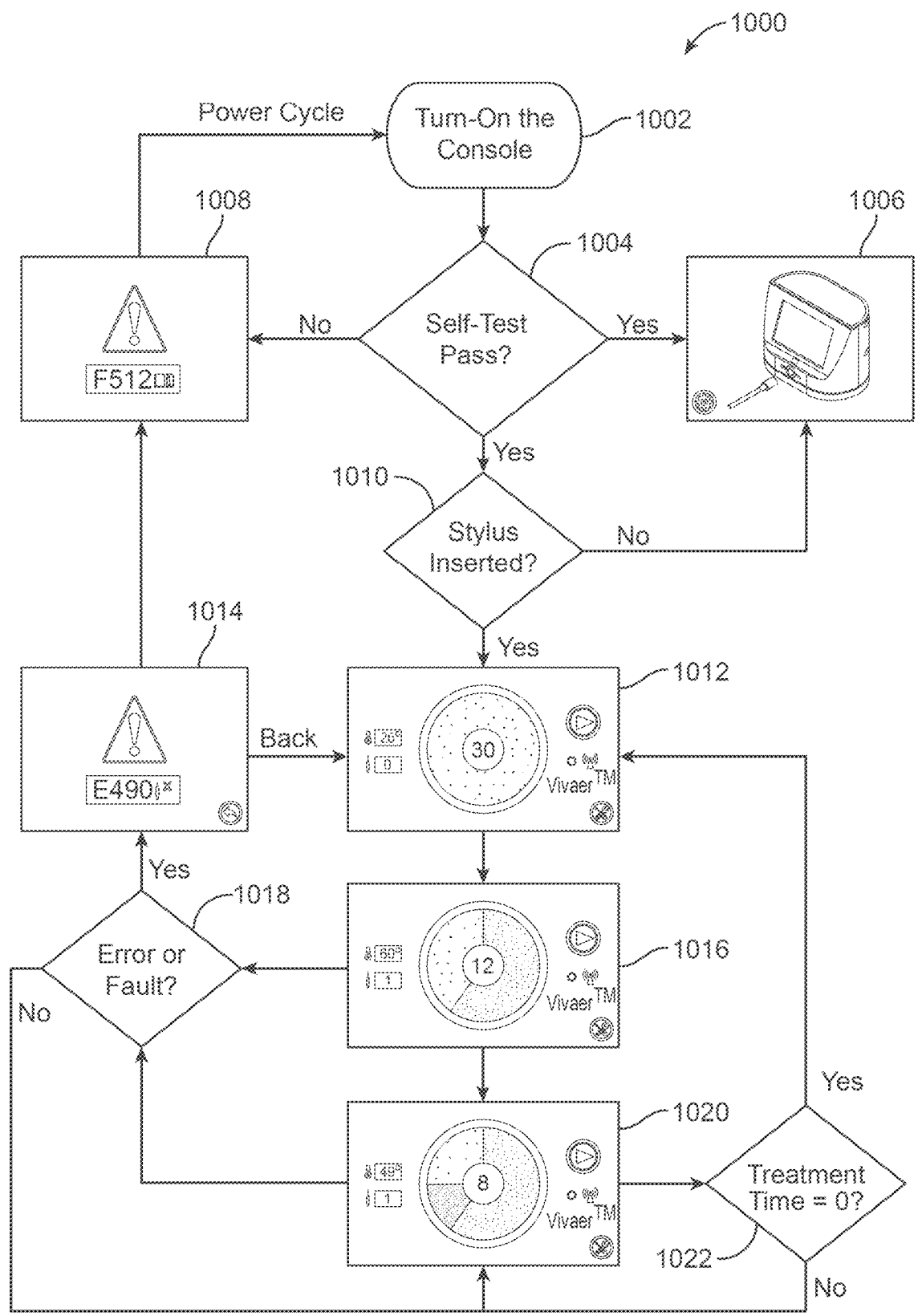
FIG. 23 is a flow diagram of a method of performing an electrosurgical treatment, using a console as described in the present application, according to one embodiment.

FIG. 22 is a screen shot of a settings screen 900, which may be provided on the display 108 of the console 102. In this embodiment, the settings screen 900 includes an adjust brightness icon 901, an adjust volume icon 902, a sliding bar brightness control 904 and a sliding bar volume control 906. The brightness control 904 and the volume control 906 may have any color or combination of colors. In some embodiments, a numerical indication of brightness and volume may also be included. The settings screen 900 also includes a back button 904 to allow the user to return to a previous screen.

Referring now to FIG. 22, a method 1000 of using the console 102 of the electrosurgery system 100 is illustrated. First, the user turns on 1002 the console 102. The console 102 performs a self-test 1004. If the self-test passes, the console 102 displays the standby screen 1006. If the console 102 fails the self-test, the fault screen is displayed 1008. In some embodiments, the fault screen can only be cleared by power cycling the console 102 to repeat the self-test routine. Next, assuming the self-test is passed, the user plugs the stylus 104 into the console 102. If the correct stylus is inserted 1010, the console 102 shows the default main screen 1012. The user presses the start/stop button or a foot switch, and the RF energy delivery portion of the treatment starts 1016, followed by the cooling portion 1020. When the treatment is completed 1014, the screen returns to the default main screen 1012. If an error occurs during treatment 1018, the error screen is shown 1014. The user can press the back button on the error screen to return to the default main screen 1012. If the error is fatal, the screen changes to the fault screen 1008. At various points the in method 1000, the user may also select the custom treatment screen (FIG. 19) by pressing the custom treatment button 507 on the default screen.

Figure 29C:
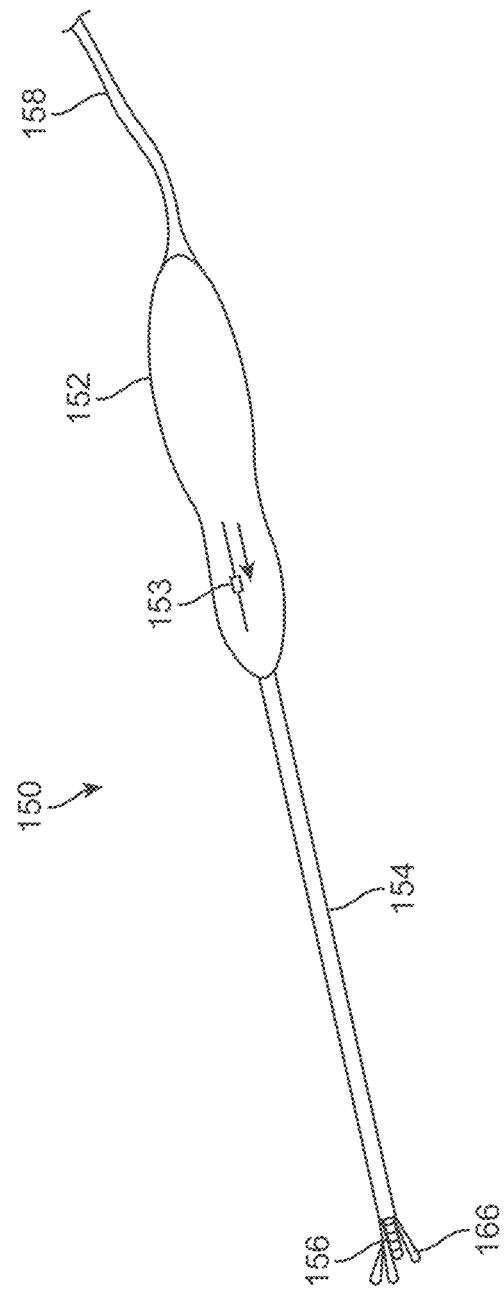
FIGS. 29C and 29D are perspective views of the stylus of FIGS. 29A and 29B, illustrating operation of the expandable wire electrode component.

Referring now to FIGS. 29A-29D, another embodiment of a nasal airway tissue treatment stylus 150 is illustrated. As shown in FIG. 29A, the stylus 150 includes a handle 152 with a slider 153, a shaft 154, a distal tip 156 and a power cord 158. FIG. 29B is a front view of the stylus 150, showing additional features. In this embodiment, the stylus 150 includes a space 164 between the inner wall of the shaft 154 and the outer perimeter of the distal tip 156. (FIG. 29B also shows the two rows of electrodes 160 and the thermocouple 162 of the distal tip 156.) Within the space 164 and around the distal tip 156 resides an expandable wire electrode component 166, which is moveable out of the distal end of the shaft 154 to allow it to expand and be used for delivering a treatment.

In use, the stylus 150 may be used first in the configuration shown in FIG. 29A. The electrodes 160 of distal tip 156 may be used to treat tissue, such as posterior nasal nerve tissue, turbinates, nasal swell bodies and/or the like. In one embodiment, for example, the distal tip 156 may be used to treat one or more nasal turbinates in areas that are anterior to the nasal nerve that will be treated subsequently.

Figure 29D:
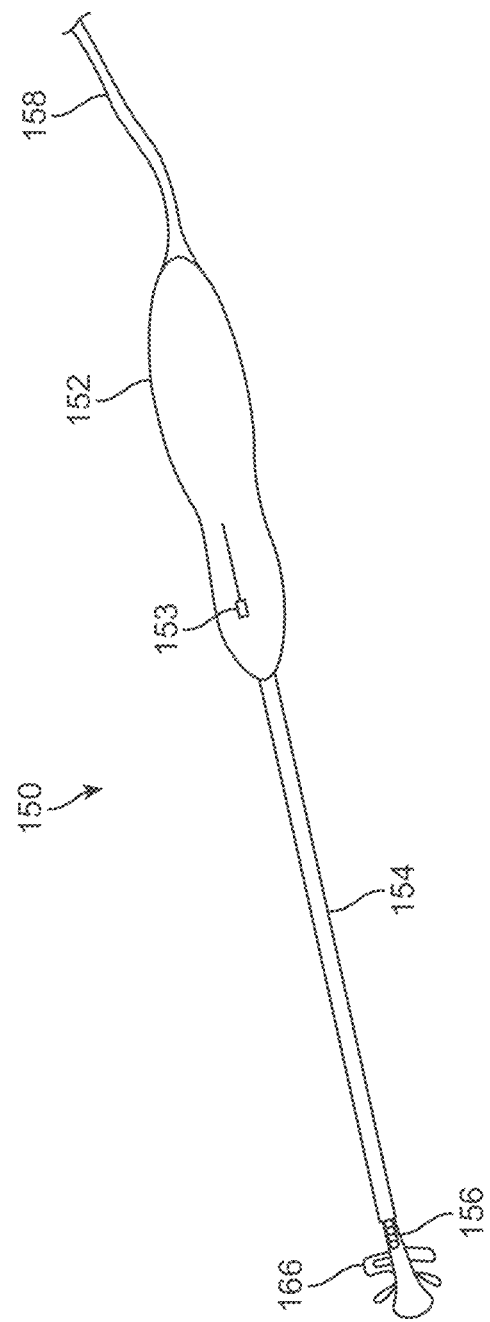

After treating with the stylus 150 in the FIG. 29A configuration, and referring now to FIG. 29B, the slider 153 on the handle 152 may be advanced to advance the expandable wire electrode component 166 out of the distal end of the shaft 154. FIG. 29D shows the slider 153 further advanced and the expandable wire electrode component 166 fully advanced and expanded. The expandable wire electrode component 166 may include multiple bipolar electrode pairs located at various locations along its length. Optionally, the expandable wire electrode component 166 may also include one or more thermocouples and/or multiple nerve sensors (such as electrodes), which may be used to measure a temperature of nasal mucosa and sense where nerve tissue is located under the mucosa, respectively. In some cases, all electrode pairs may be activated at the same time. Alternatively, only one or more selected electrode pairs may be activated. In some cases, the expandable wire electrode component 166 may be used to determine the location of nerves and then only bipolar electrode pairs located directly over those nerves may be activated.

In one example, after the stylus 150 has been used in the initial configuration shown in FIG. 29A to treat one or more turbinates, swell bodies or the like, the stylus 150 may be changed to the expanded configuration shown in FIG. 29D. In that configuration, the expandable wire electrode component 166 may be used to treat posterior nasal nerves and/or any other nerve tissue the physician wants to treat. In other words, the stylus 150 is used to treat nerve tissue in the FIG. 29D configuration and used to treat any other tissues in the FIG. 29A configuration. This is only one example, however, and a physician may use the stylus 150 in any suitable manner. After treatment with the expandable wire electrode component 166 is complete, the expandable wire electrode component 166 may be pulled back into the shaft by sliding the slider 153 proximally. It may also be possible to treat further in the FIG. 29A configuration after treatment with, and retraction of, the expandable wire electrode component 166.

Figure 30:
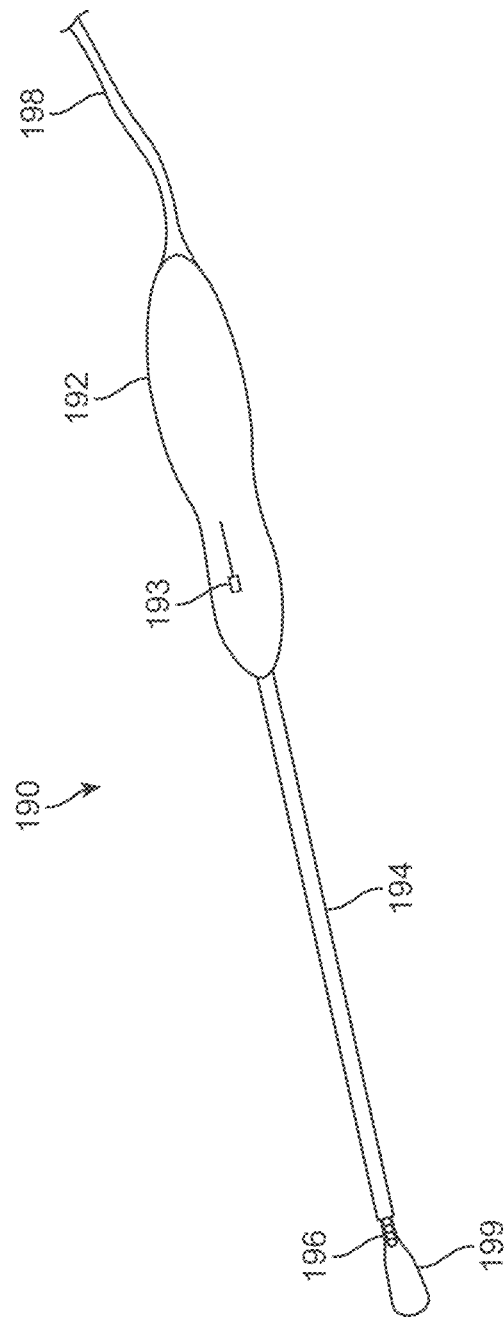
FIG. 30 is perspective view of another alternative embodiment of a nasal airway tissue treatment stylus that includes an expandable cryotherapy balloon.

Referring now to FIG. 30, an alternative embodiment of a nasal airway treatment stylus 190 is similar to the one just described, except that rather than the expandable wire electrode component 166, this embodiment of the stylus 190 includes an expandable cryotherapy balloon 199. The stylus 190 also includes a handle 192 with a slider 193, a shaft 194, a distal tip 196 and a power cord 198. In this embodiment, the cryotherapy balloon 199 can be advanced out of the distal end of the shaft 194 using the slider 193. A source of cryogenic substance, such as nitrous oxide in a small canister, may be attached to the handle 192 and transmitted through a lumen in the shaft 194 to inflate the cryotherapy balloon 199. The inflated cryotherapy balloon 199 will absorb energy from the nasal airway tissues and thus can be used to ablate posterior nasal nerves and/or any other target nerve tissue or other target tissues. When a treatment is complete, the cryogenic substance may be evacuated from the cryotherapy balloon 199, causing it to deflate, and the stylus 190 may be removed from the nose. Optionally, the deflated cryotherapy balloon 199 may be pulled back into the shaft 194 before removal of the stylus 190, but that may not be necessary. As with the previous embodiment, any suitable nasal airway tissue may be treated with the distal tip 196 of the stylus 190 before inflating the cryotherapy balloon 199 for additional tissue treatment.

Figure 31:
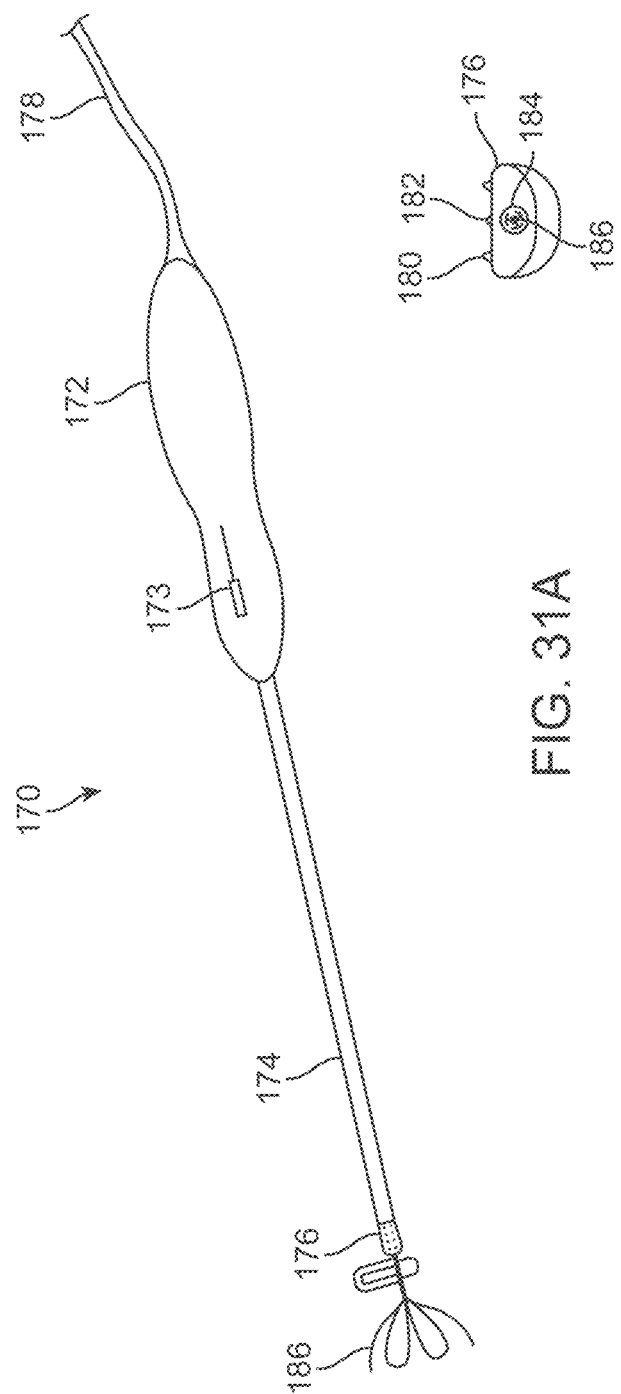
FIGS. 31A and 31B are perspective and front views, respectively, of another alternative embodiment of a nasal airway tissue treatment stylus that includes an expandable wire electrode component that advances out of the distal tip of the device.

With reference now to FIGS. 31A and 31B, another alternative embodiment of a nasal airway tissue treatment device 170 is illustrated in perspective view (FIG. 31A) and front view (FIG. 31B). In this embodiment, the stylus 170 includes a handle 172 with a slider 173, a shaft 174, a distal tip 176, an expandable wire electrode component 186, and a power cord 178. As best seen in FIG. 31B, the distal tip 176 includes two rows of bipolar RF electrode pairs 180, a thermocouple 182 and an opening 184 which leads directly into a lumen in the shaft 174. The expandable wire electrode component 186 is located inside the opening 184 and the lumen (not visible on these drawings) and may be advanced out of the opening 184 with slider 173 to allow the expandable wire electrode component 186 to expand and be used for treatment. All of the same features and methods of use described above may be applied to this embodiment of the stylus 170, the primary difference being that the expandable wire electrode component 186 is located within the distal tip 176 and advances out of the opening 184. The expandable wire electrode component 186 may have any suitable size, shape and configuration of wires, according to various embodiments.

In some examples, treatment devices and systems are able to change among multiple different configurations. Such adjustable, configurable treatment devices and systems can facilitate treatment of different tissue types or different locations within a nasal airway. For example, the device may be able to transition from a first configuration suited for treating a nasal septum to a second configuration suited for treating nasal turbinates to a third configuration suited for treating lateral cartilage.

Different configurations may be suited to providing different kinds of treatment. For example, there may be configurations suited for providing treatment to previously treated and/or untreated tissue, and for shrinking and/or shaping tissue. For example, a first configuration of the device may be suited for providing treatment to untreated tissue, while a second configuration of the device may be suited for treating the already-treated tissue (e.g., shaping the shrunk tissue). For instance, a clinician may be able to shrink tissue while using the device in the first configuration, transition the device to the second configuration, and shape the shrunk tissue using the same (single) device. In another example, a first configuration of the device may be suited for treating a first kind of tissue (e.g., a first tissue type, such as cartilage or mucosa, or a first tissue location, such as turbinates or a septal tissue), and a second configuration of the device may be suited for treating a second kind of tissue. In another example, a first configuration is for providing a first part of a treatment and a second configuration is for providing a second part of the treatment.

Additionally, different configurations may provide treatment using different modalities. For example, a first configuration may provide treatment using radiofrequency energy, while a second configuration of the device may provide cryotherapy treatment. Similarly, different configurations may have different mechanical or energy delivery profiles. A first configuration may have a convex treatment surface profile, and a second configuration may have a concave treatment surface profile. A first configuration may have a high-energy treatment profile, and a second configuration may have a low-energy treatment profile. Additionally, the device may be able to sense the current configuration of the device and modify treatment parameters to suit the current configuration.

Various kinds of configurations are contemplated. In an example, a length of the treatment device can be modified. Modifying the length of a treatment device can facilitate treatment of different kinds of tissue and tissue in different locations within a patient's airway. For instance, in a first configuration, the treatment device may be relatively short and more suited for treating nasal tissue located nearer to the patient's nostrils. In a second configuration, the treatment device may be relatively longer and more suited for treating nasal tissue located deeper in the patient's nasal airway. During a procedure, a clinician may use the device in the first configuration to treat tissue in a first region of the patient's airway and then modify the device to assume the second configuration to treat tissue in a second region, deeper in the patient's nasal airway than the first.

In another example, a treatment element of the treatment device may be rotatable relative to a handle of the device. Rotation of the treatment element can allow the clinician to modify a treatment direction. For example, a clinician may prefer a particular treatment direction for treating particular anatomy or for a given way that the clinician holds the device. In some examples, the treatment element may have a variety of treatment portions, and rotating the treatment element may allow the clinician to select a specific treatment portion to use. For example, there may be a convex surface for shaping tissue on a first side of the treatment element and a concave surface for shaping tissue on a second side of the treatment element. The clinician may rotate the treatment element such that the proper side is exposed to a treatment site to allow for treatment. This adjustability provides for flexible treatment of different tissues/locations/etc. with a single treatment device.

In yet another example, a treatment element of a treatment device may be configured to be tilted in a plane substantially parallel to the length of the treatment device. This can facilitate treatment of different kinds of tissue. For example, a clinician may tilt the treatment element to facilitate treatment of a posterior aspect of a nasal turbinate. Tilting the treatment element can also facilitate transitioning the treatment device from a navigation configuration (e.g., a configuration that allows for easier navigation) to a treatment configuration (e.g., a configuration more suited for treatment of target tissue).

In a further example, a treatment element of the treatment device may be able to be rotated in a plane substantially perpendicular to a treatment direction (e.g., typically the treatment direction is perpendicular to a face of the treatment element).

In another example, there is a base treatment device having one or more attachment features suited for connecting a supporting feature to the base device to expand capabilities or functionality of the base device. For example, the supporting features may be clamps, sensors, treatment modalities and/or other components.

In some embodiments, a treatment element may be configured to treat tissue by applying treatment (e.g., energy, cryotherapy, or other treatments) from a position external to the patient's airway. For example, in some embodiments, the devices may be configured to apply energy from an element positioned outside a patient's body, such as on the skin.

In some embodiments, the device is configured to position the tissue to be modified. In some embodiments, the device includes features or mechanisms to pull, push or position airway tissue into a mold for re-shaping. For example, suction, counter traction, or compression between two parts of the device may be used.

In some embodiments, the treatment device includes one or more molds configured to reshape tissue. The mold or re-shaping element may be fixed in size or may vary in size. The mold may also be fixed in shape or may vary in shape. For example, the size or shape of the element may be varied or adjusted to better conform to the airway of a patient. Adjustability may be accomplished using a variety of means, including, for example, mechanically moving the mold by way of joints, arms, guidewires, balloons, screws, stents, or scissoring arms. The mold may be adjusted manually or automatically.

In some embodiments, the mold or re-shaping element includes a separate or integrated energy-delivery or treatment element (e.g., an electrode). The treatment element may be fixed or adjustable in size. For example, the treatment element may be adjusted to better conform to a portion of the airway of a patient. In the case of a separate re-shaping element and treatment element, a distance between the two elements may either be fixed or adjustable. Adjustability may be accomplished using a variety of means, including, for example, mechanically moving the mold by way of joints, arms, guidewires, balloons, screws, stents, or scissoring arms, among other means.

In some embodiments, the mold or another part of the device is configured to deliver cooling (discussed in more detail below). In some embodiments, the mold or re-shaping element includes a balloon configured to reshape and/or deform tissue. A balloon may also be configured to deliver energy-based treatment using liquid or gas that is heated or cooled.

Various electrode arrangements may be used for applying energy to the tissue. These electrodes may, for example, deliver RF energy to preferentially shape the tissue to ameliorate symptoms, such as excessive airway resistance. In some embodiments, one or more electrodes may be used alone or in combination with a tissue shaping device or mold. In other embodiments, one or more electrodes may be integrally formed with a tissue shaping device or mold so that the electrodes themselves create the shape for the tissue. In some embodiments, the energy-delivery devices may use alternating current. In some embodiments, the energy-delivery devices may use direct current. In certain such embodiments, the energy-delivery device may include a configuration that uses a grounding pad.

In some embodiments, the term "electrode" refers to any conductive or semi-conductive element that may be used to treat the tissue. This includes, but is not limited to, metallic plates, needles, and various intermediate shapes such as dimpled plates, rods, domed plates, and other configurations. Electrodes may also be configured to provide tissue deformation in addition to energy-delivery. Unless specified otherwise, electrodes described can be monopolar (e.g., used in conjunction with a grounding pad) or bipolar (e.g., alternate polarities within the electrode body or used in conjunction with other tissue-applied electrodes).

Figure 32:
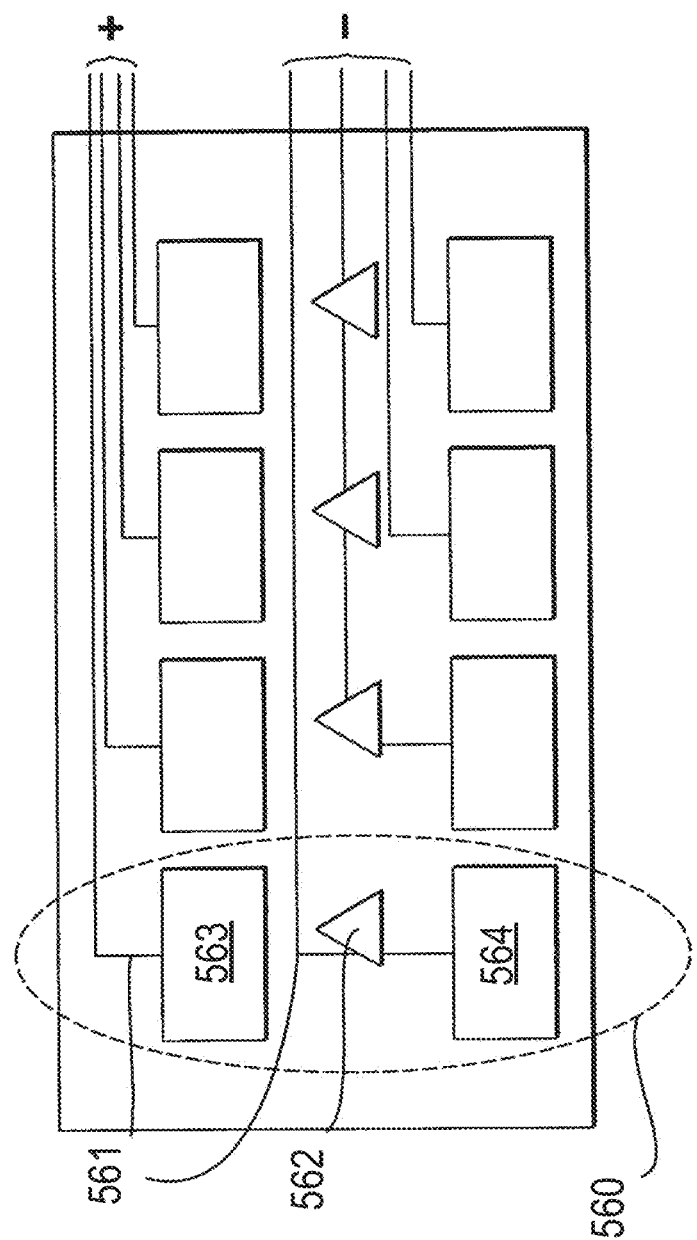
FIG. 32 is a block diagram depicting an array of electrodes of a treatment device arranged in a multi-channel configuration, according to one embodiment.

FIG. 32 is a block diagram depicting an array of electrodes of a treatment device arranged in a multi-channel configuration. Different treatment sites may have treatment surface areas of varying size and shape. Additionally, clinicians operating a treatment device may vary in skill, dexterity, and habits. Due to these variabilities, each electrode pair of the device may have varying degrees of contact with tissue of the treatment site. For a configuration in which all pairs of electrodes are controlled by one main electrical channel, this may lead to varying magnitudes of treatment energy passing through each electrode pair. The pair(s) of electrodes that have a higher degree of contact with the tissue may experience higher magnitudes of impedance in their individual circuit(s). Since treatment energy takes the path of least resistance, this may lead to treatment energy being diverted to pairs of electrodes that experience a relatively lower magnitude of impedance due to a relatively lower degree of tissue contact. Thus, it may be advantageous to control the treatment energy through each electrode to ensure repeatable treatments.

In some embodiments, each pair of electrodes may have a separate, controlled electrical channel to allow for different regions of the treatment element to be activated separately. In some embodiments, the separate activation of the pairs of electrodes may be based, in part, on the configuration of the treatment element or the device as a whole. In some embodiments, each electrode pair may be paired with its own thermocouple. By controlling the treatment energy flowing through each pair of electrodes using parameters including, but not limited to, temperature, a greater degree of control and accuracy over the treatment energy may be obtained, such that treatments may be repeatable.

As shown in FIG. 32, the treatment device may include one or more thermocouples 562 and an RF output channel 561 assigned to each electrode pair for feedback. An electrode pair may include a positive electrode 563 and a negative electrode 564. In some embodiments, the positive electrode 563 and the negative electrode 564 may be positioned opposite one another. Each electrode pair may have its own individual subsystem 560. The individual subsystem 560 may include a controlled RF output channel 561 and a thermocouple 562 to allow for independent adjustments. The thermocouple 562 may act as a feedback control to ensure that proper temperature is maintained at the treatment site.

Figure 33:
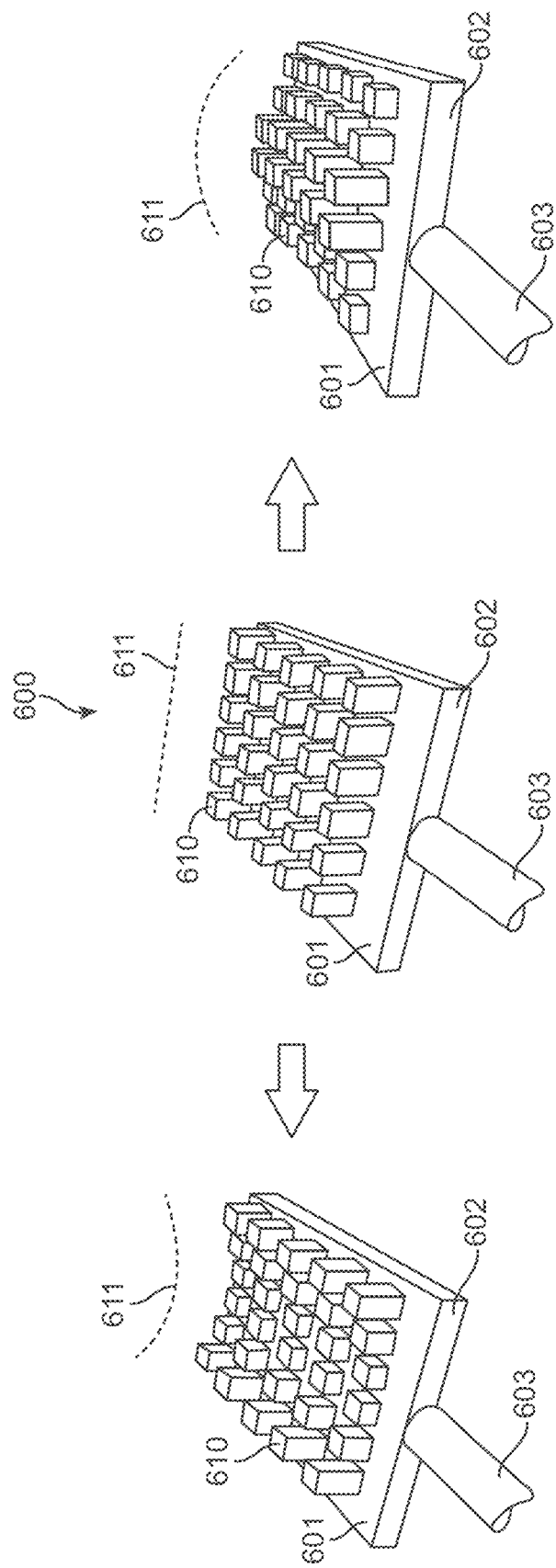
FIGS. 33A-33C are perspective views of an airway treatment device having an adjustable-height electrode array, according to one embodiment.

FIGS. 33A-33C illustrate an embodiment of a treatment device 600 including an array of electrodes 610 positioned on a surface of a treatment element 601. In some embodiments, as shown, the electrodes 610 may be arranged in a grid pattern. The electrodes 610 may be arranged in any pattern. One or more of the electrodes 610 may be extended or retracted to a preset height. It may be advantageous to manipulate the heights of the electrodes 610 to achieve a combination that forms a required treatment surface profile 611. The treatment surface profile 611 may include any combination of electrode numbers and heights. For example, FIG. 33A shows the electrodes 610 arranged in a concave configuration, FIG. 33B shows the electrodes 610 arranged in a flat configuration, and FIG. 33C shows the electrodes 610 arranged in a convex configuration. These are merely examples, however, and in alternative embodiments, the treatment element 601 may include any suitable number, shape, size and arrangement of electrodes 610, and the electrodes 610 may be arranged and adjusted into any suitable shape.

Figure 34:
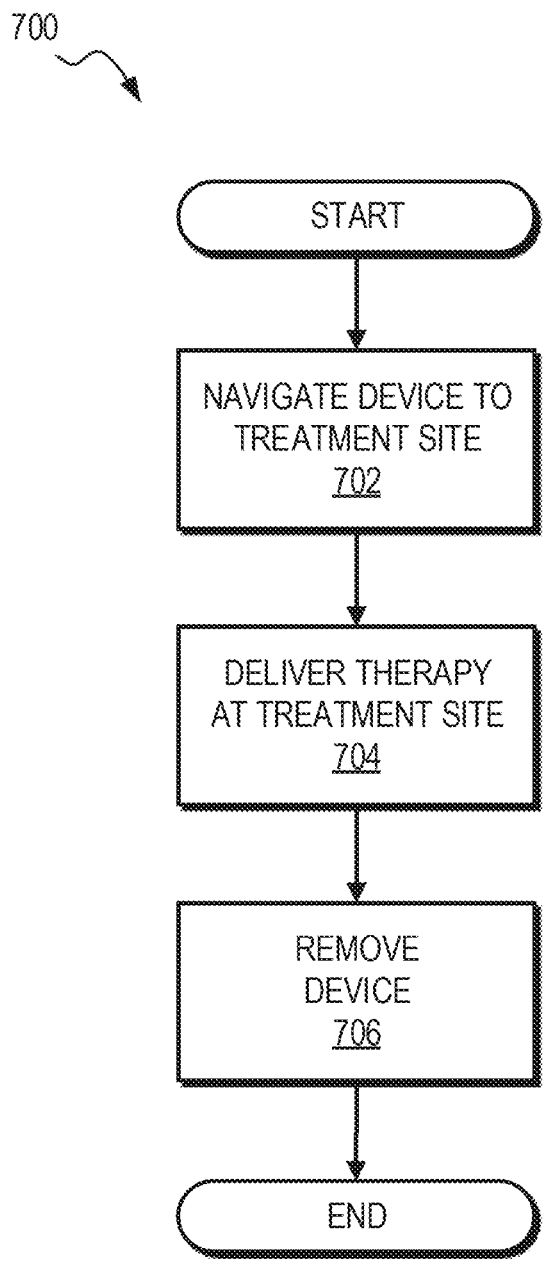
FIG. 34 is a block diagram, illustrating an example method for treating airway tissue, according to one embodiment.

FIG. 34 illustrates a method 700 for treating airway tissue (including but not limited to upper airway or nasal tissue), according to one embodiment. In this embodiment, the method first involves the step 702 of navigating a treatment device to a treatment site. This may be accomplished, for example, by advancing a treatment element into the patient's nose through one of the nostrils. Alternatively, other methods for accessing the treatment site may be used. The next step 704 involves delivering therapy at the treatment site 704. The final step 706 may involve removing the device from the patient. Alternatively, the method 700 may involve repositioning the device and delivering therapy again. The repositioning and delivering steps may be performed as many times as desired to treat a given patient.

Typically, the method 700 may begin with an additional step of selecting a patient. For example, a clinician can select a patient having symptoms of an airway condition. In another example, the clinician can select a patient having or thought to be having an airway condition, such as excessive airway resistance, post-nasal drip, or a deviated septum.

The method 700 can further include preparing the device. Preparing the device may include removing the device from sterile packaging, assembling one or more components of the device, sterilizing the device, attaching the device to an energy source, and/or other preparatory work. In certain implementations, this step may include customizing the device to suit the particular needs of the patient and the clinician. This may include articulating, manipulating, or otherwise changing one or more components of the device. For example, a clinician may articulate or bend a shaft and/or the treatment portion to place the device in a first, desired configuration. The first, desired configuration may be selected to facilitate navigation of the anatomy of the particular patient to reach the desired treatment site.

In certain circumstances, preparing the device may follow a previous use or a previous attempted use of the treatment device to treat the same or a different treatment site. For example, the clinician may determine that the device is not suitable in its current state, remove the device, and then reconfigure the device in a more suitable format (e.g. a second configuration).

At step 702, the user navigates the treatment device to a treatment site. For example, the clinician may navigate the patient's anatomy with the device in the first configuration. The goal of the navigation may be to place the treatment element in contact with the treatment site. In an example, the treatment device is navigated through the nares to an internal nasal valve area of the nasal airway passage. In some embodiments, the clinician may pull the tip of the nose caudally and increase the diameter of the nares to facilitate access to the internal nasal valve for treatment. In some embodiments, access to the airway may be achieved endoscopically via the nares, or via the mouth and throat. In some embodiments, visualization devices may be incorporated or combined with treatment devices for navigation or treatment purposes.

In certain circumstances, advancing a portion of the device to a treatment site may follow the removal of the treatment device. In this circumstance, this step may include the clinician wholly or partially re-navigating the device to improve, for example, contact between the treatment portion and the treatment site.

During navigation, the clinician may perform one or more tests to determine whether proper contact with the treatment site has been made. For example, the clinician may activate one or more pairs of the electrodes. Based on measured results, the clinician may determine that proper contact has not been achieved, because an energy pathway could not be made between one or more pairs of electrodes and/or that one or more measured electrical parameters (e.g., impedance, voltage, current, etc.) is outside of a desired range. As another example, the clinician may attempt to apply pressure to the treatment site with the treatment portion and determine by feel whether proper contact has been made. As yet another example, the clinician may take a reading using a thermocouple to determine whether proper contact has been made.

Based on the one or more tests, the clinician may determine that proper contact has been made between the treatment portion and the treatment site. In this situation, the flow may move to the step 704, which involves delivering therapy to the treatment site. In certain circumstances, the clinician may determine that proper contact has not been made or that the device is otherwise unsuitable in its current state, and the clinician may reposition the device or modify a component thereof and re-navigate until proper contact is made.

At step 704, therapy is delivered at the treatment site. In this step, the clinician may cause the device to apply energy to or remove energy from the treatment site. For example, in certain implementations, a clinician may use the device to apply energy to mucosal tissue and/or an underlying tissue. In some examples, it may be desirable to press the treatment portion against airway tissue such that the tissue substantially conforms to the shape of the treatment element.

For instance, a concave shape may be formed or the tissue may be otherwise remodeled. In some examples, electrodes of the device may be non-penetrating (e.g., resist penetrating tissue, such as by having a blunt or rounded tip) electrodes that protrude from the treatment surface. The electrodes may create indentations in the tissue without piercing or otherwise penetrating the tissue. A portion of the tissue may enter and conform to the shape of a trough of the treatment device and contact a thermocouple. While the tissue is in this configuration, the clinician may activate one or more pairs of electrodes of the treatment device to deliver therapy to the treatment site. In certain implementations, delivering therapy to the treatment site may include delivering radio frequency energy from a first electrode on the treatment portion to a second electrode on the treatment portion to treat tissue such as mucosal tissue, cartilage, bone, muscle and/or skin, to modify a property of the tissue and thus treat a condition associated with the airway. The modification typically remains, in whole or in part, after the treatment element is removed and the tissue heals or otherwise recovers from the treatment.

At step 706, the device may be removed. In certain circumstances, the clinician may remove part or all of the device from the patient. The clinician may determine that one or more further adjustments may improve contact between the treatment portion and the treatment site or otherwise achieve improved therapeutic results. In such circumstances, the flow may move back to the start, and the clinician may re-prepare the device or the patient for treatment. For example, the clinician may articulate one or more components of the device to place the device in a second configuration. The clinician may then navigate to a new or the same treatment site and deliver therapy to the treatment site.

FIGS. 35A and 35B illustrate side, partial cutaway views of an example multi-position treatment device 800 having an adjustable length. The multi-position treatment device 800 can include two or more related portions, at least one of which is movable relative to the other to customize the device 800. For example, extending from a handle 802 of the device 800 is an outer shaft 804. The outer shaft 804 can be fixed relative to the handle 802. An inner shaft 806 is slidably disposed relative the outer shaft 804. As illustrated in the cutaway portion of the example treatment device 800, the outer shaft 804 has a lumen in which the inner shaft 806 is slidably disposed. Extending from the end of the inner shaft 806 is a treatment element 808. In this manner, the outer shaft 804 and the inner shaft 806 form an adjustable shaft connecting the treatment element 808 to the handle 802. As illustrated, the treatment element 808 includes multiple pairs of bipolar electrodes and a thermocouple, though other configurations are also possible.

A fixation mechanism 810 can be used to control the movement of the inner shaft 806 relative to the outer shaft 804. The fixation mechanism 810 can take a variety of different forms including but not limited to a J-lock, a detent, a plug-in-channel, set screws, or other fixation mechanism. In some examples, the fixation mechanism 810 includes a groove, abutment, or other component that guides or limits movement of the inner shaft 806 relative to the outer shaft 804. The fixation mechanism 810 can be used, for example, to lock the outer shaft 804 and the inner shaft 806 into a particular relationship that defines multiple positions.

For example, FIG. 35A illustrates the inner shaft 806 being in an extended position relative the outer shaft 804, thereby defining an extended configuration. In the extended configuration the treatment element 808 is in a relatively distal position compared to other configurations. FIG. 35B illustrates the inner shaft 806 being in a retracted position relative the outer shaft 804, thereby defining a retracted configuration. In the retracted configuration, the treatment element 808 is in a relatively retracted position compared to other configurations.

In the example illustrated in FIGS. 35A and 35B, the fixation mechanism 810 includes a channel 812, in which a peg 814 is disposed. The peg 814 is coupled to the inner shaft 806, such that the peg 814 and the inner shaft 806 move together. In this configuration, the channel 812 guides and controls the movement of the peg 814 (e.g., preventing the peg 814 from leaving the confines of the channel 812), thereby also controlling the movement of the inner shaft 806. In the illustrated configuration, the channel 812 runs substantially parallel to the outer shaft 804. In this manner, the channel 812 cooperates with the peg 814 to allow motion of the inner shaft 806 in a direction substantially parallel to the inner shaft 806 and generally resists other motion of the inner shaft 806, such as twisting, while the inner shaft 806 is within a main portion of the channel 812. In some examples, the peg 814 is configured to be manipulated by the clinician to control the device (e.g., the peg 814 can extend to a particular height or otherwise be readily manipulated by the clinician). In other examples, the peg 814 and channel 812 need not be configured to be manipulated by the user. Instead, the user may use another component to manipulate the device, and one or more portions of the fixation mechanism 810 can be relatively inaccessible to the user (e.g., hidden within the housing of the device 800).

The channel 812 further includes landings 816, in which the peg 814 can rest. The landings 816 can be configured such that once the peg 814 is disposed in a landing 816, the landing 816 inhibits motion of the peg 814. In this manner, the landings 816 can be useful for maintaining a particular position of the peg 814 (and therefore also the inner shaft 806 and treatment element 808). In some examples, the fixation mechanism 810 can include a variety of different landings 816 to facilitate maintaining the treatment device 800 in various configurations. The landings 816 can take a variety of different configurations. In some examples, the landings 816 may be detents or catches in which the peg 814 are arrested. In the illustrated example, the landings 816 are offshoots from the channel 812 extending substantially perpendicular to the channel 812. A user may navigate the peg 814 into the landing 816 by twisting the outer shaft 804 and the inner shaft 806 relative to each other. In some examples, in order to modify engagement of the peg 814 and a landing 816, the user may need to push, pull, twist, or otherwise manipulate the peg 814 or another portion of the treatment device 800 (e.g., there may be a locking button on the handle 802). In some embodiments, the fixation mechanism 810 need not include landings 816. Instead, the fixation element 810 can include set screws, friction fits, or other ways of controlling the relative motion of the components.

The treatment device 800 can include a variety of sensors, electrical components, mechanical components, or other mechanisms for determining a configuration of the device 800. This can include, for example, detecting the position of the components of the treatment device 800, so that action can be taken in response thereto. For instance, as illustrated, there are a position sensor 818 and a position indicator 820 disposed within the treatment device 800. The position sensor 818 is a component for sensing the position of a component of the treatment device 800. The position indicator 820 is a component configured to indicate the position of a portion of the treatment device 800. In particular, the illustrated example shows the position indicator 820 as being disposed in relation to the inner shaft 806, such that the position indicator 820 moves with the inner shaft 806. Additionally, there are multiple position sensors 818 disposed within the handle 802 and the outer shaft 804 configured to sense the position of the position indicator 820.

For example, a first position sensor 818 is disposed to detect when the inner shaft 806 is in a distal-most position (e.g., as shown in FIG. 8A). A second position sensor 818 is disposed to detect when the inner shaft 806 is disposed in a proximal position (e.g., as shown in FIG. 35B).

The position sensors 818 and the position indicator 820 can take a variety of different configurations. In some examples, the position indicator 820 is a conductive component that makes an electrical connection with the position sensor 818, which then produces a position output based on the connection. For instance, the position indicator 820 may be a conductive strip of material that completes a circuit for the position sensor 818. When the circuit is completed, a signal is sent from the position sensor 818, indicating that the position indicator 820 is in a position associated with the particular position sensor 818. In some examples, the position indicator 820 and the position sensor 818 can cooperate to form a potentiometer or a rheostat to provide a more continuous indication of position. In another example, the position indicator 820 may be a magnet, and the position sensor 818 may be a Hall effect sensor.

The output of the position sensor 818 can be provided to a component of the treatment device 800 or a system with which the treatment device 800 cooperates. For example, the position sensor 818 can provide an electrical or mechanical signal to a control system (e.g., control system 242) coupled to the treatment device 800. The control system can then modify operation of the treatment device 800 based on the signal.

For example, a first configuration of the device 800 may be a storage or safety configuration, and the control system may prevent use of the treatment device while in the first configuration. A second configuration of the device 800 may be an operational configuration that allows the clinician to operate the device.

In another example, the control system 242 may not allow operation of the device while the peg 814 is outside of a landing 816. Such a configuration may be determined if no sensor 818 detects the position indicator 820.

In yet another example, the control system 242 may cause the treatment device to operate according to a first set of treatment parameters while the position sensor 818 indicates a first output and may cause the treatment device to operate in a second set of treatment parameters while the position sensor 818 indicates a second output. Treatment parameters can include time, power level, temperature, electric impedance, electric current, and/or depth of treatment, among other selectable parameters. The treatment parameters may be selected based on a particular kind of tissue to be treated. For example, a first configuration may be a configuration for treating a particular region of the airway (e.g., a nasal septum, an inferior turbinate, a middle turbinate, a superior turbinate, a nasal valve region, Eustachian tube opening, mouth, throat, etc.) or a particular area of tissue (e.g., mucosal tissue, submucosal tissue, skin, upper lateral cartilage, lower lateral cartilage, nerve tissue, muscle tissue, cartilage, bone, etc.). The second configuration may be a configuration for treating another region of the airway and/or another kind of tissue.

In a further example, the parameters may be customized for a particular configuration. For instance, two or more clinicians may use a same treatment device, each having different preferences for use. A first configuration may select first parameters for a first clinician, and a second configuration may select second parameters for a second clinician.

In order to move the treatment device 800 from a first configuration to a second configuration, a user may apply force to disengage or otherwise modify a portion of the fixation mechanism 810 and then move one or more components of the treatment device 800. For example, to move from the configuration shown in FIG. 35A to the configuration shown in FIG. 8B, a user may begin by rotating the inner shaft 806 relative to the outer shaft 804, to move the peg 814 out of the landing 816 and into a main portion of the channel 812. This allows motion of the inner shaft 806 (and thus the treatment element 808) in a manner allowed by the channel 812, including movement of the treatment element 808 toward the handle, thereby decreasing an overall length of the treatment device 800. Once the treatment element 808 is in a desired position relative to the rest of the device 800, the user may activate the fixation mechanism 810. In particular, the user may twist the inner shaft 806 relative to the outer shaft 804 to place the peg 814 in a proximal landing 816 to arrive at the configuration illustrated in FIG. 35B.

FIGS. 36A and 36B illustrate an example of a multi-position treatment device 900 having an adjustable treatment direction $D_1$, $D_2$. In particular, treatment device 900 is configured for rotation of the treatment element 908 in a plane substantially perpendicular to a length of the treatment device 900. FIG. 36A illustrates the treatment device 900 in a first configuration. In the first configuration, the treatment element 908 is oriented relative to the handle 902 to allow for treatment in direction $D_1$. FIG. 36B illustrates an example second configuration, in which the treatment element 908 is oriented relative to the handle 902 to allow for treatment in direction $D_2$. Direction $D_2$ is rotated approximately 180 degrees relative to direction $D_1$ in a plane substantially perpendicular to the length of the treatment device 900.

The arrangement of the outer shaft 904 and the inner shaft 906 can be configured to allow for rotation of components of the treatment device 900 in a plane substantially perpendicular to the length of the treatment device 900. For example, as shown, the outer shaft 904 is a tube in which the inner shaft 906 is disposed and can rotate.

The fixation mechanism 910 is configured to allow for the rotation. For example, the illustrated example includes a channel 912 oriented substantially circumferentially around the outer shaft 904, to allow for rotation of the peg 914 (and thus rotation of the second element 906 and the treatment element 908) around the circumference of the outer shaft 904. The fixation mechanism 910 can be configured in a variety of ways to inhibit unwanted motion of portions of the device 900. As with the example of FIGS. 35A and 35B, there may be landings to inhibit unwanted motion of components. In other examples, there may be other kinds of mechanisms.

The position sensor(s) 918 and the position indicator 920 can be arranged to detect rotation. For example, one position sensor 918 can be disposed circumferentially around the outer shaft 904, and the position indicator 920 can be disposed on a relatively small section of the inner shaft 906. Based on which portion of the position sensor 918 detects the position indicator 920, the position sensor 918 can provide an output. In another example, there may be multiple position sensors 918, each configured to detect a rotated position of the position indicator 920.

Rotating the treatment element 908 need not be just for changing a treatment direction. In some examples, the treatment element 908 may be rotated to access different features of the treatment element relative to the treatment direction.

Figures 37A, 37B:
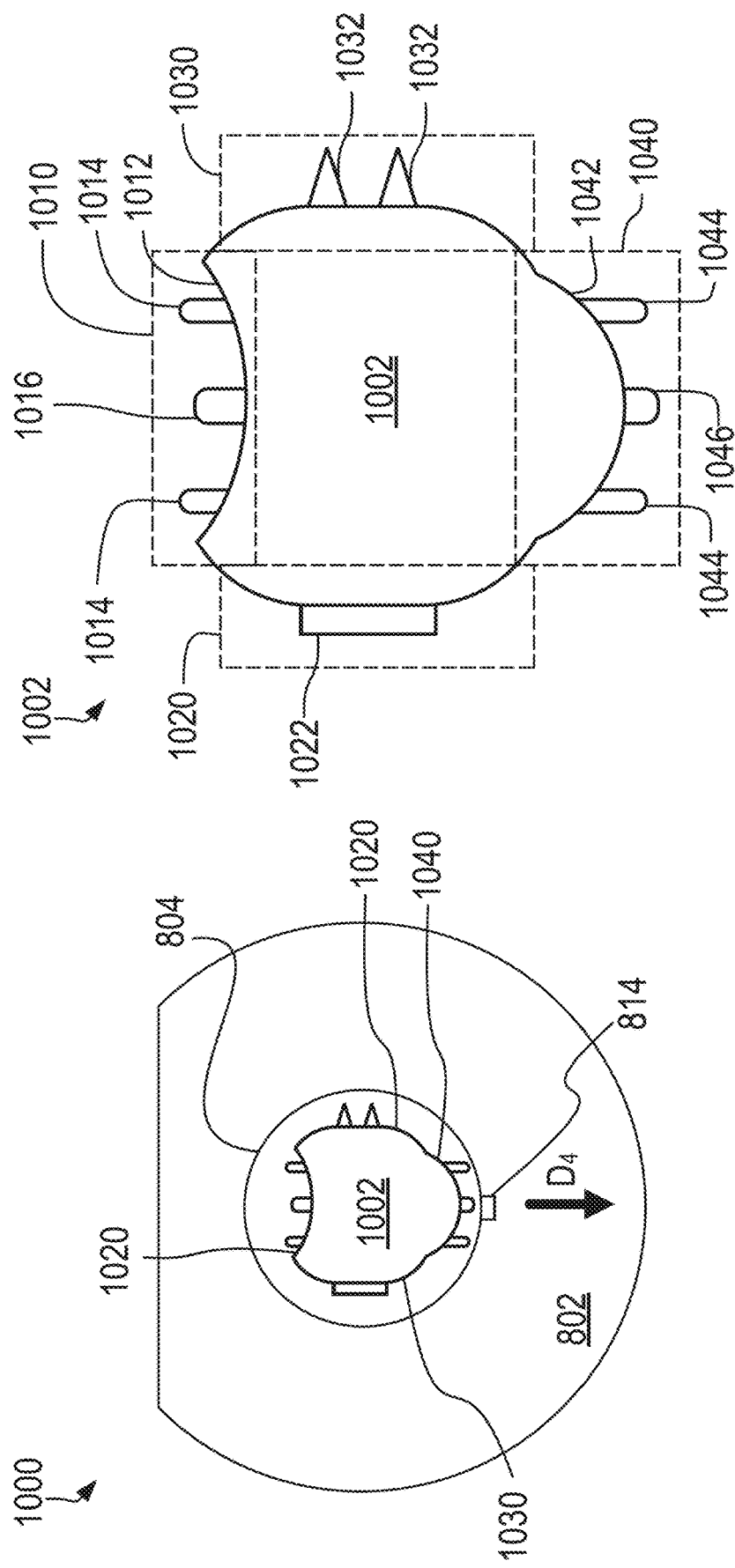
FIGS. 37A and 37B are front views of a treatment device with a rotatable treatment element that provides selective access to various treatment portions, according to one embodiment.

FIGS. 37A and 37B illustrate an example of a treatment device 1000 with a rotatable treatment element 1002 that provides selective access to various treatment portions 1010, 1020, 1030, 1040.

FIG. 37A illustrates an end-on view of the treatment device 1000. The device 1000 can be arranged to provide treatment in a particular direction $D_4$. Direction $D_4$ may vary, based on a variety of parameters, including clinician preference. For example, the treatment direction $D_4$ as shown in FIG. 37A is the same regardless of which treatment portion 1010, 1020, 1030, 1040 is selected. As illustrated in FIG. 37B, the treatment element 1002 has a variety of treatment portions 1010, 1020, 1030, 1040 arrayed circumferentially around the treatment element 1002. Each of the portions 1010, 1020, 1030, 1040 is adapted to provide a particular kind of treatment. The device 1000 is customizable by rotating the treatment element 1002 (e.g., as shown or described in relation to FIGS. 9A and 9B) to allow for treatment in the treatment direction $D_4$ by a variety of the treatment portions. For example, in the configuration shown in FIG. 37A, the device 1000 is arranged such that providing treatment in direction $D_4$ involves providing treatment with treatment portion 1040. However, the clinician may cause the treatment element 1002 to be rotated, such that a different treatment surface is arranged to provide treatment and direction $D_4$. Thus, the device 1000 provides multiple different types of treatment surfaces the clinician can use in a given procedure.

FIG. 37B illustrates a detailed view of the treatment element 1002 and its various treatment portions 1010, 1020, 1030, 1040. For example, in a first treatment portion 1010, there are one or more pairs of non-penetrating (e.g., blunted) bipolar electrodes 1014 disposed on a concave treatment surface 1012. The treatment portion 1010 may further include a thermocouple or other sensor 1016 disposed between the pairs of electrodes 1014. A second treatment portion 1020 includes a treatment mechanism 1022 configured to provide a treatment different from the treatment provided by portion 1010. For example, where treatment portion 1010 provides treatment using bipolar electrodes 1014, treatment mechanism 1022 can be configured to provide cryotherapy, chemical therapy, or another kind of treatment. Treatment portion 1030 includes at least one pair of bipolar penetrating (e.g., needle) pairs of electrodes 1032. Treatment portion 1040 includes one or more pairs of non-penetrating bipolar electrode pairs 1044 and a thermocouple or other sensor 1046 disposed on a convex treatment surface 1042. A clinician may access these various treatment regions by rotating the treatment element 1002 into a desired rotation relative to the rest of the device 1000.

Figure 38:
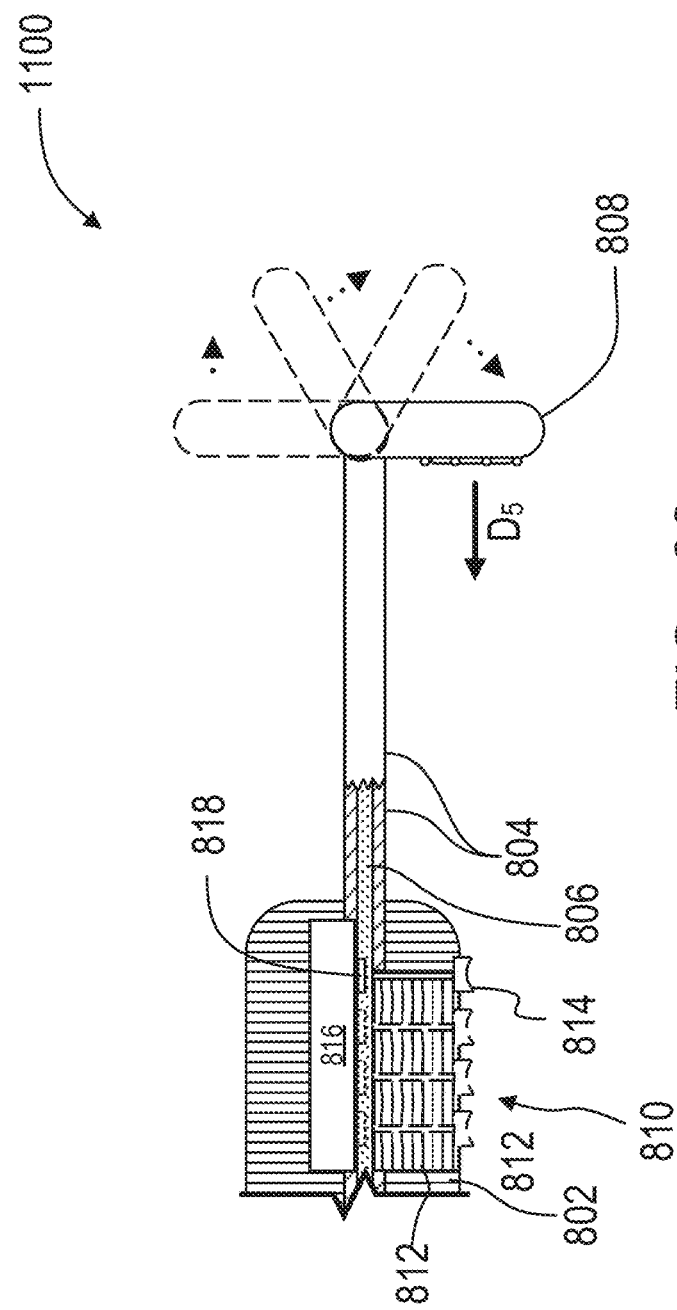
FIG. 38 is a partial cutaway, side view of a multi-position treatment device with a tiltable treatment element, according to one embodiment.

FIG. 38 illustrates an example embodiment of a multi-position treatment device 1100 that includes a tiltable treatment element 1108. The treatment element 1108 can be tilted to allow an adjustable treatment direction $D_5$ within a plane substantially parallel to the length of the treatment device 1100. The tiltable treatment element 1108 may be achieved in a variety of ways. In one example, the inner shaft 1106 is slidably disposed within the outer shaft 1104, and there is a coupling or other linkage where the outer shaft 1104 meets the treatment element 1108, such that movement of the inner shaft 1106 causes the treatment element 1108 to tilt. For example, the peg 1114 may be a movable button portion that can be slid along the channel 1112, thereby moving the inner shaft 1106 within the outer shaft 1104, thereby causing the treatment element 1108 to tilt and change the treatment direction $D_5$. Again, there may be a position sensor 1118 and a position indicator 1120 arranged to detect a bend or other configuration of the treatment element 1108. Multiple exemplary positions of the treatment element 1108, pegs 1114, and position indicator 1120 are illustrated in dashed lines.

FIG. 38 further illustrates the fixation element 1110 disposed within the handle 1102. In particular, there is a channel 1112 extending through the handle 1102 and in communication with the inner shaft 1106, such that the channel 1112 allows movement of the peg 1114 when the peg 1114 is connected to the inner shaft 1106. The peg 1114 is formed as a sliding button with a concavity for receiving the clinician's thumb.

FIGS. 39A-39C illustrate a distal end of an example treatment device 1200 having a rotatable treatment element 1202 that can rotate relative to a shaft 1204, in a plane substantially parallel to the length of the treatment device 1200. Upon actuation of the components, the treatment element 1202 can rotate relative to the shaft 1204. For example, there may be a backing component 1206 that serves as a base on which the treatment number 1202 can rotate. There may be gears or other rotating components within the backing component 1206 that allow for rotation of the treatment element 1202. FIG. 39B illustrates the treatment element 1202 moving in a direction indicated by arrows to reach the position illustrated in FIG. 39C. FIG. 39C illustrates an example arrangement of the treatment device 1200 after rotating the treatment element 1202 relative to the shaft 1204.

Figure 40C:
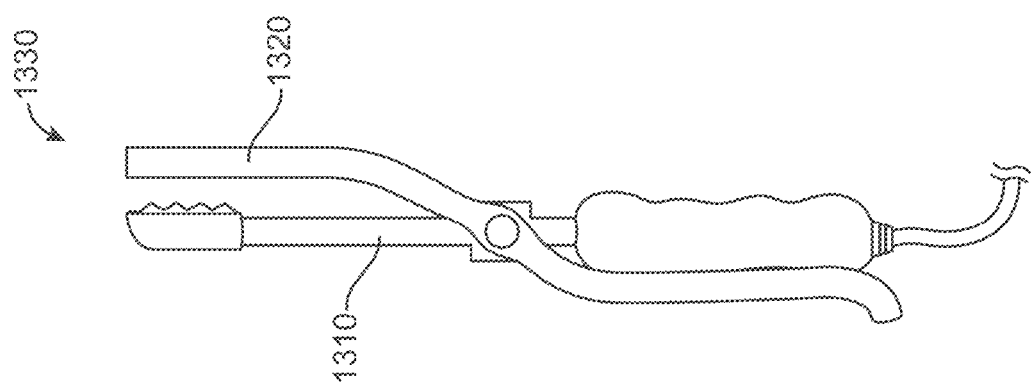
FIGS. 40A-40C are perspective views of a two-part treatment device formed from a supporting feature coupled to a base treatment device with an attachment element, according to one embodiment.
Figure 40B:
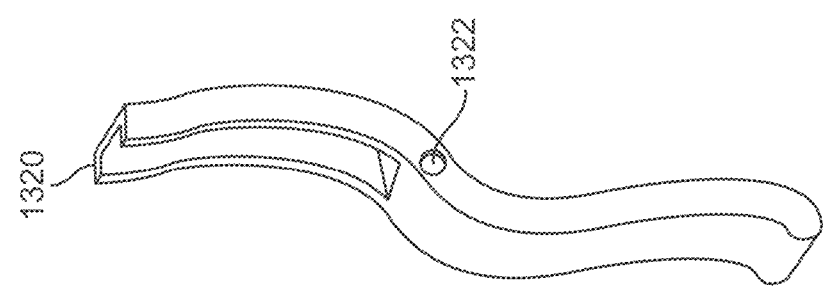
Figure 40A:
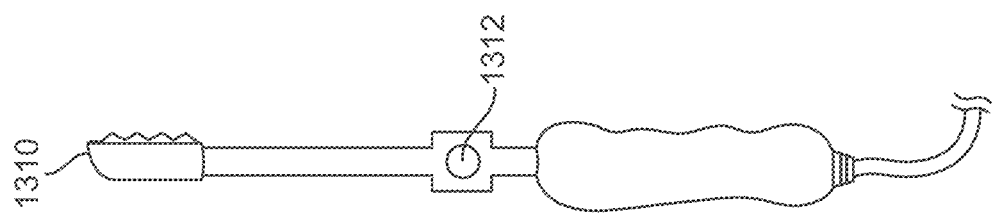

FIGS. 40A-40C illustrate an example of a two-piece, reconfigurable treatment device 1330. Referring to FIG. 40A, a base treatment device 1310 can include an attachment element 1312. FIG. 40B shows a supporting feature 1320 with a complementary attachment element 1322. The base treatment device 1310 can be coupled to the supporting feature 1320 via their respective attachment elements 1312, 1322, to form the combined, two-piece treatment device 1330 of FIG. 40C. The two-piece device can be used in a clamping or tissue-holding procedure, in which tissue is held between the two parts 1310, 1320 of the device 1330.

In the illustrated example, the base treatment device 1310 may include any of the aspects and features described above, for example including a treatment element having bipolar electrodes configured to deliver energy to a treatment site. The supporting feature 1320 may include a clamp portion, an electrode array, an incision forming device, a second treatment device (e.g., to allow for treatment via two nostrils simultaneously), a positioning device, a treatment device configured to provide a different treatment modality than that provided via the base treatment device 1310 (e.g., cryotherapy, chemical, etc.), a sensor array and/or any other such features.

In some examples, one or both of the attachment elements 1312, 1322 or another portion of one or both of the treatment device parts 1310, 1320 may include one or more sensors to determine whether a supporting feature 1320 is attached to the base treatment device 1310 and what kind of supporting feature 1320 is attached. The sensors can provide an output based on the supporting feature 1320 (or lack thereof), and the output can be used to change parameters by which the base treatment device 1310 or the combined treatment device 1330 operates. For example, upon detecting that a clamp supporting feature 1320 is attached, clamp treatment parameters can be automatically selected and used.

Referring back to FIGS. 6 and 9 that illustrate a method for treating nerves in the nasal cavity, any of the device, system and method embodiments described above may be used to treat any nerve or combination of nerves in the nasal cavity in order to treat one or more conditions that occur inside the nasal cavity, outside the nasal cavity or both. As mentioned above, conditions outside the nasal cavity that may be addressed by treating nasal cavity nerves include but are not limited to asthma, chronic obstructive pulmonary disease (COPD), airway inflammation, eye inflammation and allergic conjunctivitis, allergies, headaches, pain (such as facial nerve pain), anxiety, mood disorders, middle ear conditions such as otitis media, reduction of chemical mediators that lead to any of the above-listed conditions, and/or the like. In treating the nasal cavity nerve(s), the method may involve neuromodulation, in which the treatment alters the nerve function, typically by decreasing it. In some cases, nasal neuromodulation may involve completely ablating a nerve, to completely cut off its function. This effect may be temporary or permanent, depending for example on the amount of energy delivered and/or the amount of time the energy is delivered.

Figure 41:
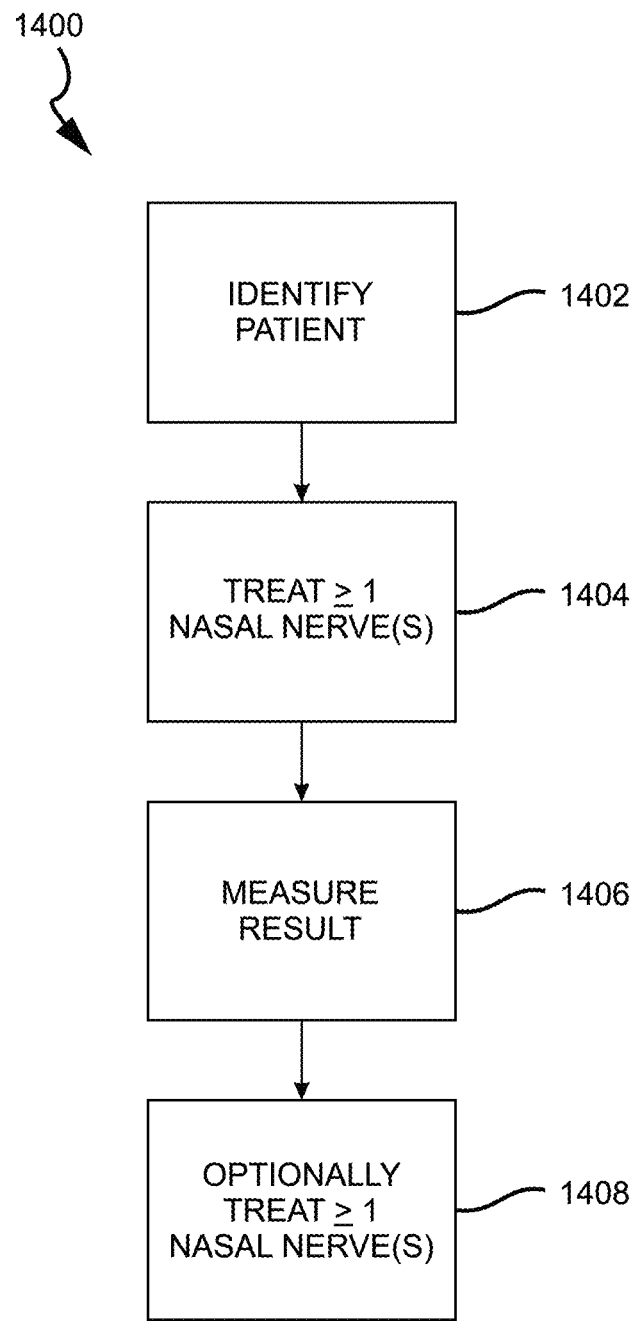
FIG. 41 is a diagram of a method for treating nasal nerves to address a condition outside the nasal cavity, according to one embodiment.

Referring now to FIG. 41, a method 1400 for treating a patient is diagrammed. This method 1400 may first involve identifying a patient 1402 who suffers from a disease or condition located outside the nasal cavity, where the disease or condition may be ameliorated by the treatment of one or more nerves in the nasal cavity. Examples of such conditions include asthma, COPD, airway inflammation, eye inflammation and allergic conjunctivitis, allergies, migraine headaches, other headaches, tinnitus, dizziness, vertigo, dry eye, excessive tearing, pain, anxiety, mood disorders, middle ear conditions such as otitis media, herpes zoster, paroxysmal hemicranias, and/or cancer of the head or neck. The method 1400 then involves treating one or more nasal nerves 1404, which generally refers to any nerve(s) located anywhere within the nasal cavity, such as but not limited to the vidian nerve, the sphenopalatine ganglion, a posterior nasal nerve, or any branches of the vidian nerve or sphenopalatine ganglion. Treatment may involve delivery of energy to (or removal of energy from) nerve tissue, using an energy delivery (or removal) device, such as but not limited to bipolar RF energy, monopolar RF energy, heat, ultrasound, cryotherapy, laser or chemical energy.

In some embodiments, the method 1400 may further involve measuring a result of the nasal nerve treatment 1406, using any suitable measurement technique. In some embodiments, the initial nerve treatment 1404 may simply be a test stimulation or partial treatment, in order to determine whether the patient's condition will be positively affected by the nasal neuromodulation. In other embodiments, the treatment 1404 may be a full treatment, and results may be measured 1406 after full treatment. A final, optional step involves treating one or more nasal nerves again 1408, which may be the same nasal nerves that were treated before or a different nerve or set of nerves. After this second round of nerve treatment 1408, results may again be measured 1406.

In one specific example, certain headaches, such as migraine headaches, are thought to be nasogenic (i.e., they may arise from something happening in the nasal cavity). For example, one cause of migraine headaches might be pressure or contact points in the nasal passage that stimulate nerves. A migraine (or other headache patient) may be identified, according to the method 1400 described above, and any one of the device/system embodiments described above may use radiofrequency energy (or other energy form) to shrink and/or push down tissue at these contact points in the nasal cavity to reduce pressure and/or to ablate nerves and nerve endings to reduce nerve activity. In another embodiment, the method may involve using the devices/systems described above to provide a sphenopalatine ganglion nerve block to treat headaches, or alternatively to treat nasal nerves downstream from the sphenopalatine ganglion, to stop or reduce conduction to the sphenopalatine ganglion and beyond. In various embodiments, the devices and systems described herein may be used to treat migraine headaches, cranial and trigeminal cephalgias, migraine trigger points in facial nerve branches (e.g., frontal facial trigger points (eyebrow region)), other forms of headaches, and/or the like. Nerves that may be treated include any of the nerves listed herein, such as but not limited to posterior nasal nerves, vidian nerve, vidian nerve branches, occipital nerve, trigeminal nerve, trigeminal nerve branches, the sphenopalatine ganglion, and any nerve(s) branching off the sphenopalatine ganglion.

Although the above description focuses on the application of bipolar radiofrequency energy to treat nerve tissue, any of the above-described embodiments may be altered, or other embodiments may be provided, which use any other suitable form of energy, such as but not limited to monopolar RF, ultrasound, heat, laser, cryotherapy (or the removal of energy), chemical energy or the like. In some embodiments, the treatment method may include stimulating nerve tissue before treating, to detect the location of the nerve. This stimulation may be performed with an RF electrode or other stimulatory mechanism. In some embodiments, ultrasound may be used to visualize nerve tissue. In general, the treatments described herein involve treating nerve tissue that resides below the mucosa that lines the nasal cavity. In some embodiments, the distal tip of the stylus used for treatment may be aligned in a horizontal or close to horizontal orientation when applied to the mucosa. In other embodiments, the distal tip may be aligned in a vertical or close to vertical orientation, or any orientation between horizontal and vertical. In some embodiments, the distal tip may be adjusted before or during the treatment, to achieve the vertical or near vertical orientation.

Although this application is believed to be complete and accurate, any suitable changes may be made to any of the described embodiments and features described above, without departing from the scope of the invention.

I claim:
1. A method for treating headaches, the method comprising:
    identifying a patient suffering from headaches;
    activating a console attached to a radiofrequency stylus;
    advancing a distal tip of the radiofrequency stylus into a nasal cavity of the patient, wherein the distal tip comprises:
        a first treatment element having a first treatment surface, the first treatment surface configured to include
        a first plurality of bipolar radiofrequency electrodes disposed on the first treatment surface to treat a first tissue area of nasal mucosa; and
        a second treatment element positioned distal of the first treatment element, the second treatment element having a second treatment surface configured to include a second plurality of bipolar radiofrequency electrodes to treat a second tissue area of the nasal mucosa;
    contacting nasal mucosa lining the nasal cavity with the first treatment surface and the second treatment surface of the distal tip, to cause the first plurality of bipolar radiofrequency electrodes to contact the first tissue area and the second plurality of bipolar radiofrequency electrodes to contact the second tissue area of the nasal mucosa;

applying a pressure with the first treatment surface or the second treatment surface on the nasal mucosa;
determining, using the first treatment surface or the second treatment surface, if the pressure applied to the nasal mucosa is sufficient to confirm contact between the first treatment surface and the first tissue area or the second treatment surface and the second tissue area of the nasal mucosa;
activating at least one electrode pair from the first plurality of bipolar radiofrequency electrodes or the second plurality of bipolar radiofrequency electrodes when the pressure applied by the first treatment surface is sufficient to confirm contact between the first treatment surface and the first tissue area or the pressure applied by the second treatment surface is sufficient to confirm contact between the second treatment surface and the second tissue area of the nasal mucosa;
delivering radiofrequency energy to at least one electrode pair of the first plurality of bipolar radiofrequency electrodes to ablate at least one posterior nasal nerve underlying the first tissue area of the nasal mucosa; and
delivering radiofrequency energy from the at least one electrode pair of the second plurality of bipolar radiofrequency electrodes to disrupt at least one posterior nasal nerve underlying the second tissue area of the nasal mucosa,
wherein disrupting the at least one posterior nasal nerve ameliorates the headaches.

2. The method of claim 1, further comprising:
moving the distal tip to multiple additional locations within the nasal cavity; and
delivering radiofrequency energy to the at least one posterior nasal nerve or a different nerve at the multiple additional locations.

3. The method of claim 1, further comprising sensing a temperature of the nasal mucosa with a temperature sensing member located on the first treatment surface or the second treatment surface.

4. The method of claim 3, further comprising automatically shutting off delivery of radiofrequency energy from the console to the radiofrequency stylus if the temperature is above a predefined acceptable maximum temperature.

5. The method of claim 1, wherein the at least one posterior nasal nerve is selected from the group consisting of a sphenopalatine ganglion, a branch of a vidian nerve, a branch of the sphenopalatine ganglion, a trigeminal nerve, and an occipital nerve.

6. The method of claim 1, further comprising bending a shaft of the radiofrequency stylus before advancing the distal tip into the nasal cavity.

7. The method of claim 1, further comprising treating an additional tissue in the nasal cavity, wherein the additional tissue is selected from the group consisting of an inferior turbinate, a middle turbinate, a superior turbinate, a nasal septum, and a septal swell body.

8. The method of claim 1, further comprising changing at least one of an orientation or a shape of the distal tip before or after advancing the distal tip into the nasal cavity.

9. The method of claim 8, wherein the distal tip is changed to achieve a vertical or near vertical orientation relative to the nasal cavity.

10. The method of claim 1, wherein the headaches comprise migraine headaches.

11. The method of claim 1, further comprising confirming that the pressure is sufficient with the first treatment surface or the second treatment surface of the radiofrequency stylus against the first tissue area or the second tissue area of the nasal mucosa to confirm contact between the first treatment surface or the second treatment surface and the first tissue area or the second tissue area of the nasal mucosa.

12. A method for treating headaches, the method comprising:
identifying a patient suffering from headaches;
advancing a distal tip of a radiofrequency stylus into a nasal cavity, wherein the distal tip comprises:
a first treatment element having a first treatment surface, the first treatment surface configured to include a first plurality of bipolar radiofrequency electrodes disposed on the first treatment surface to treat a first tissue area of nasal mucosa; and
a second treatment element configured to expand from a first configuration positioned inside the distal tip and a second configuration to contact a second tissue area of the nasal mucosa, the second treatment element having a second treatment surface configured to include a second plurality of bipolar radiofrequency electrodes to treat the second tissue area of the nasal mucosa;
contacting nasal mucosa lining the nasal cavity with the first treatment surface and the second treatment surface of the distal tip, to cause the first plurality of bipolar radiofrequency electrodes to contact the first tissue area and the second plurality of bipolar radiofrequency electrodes to contact the second tissue area of the nasal mucosa;
determining a pressure applied to the nasal mucosa the nasal cavity by the first treatment surface or the second treatment surface;
activating at least one electrode pair from the first plurality of bipolar radiofrequency electrodes or the second plurality of bipolar radiofrequency electrodes, using a console in electrical communication with the at least one electrode pair, when the pressure applied by the first treatment surface is sufficient to confirm contact between the first treatment surface and the first tissue area or the pressure applied by the second treatment surface is sufficient to confirm contact between the second treatment surface and the second tissue area of the nasal mucosa; and
delivering radiofrequency energy to the at least one electrode pair of the first plurality of bipolar radiofrequency electrodes on the first treatment surface to ablate at least one posterior nasal nerve underlying the first tissue area of the nasal mucosa and delivering radiofrequency energy to the at least one electrode pair of the second plurality of bipolar radiofrequency electrodes on the second treatment surface to ablate at least one posterior nasal nerve underlying the second tissue area of the nasal mucosa,
wherein ablating the at least one posterior nasal nerve ameliorates the headaches.

13. The method of claim 12, further comprising:
moving the distal tip to multiple additional locations within the nasal cavity; and
delivering radiofrequency energy to the at least one posterior nasal nerve or a different nerve at the multiple additional locations.

14. The method of claim 12, further comprising sensing a temperature of the nasal mucosa with a temperature sensing member located on the first treatment surface or the second treatment surface.

15. The method of claim 14, further comprising automatically shutting off delivery of radiofrequency energy from the console to the radiofrequency stylus if the temperature is above a predefined acceptable maximum temperature.

16. The method of claim 12, wherein the at least one posterior nasal nerve is selected from the group consisting of a sphenopalatine ganglion, a branch of a vidian nerve, a branch of the sphenopalatine ganglion, a trigeminal nerve, and an occipital nerve.

17. The method of claim 12, further comprising confirming the sufficient pressure with the first treatment surface or the second treatment surface of the radiofrequency stylus against the first tissue area or the second tissue area of the nasal mucosa to confirm contact between the first treatment surface or the second treatment surface and the first tissue area or the second tissue area of the nasal mucosa.

18. A method for treating headaches, the method comprising:
  identifying a patient suffering from headaches;
  activating a console attached to a radiofrequency stylus;
  advancing a distal tip of a radiofrequency stylus into a nasal cavity, wherein the distal tip comprises:
    a first treatment element having a first treatment surface, the first treatment surface configured to include
    a first plurality of bipolar radiofrequency electrodes disposed on the first treatment surface to treat a first tissue area of nasal mucosa; and
    a second treatment element positioned distal of the first treatment element, the second treatment element having a second treatment surface configured to include a second plurality of bipolar radiofrequency electrodes to treat a second tissue area of the nasal mucosa;
  contacting the nasal mucosa of the nasal cavity with the first treatment surface and the second treatment surface, to cause at least one electrode pair of the first plurality of bipolar radiofrequency electrodes to contact the first tissue area and at least one electrode pair of the second plurality of bipolar radiofrequency electrodes to contact the second tissue area of the nasal mucosa;
  applying a pressure with the first treatment surface or the second treatment surface on the first tissue area or the second tissue area of the nasal mucosa;
  determining, using the first treatment surface or the second treatment surface, if the pressure applied to the nasal mucosa is sufficient to confirm contact between the first treatment surface and the first tissue area or the second treatment surface and the second tissue area of the nasal mucosa;
  activating at least one electrode pair from the first plurality of bipolar radiofrequency electrodes or the second plurality of bipolar radiofrequency electrodes when the pressure applied by the first treatment surface is sufficient to confirm contact between the first treatment surface and the first tissue area or the pressure applied by the second treatment surface is sufficient to confirm contact between the second treatment surface and the second tissue area of the nasal mucosa;
  measuring impedance with the at least one electrode pair from the first plurality of bipolar radiofrequency electrodes or the second plurality of bipolar radiofrequency electrodes;
  determining, via the console, that the impedance is within a desired range that indicates sufficient contact of the at least one electrode pair from the first plurality of bipolar radiofrequency electrodes with the first tissue area or the at least one electrode pair from the second plurality of bipolar radiofrequency electrodes with the second tissue area of the nasal mucosa;
  delivering radiofrequency energy to the at least one electrode pair of the first plurality of bipolar radiofrequency electrodes on the first treatment surface to ablate at least one posterior nasal nerve underlying the first tissue area of the nasal mucosa and delivering radiofrequency energy to the at least one electrode pair of the second plurality of bipolar radiofrequency electrodes on the second treatment surface to ablate at least one posterior nasal nerve underlying the second tissue area of the nasal mucosa;
  wherein ablating the at least one posterior nasal nerve ameliorates the headaches.

\* \* \* \* \*